(12) United States Patent
Quail et al.

(10) Patent No.: US 10,722,517 B2
(45) Date of Patent: Jul. 28, 2020

(54) COMPOSITIONS AND METHODS FOR TREATMENT OF GLIOMA

(71) Applicant: MEMORIAL SLOAN KETTERING CANCER CENTER, New York, NY (US)

(72) Inventors: Daniela Francis Quail, Montreal (CA); Johanna Alexandra Joyce, Lausanne (CH); Robert Lyle Bowman, New York, NY (US)

(*) Notice: Subject to any disclaimer, the term of this patent is extended or adjusted under 35 U.S.C. 154(b) by 0 days.

(21) Appl. No.: 15/572,456

(22) PCT Filed: May 9, 2016

(86) PCT No.: PCT/US2016/031431
§ 371 (c)(1),
(2) Date: Nov. 7, 2017

(87) PCT Pub. No.: WO2016/182988
PCT Pub. Date: Nov. 17, 2016

(65) Prior Publication Data
US 2018/0125852 A1 May 10, 2018

Related U.S. Application Data

(60) Provisional application No. 62/158,671, filed on May 8, 2015.

(51) Int. Cl.
*A61K 31/428* (2006.01)
*A61K 31/4985* (2006.01)
*A61K 31/5377* (2006.01)
*A61P 35/00* (2006.01)
*A61K 45/06* (2006.01)
*A61K 31/4439* (2006.01)
*A61P 25/00* (2006.01)
*A61K 31/416* (2006.01)
*A61K 31/4184* (2006.01)
*A61K 31/423* (2006.01)
*A61K 31/426* (2006.01)
*A61K 31/437* (2006.01)
*A61K 31/4406* (2006.01)
*A61K 31/47* (2006.01)
*A61K 31/496* (2006.01)
*A61K 31/517* (2006.01)
*A61K 31/519* (2006.01)

(52) U.S. Cl.
CPC ........ *A61K 31/5377* (2013.01); *A61K 31/416* (2013.01); *A61K 31/4184* (2013.01); *A61K 31/423* (2013.01); *A61K 31/426* (2013.01); *A61K 31/428* (2013.01); *A61K 31/437* (2013.01); *A61K 31/4406* (2013.01); *A61K 31/4439* (2013.01); *A61K 31/47* (2013.01); *A61K 31/496* (2013.01); *A61K 31/4985* (2013.01); *A61K 31/517* (2013.01); *A61K 31/519* (2013.01); *A61K 45/06* (2013.01); *A61P 25/00* (2018.01); *A61P 35/00* (2018.01); *A61K 2300/00* (2013.01)

(58) Field of Classification Search
CPC .............. A61K 31/428; A61K 31/4985; A61K 31/5377; A61P 35/00
See application file for complete search history.

(56) References Cited

U.S. PATENT DOCUMENTS

| 6,827,931 B1 | 12/2004 | Donovan |
| 2009/0054508 A1* | 2/2009 | Kanda .................. C07D 231/56 514/406 |
| 2014/0023661 A1 | 1/2014 | Huang et al. |
| 2014/0037642 A1 | 2/2014 | McCaffery |

FOREIGN PATENT DOCUMENTS

| WO | 20120151541 A1 | 11/2012 | |
| WO | WO-2012151541 A1 * | 11/2012 | ......... A61K 31/4439 |
| WO | 2013158559 A1 | 10/2013 | |
| WO | 2013188763 A1 | 12/2013 | |

OTHER PUBLICATIONS

Wen et al. (Neuro-Oncology, May 22, 2012, 14, 819-829) (Year: 2012).*
Bjerke et al. (Neuro-Oncology, Jun. 2012, i66) (Year: 2012).*
International Search Report & Written Opinion for PCT/US2016/031431.
Pyonteck et al., "CSF-1R inhibition alters macrophage polarization and blocks glioma progression," Nature Medicine; 2013; vol. 19(10); p. 1264-1272.
Coniglio et al: "Microglial Stimulation of Glioblastoma Invasion Involves Epidermal Growth Factor Receptor (EGFR) and Colony Stimulating Factor 1 Receptor (CSF-1 R) Signaling", Molecular Medicine, vol. 18, No. 3, Jan. 27, 2012 (Jan. 27, 2012), pp. 519-527.
Quail et al., Microenvironmental regulation of tumor progression and metastasis. Nat. Med. 19, 1423-1437 (2013).
Junttila et al. Influence of tumour micro-environment heterogeneity on therapeutic response. Nature. 501, 346-354 (2013).

(Continued)

Primary Examiner — Theodore R. West
(74) Attorney, Agent, or Firm — Grimes & Yvon LLP

(57) ABSTRACT

In certain embodiments the present invention provides methods useful in the treatment of glioma, such as glioblastoma, such methods comprising administering to a subject in need thereof a CSF-IR inhibitor together with one or more additional active agents such as IGF-IR inhibitors, PI3K inhibitors, IL4 inhibitors, NFAT inhibitors, and/or Stat6 inhibitors. In certain embodiments the present invention provides pharmaceutical compositions comprising a CSF-IR inhibitor together with one or more of such additional active agents.

19 Claims, 67 Drawing Sheets

(56) References Cited

OTHER PUBLICATIONS

Stupp et al., Radiotherapy plus concomitant and adjuvant temozolomide for glioblastoma. N. Engl. J. Med. 352, 987-996 (2005).

Komohara et al. Possible involvement of the M2 anti-inflammatory macrophage phenotype in growth of human gliomas. J. Pathol. 216, 15-24 (2008).

Bingle et al. The role of tumour-associated macrophages in tumour progression: implications for new anticancer therapies. J. Pathol. 196, 254-265 (2002).

Hussain et al. The role of human glioma-infiltrating microglia/macrophages in mediating antitumor immune responses. Neuro. Oncol. 8, 261-279 (2006).

Ruffell et al. Macrophages and Therapeutic Resistance in Cancer. Cancer Cell. 27, 462-472 (2015).

Patel et al. Colony-stimulating factor-1 receptor inhibitors for the treatment of cancer and inflammatory disease. Curr. Top. Med. Chem. 9, 599-610 (2009).

Ries et al. Targeting tumor-associated macrophages with anti-CSF-1R antibody reveals a strategy for cancer therapy. Cancer Cell. 25, 846-859 (2014).

Tap et al. Structure-Guided Blockade of CSF1R Kinase in Tenosynovial Giant-Cell Tumor. N. Engl. J. Med. 373, 428-437 (2015).

\* cited by examiner

Fig. 4A  Fig. 4B

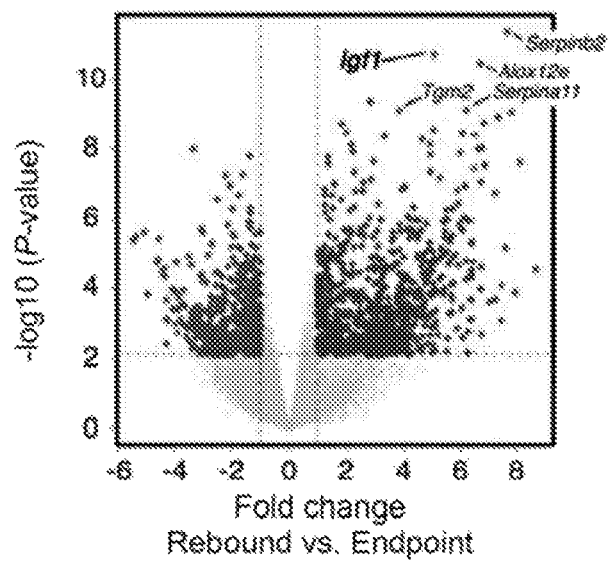
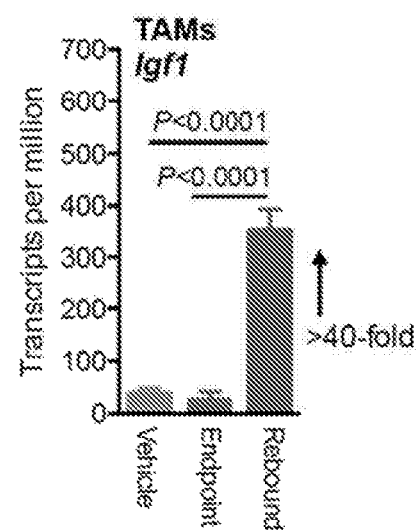
Fig. 5A  Fig. 5B
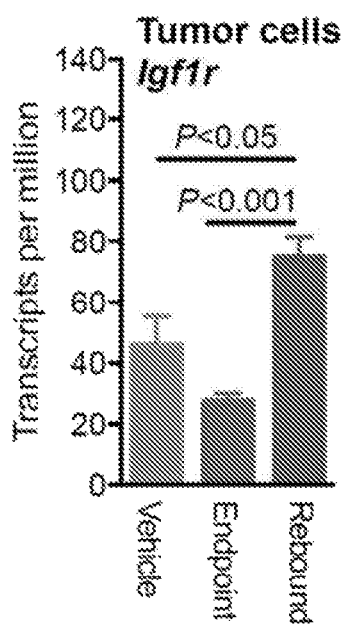
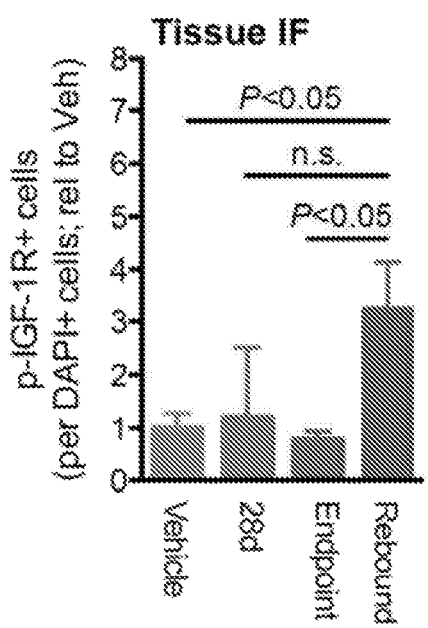
Fig. 5C  Fig. 5D

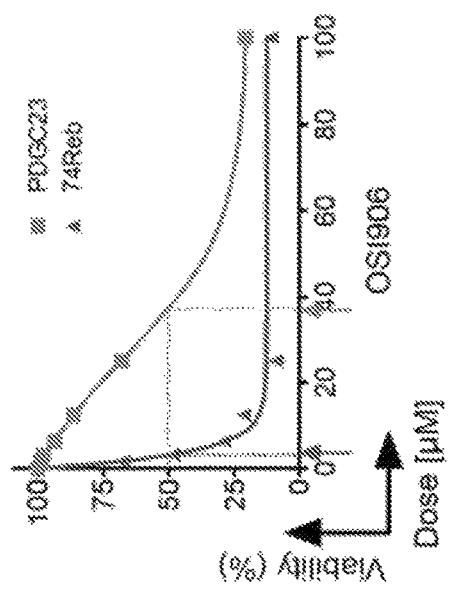
Fig. 5E
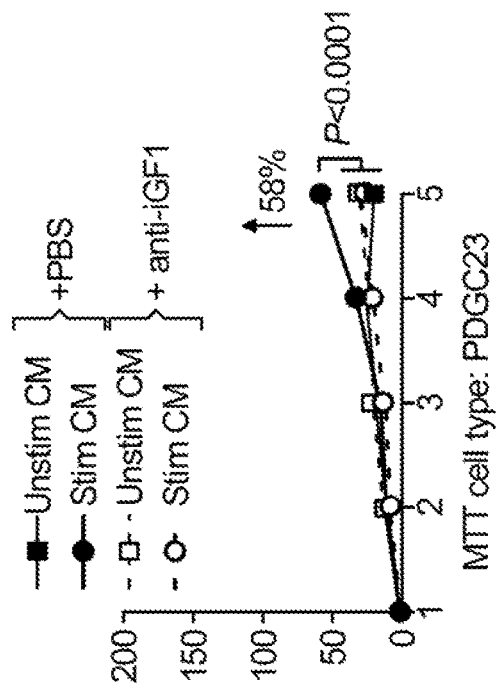
Fig. 5F
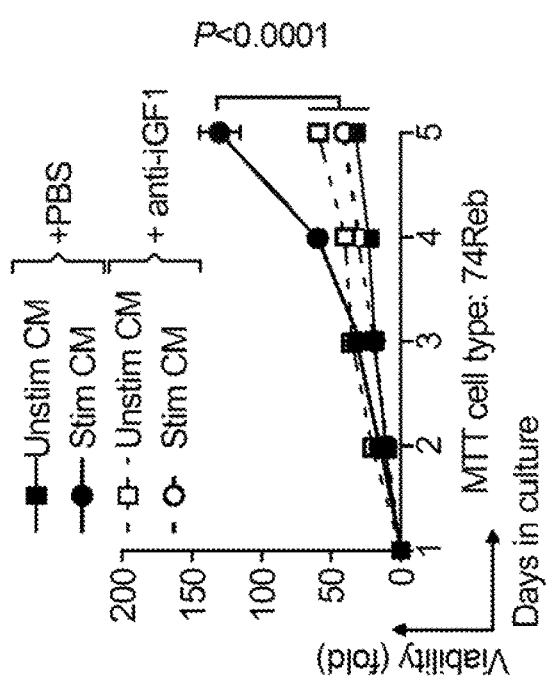

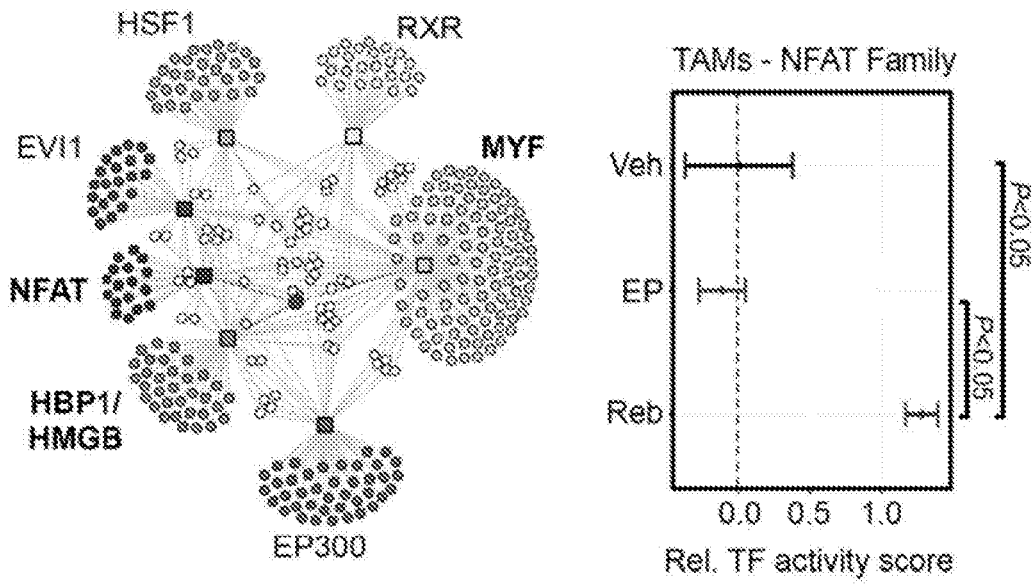
Fig. 6A
Fig. 6B
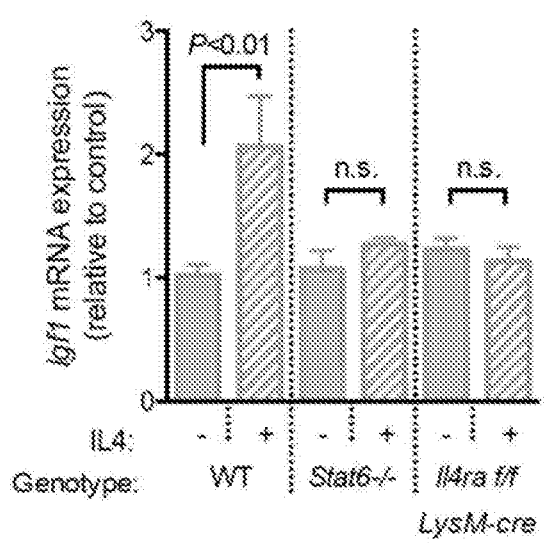
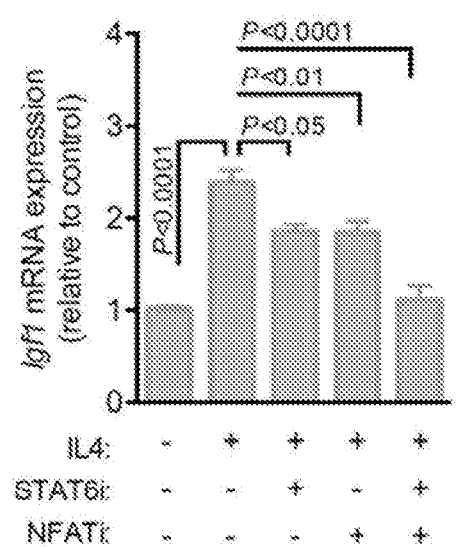
Fig. 6C
Fig. 6D

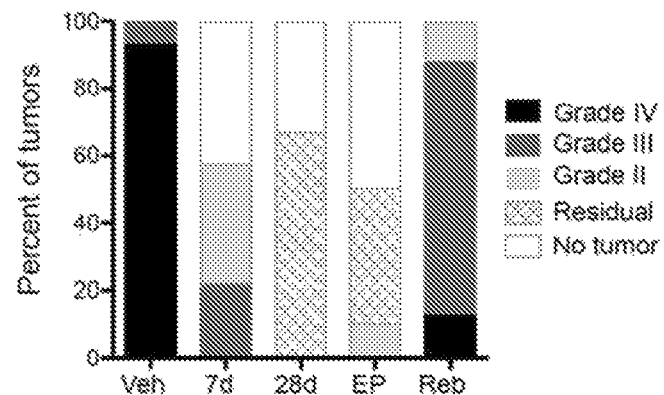
Fig. 9D
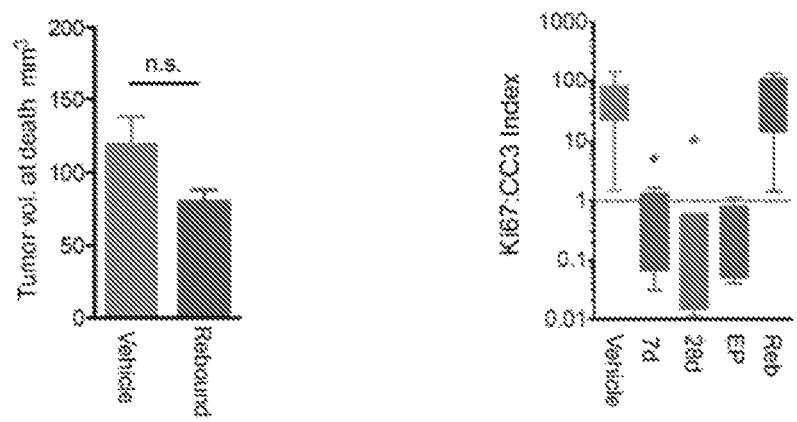
Fig. 9E  Fig. 9F

| Gene set | Fold change | P-value |
|---|---|---|
| Vehicle vs. Rebound | | |
| MOOTHA_TCA | 2.01 | 9.65E-05 |
| BIOCARTA_ETC_PATHWAY | 2.11 | 2.16E-05 |
| Vehicle vs. Endpoint | | |
| SOTIRIOU_BREAT_CANCER_GRADE_1_VS_3_UP | 2.03 | 5.71E-06 |
| ODONNELL_TARGETS_OF_MYC_AND_TFRC_DN | 2.00 | 8.49E-06 |
| EGUCHI_CELL_CYCLE_RB_TARGETS | 2.01 | 4.53E-05 |
| MANN_RESPONSE_TO_AMIFOSTINE_DN | 2.08 | 1.23E-07 |
| SCIAN_CELL_CYCLE_TARGETS_OF_TP53_AND_TP73_DN | 2.13 | 4.20E-06 |
| CAFFAREL_RESPONSE_TO_THC_8HR_3_DN | 2.01 | 4.38E-06 |
| MENSSEN_MYC_TARGETS | 2.00 | 4.51E-07 |
| KANG_DOXORUBICIN_RESISTANCE_UP | 2.11 | 5.40E-06 |
| REICHERT_G15_REGULATORS_AS_PI3K_TARGETS | 2.22 | 9.28E-07 |
| CROONQUIST_IL6_DEPRIVATION_DN | 2.04 | 7.30E-06 |
| CROONQUIST_NRAS_SIGNALING_DN | 2.04 | 7.90E-06 |
| MONTERO_THYROID_CANCER_POOR_SURVIVAL_UP | 2.12 | 3.12E-05 |
| ZHAN_MULTIPLE_MYELOMA_PR_UP | 2.09 | 1.18E-05 |

Fig 11B(1)

| | | A |
|---|---|---|
| LY_AGING_MIDDLE_DN | 2.07 | 3.44E-05 |
| YU_MYC_TARGETS_UP | 2.04 | 5.71E-06 |
| REACTOME_APCDC20_MEDIATED_DEGRADATION_OF_CYCLIN_B | 2.01 | 1.09E-06 |
| REACTOME_CYTOSOLIC_TRNA_AMINOACYLATION | 2.01 | 1.01E-05 |
| REACTOME_FORMATION_OF_TUBULIN_FOLDING_INTERMEDIATES_BY_CCT_TRIC | 2.01 | 1.30E-05 |
| REACTOME_INACTIVATION_OF_APC_VIA_DIRECT_INHIBITION_OF_THE_APCOMPLEX | 2.01 | 2.87E-06 |
| REACTOME_MRNA_SPLICING_MINOR_PATHWAY | 2.01 | 8.69E-07 |
| REACTOME_PHOSPHORYLATION_OF_THE_APC | 2.01 | 167E-06 |
| REACTOME_UNWINDING_OF_DNA | 2.05 | 5.64E-06 |
| REACTOME_VIRAL_MESSENGER_RNA_SYNTHESIS | 2.02 | 1.81E-06 |
| Endpoint vs. Rebound | | |
| REACTOME_CLASSICAL_ANTIBODY_MEDIATED_COMPLEMENT_ACTIVATION | 0.49 | 5.57E-05 |
| EGUCHI_CELL_CYCLE_RB1_TARGETS | 2.09 | 2.37E-05 |
| MATHEW_FANCONI_ANEMIA_GENES | 2.01 | 5.55E-07 |
| KUMAMOTO_RESPONSE_TO_NUTLIN_3A_DN | 2.00 | 5.99E-05 |
| REICHERT_G1S_REGULATORS_AS_PI3K_TARGETS | 2.00 | 6.10E-06 |
| HOFMANN_MYELODYSPLASTIC_SYNDROM_HIGH_RISK_UP | 2.05 | 3.24E-06 |
| MONTERO_THYROID_CANCER_POOR_SURVIVAL_UP | 2.12 | 3.04E-05 |
| GLINSKY_CANCER_DEATH_UP | 2.06 | 3.15E-05 |
| LY_AGING_MIDDLE_DN | 2.06 | 4.00E-05 |

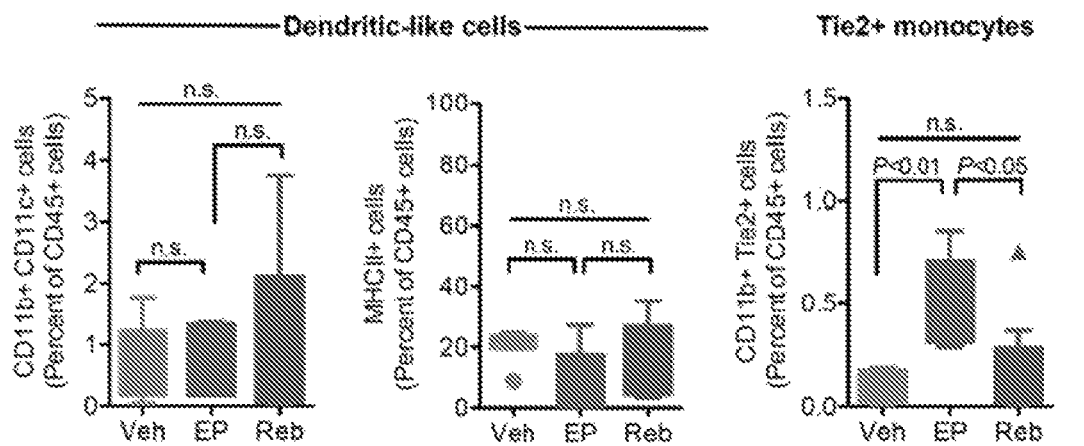
Fig. 15C  Fig. 15D
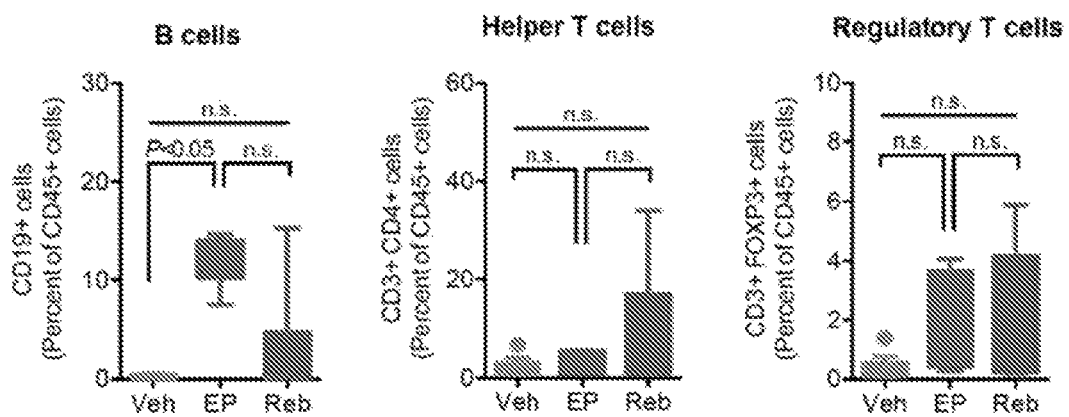
Fig. 15E  Fig. 15F  Fig. 15G

COMPOSITIONS AND METHODS FOR TREATMENT OF GLIOMA

This application is a U.S. National Stage entry under 35 U.S.C. § 371 of International Patent Application No. PCT/US2016/031431, filed May 9, 2016, which claims the benefit of priority of U.S. Provisional Patent Application No. 62/158,671, filed on May 8, 2015, the content of which is hereby incorporated by reference in its entirety.

STATEMENT OF GOVERNMENT SUPPORT

This invention was made with government support under grant number CA181355 awarded by the National Institutes of Health. The government has certain rights in the invention.

INCORPORATION BY REFERENCE

For countries that permit incorporation by reference, all of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention.

BACKGROUND

Glioblastoma multiforme (GBM) is the most common and highly aggressive primary brain tumor, representing approximately 50% of all brain tumors. With standard of care therapy, which currently includes surgery, radiation, and temozolomide chemotherapy, patient prognosis is poor with an average survival of 12-15 months. Despite a clear and urgent need to improve treatment options for patients, most therapies aimed at directly targeting glioma cells in GBM have failed, largely due to substantial genetic and tumor cell heterogeneity, and a high propensity for recurrence.

As an alternative to tumor-targeted therapy, targeting the tumor microenvironment (TME) has been shown to be an effective therapeutic strategy in several tumor types, including brain tumors. Brain-resident and bone marrow-derived tumor-associated macrophages (TAMs) are the predominant immune cell population in GBMs comprising up to 30% of the bulk tumor mass. In many types of cancer, including glioma, high TAM numbers are associated with high grade tumors and poor patient prognosis.

Macrophages depend on colony stimulating factor (CSF)-1 for their differentiation and survival, and thus strategies to target macrophages often include blockade of the CSF-1 receptor (CSF-1R). It was previously shown that blocking CSF-1R with the compound BLZ945 in advanced, high-grade, gliomas resulted in rapid tumor de-bulking by more than 30% after just 7 days of treatment (Pyonteck et al., "CSF-1R inhibition alters macrophage polarization and blocks glioma progression;" Nat. Med. 2013 October; 19(10): pp. 1264-72). However, prior to the present invention the efficacy of CSF-1R inhibitors such as BLZ945 in longer-term treatment of high-grade glioma was unknown. Similarly, prior to the present invention it was not known whether longer-term treatment of GBM with CSF-1R inhibitors, such as BLZ945, might result in the emergence of drug resistance, and if so, what strategies might be available to ameliorate such drug resistance.

SUMMARY OF THE INVENTION

The present invention is based, in part, on a series of important discoveries relating to the use of CSF-1R inhibitors for the treatment of glioma. As described in more detail in the Examples section of this patent specification, it has now been discovered that, despite good short-term therapeutic effects, in approximately half of subjects the efficacy of CSF-1R inhibitor treatment is significantly reduced during longer-term treatment regimens, with significant tumor recurrence and the development of drug resistance. The studies presented herein found that, while during the initial stages of CSF-1R treatment gliomas regressed (i.e. there was a decrease in tumor volume), the gliomas then entered a period of dormancy (with no significant change in tumor volume), which was then followed by a period of recurrence or rebound during which gliomas significantly increased in size—despite continued CSF-1R inhibitor treatment. It was found that this acquired CSF-1R inhibitor resistance was mediated by elevated phosphatidylinositol 3-kinase ("PI3-kinase or "PI3K") signaling in the rebounding tumors, driven by a paracrine interaction between elevated insulin-like growth factor 1 ("IGF-1") produced by tumor-associated macrophages ("TAMs"), and elevated IGF-1 receptors ("IGF-1R") on the tumor cells. In particular, it was found that IGF-1 is upregulated in TAMs in response to IL4 secretion, in part via activation of NFAT and Stat6 signaling, and that the secreted IGF-1 results in activation of IGF-1R and PI3K signaling in glioma cells, supporting tumor growth and malignancy. Building on these discoveries, it was found that therapy with various different active agents acting at various steps in this signaling process (including IGF-1R inhibitors, PI3K inhibitors, NFAT inhibitors, and Stat6 inhibitors, or various combinations thereof) resulted in improved CSF-1R inhibitor sensitivity and significantly increased long-term survival. It was also found that treatment of naïve gliomas (i.e. gliomas that had not been treated with CSF-1R inhibitors) with some of these agents also resulted in a significant survival benefit—however, these effects were not as substantial as the survival benefits observed in rebound tumors following CSF-1R inhibition.

Accordingly, in some embodiments the present invention provides various methods useful for the treatment of glioma.

In some such embodiments such methods comprise administering to a subject in need thereof an effective amount of: a CSF-1R signaling pathway inhibitor (such as a CSF-1R inhibitor), and one or more agents selected from the group consisting of: an IGF-1/IGF-1R signaling pathway inhibitor (such as an IGF-1R inhibitor), a PI3K signaling pathway inhibitor (such as a PI3K inhibitor), an IL4 inhibitor, an NFAT inhibitor, and a Stat6 inhibitor.

In other such embodiments such methods comprise administering to a subject an effective amount of: a CSF-1R signaling pathway inhibitor (such as a CSF-1R inhibitor), and two or more agents selected from the group consisting of: an IGF-1/IGF-1R signaling pathway inhibitor (such as an IGF-1R inhibitor), a PI3K signaling pathway inhibitor (such as a PI3K inhibitor), an IL4 inhibitor, an NFAT inhibitor, and a Stat6 inhibitor. In some such embodiments, the subject is treated by administering an effective amount of a CSF-1R signaling pathway inhibitor (such as a CSF-1R inhibitor), and an IGF-1/IGF-1R signaling pathway inhibitor (such as an IGF-1R inhibitor), and a PI3K signaling pathway inhibitor (such as a PI3K inhibitor). In other such embodiments, the subject is treated by administering an effective amount of a CSF-1R signaling pathway inhibitor (such as a CSF-1R inhibitor), and both an NFAT inhibitor and a Stat6 inhibitor.

In other embodiments the present invention provides methods for the treatment of glioma, such methods comprising administering to a subject in need thereof an effective amount of one or more agents selected from the group consisting of: an IGF-1/IGF-1R signaling pathway inhibitor (such as an IGF-1R inhibitor), a PI3K signaling pathway inhibitor (such as a PI3K inhibitor), an IL4 inhibitor, an NFAT inhibitor, and a Stat6 inhibitor.

Similarly, in some embodiments the present invention provides methods for the treatment of glioma, such methods comprising administering to a subject in need thereof an effective amount of two or more agents selected from the group consisting of: an IGF-1/IGF-1R signaling pathway inhibitor (such as an IGF-1R inhibitor), a PI3K signaling pathway inhibitor (such as a PI3K inhibitor), an IL4 inhibitor, an NFAT inhibitor, and a Stat6 inhibitor. In some such embodiments the present invention provides methods for the treatment of glioma comprising administering to a subject in need thereof an effective amount of both an IGF-1/IGF-1R signaling pathway inhibitor (such as an IGF-1R inhibitor), and a PI3K signaling pathway inhibitor (such as a PI3K inhibitor). Similarly, in other such embodiments the present invention provides methods for the treatment of glioma comprising administering to a subject in need thereof an effective amount of both an NFAT inhibitor and a Stat6 inhibitor.

In some embodiments the present invention provides pharmaceutical compositions, such as those that may be useful in the treatment of glioma.

In some such embodiments the pharmaceutical compositions comprise both a CSF-1R signaling pathway inhibitor (such as a CSF-1R inhibitor), and one or more additional agents selected from the group consisting of: an IGF-1/IGF-1R signaling pathway inhibitor (such as an IGF-1R inhibitor, a PI3K signaling pathway inhibitor (such as a PI3K inhibitor), an IL4 inhibitor, an NFAT inhibitor, and a Stat6 inhibitor.

In other such embodiments the pharmaceutical compositions comprise both a CSF-1R signaling pathway inhibitor (such as a CSF-1R inhibitor), and two or more additional agents selected from the group consisting of: an IGF-1/IGF-1R signaling pathway inhibitor (such as an IGF-1R inhibitor, a PI3K signaling pathway inhibitor (such as a PI3K inhibitor), an IL4 inhibitor, an NFAT inhibitor, and a Stat6 inhibitor. For example, in some such embodiments such compositions comprise a CSF-1R signaling pathway inhibitor (such as a CSF-1R inhibitor), and an IGF-1/IGF-1R signaling pathway inhibitor (such as an IGF-1R inhibitor), and a PI3K signaling pathway inhibitor (such as a PI3K inhibitor). In other such embodiments, the compositions comprise a CSF-1R signaling pathway inhibitor (such as a CSF-1R inhibitor), and both an NFAT inhibitor and a Stat6 inhibitor.

In other such embodiments the pharmaceutical compositions comprise two or more agents selected from the group consisting of: an IGF-1/IGF-1R signaling pathway inhibitor (such as an IGF-1R inhibitor), a PI3K signaling pathway inhibitor (such as a PI3K inhibitor), an IL4 inhibitor, an NFAT inhibitor, and a Stat6 inhibitor. In some such embodiments the pharmaceutical compositions comprise both an IGF-1/IGF-1R signaling pathway inhibitor (such as an IGF-1R inhibitor), and a PI3K signaling pathway inhibitor (such as a PI3K inhibitor). Similarly, in other such embodiments the pharmaceutical compositions comprise both an NFAT inhibitor and a Stat6 inhibitor.

Suitable inhibitors (such as CSF-1R inhibitors, IGF-1R inhibitors, PI3K inhibitors, IL4 inhibitors, NFAT inhibitors, and Stat6 inhibitors) that can be used in accordance with the methods and compositions of the present invention are known in the art and are described in the Detailed Description and Examples sections of this patent application. In some embodiments the inhibitors used are able to cross the blood-brain barrier, such that they may be administered to a subject systemically (for example via oral administration or intravenous administration). However, in some embodiments the inhibitors may not be able to cross the blood-brain barrier, or may have limited ability to cross the blood-brain barrier. In such embodiments, intracranial (e.g. intracerebral) administration may be used.

The present invention contemplates several different treatment regimens for administration of the various different inhibitors/active agents described herein. For example, in some embodiments administration of an IGF-1/IGF-1R signaling pathway inhibitor (such as an IGF-1R inhibitor), PI3K signaling pathway inhibitor (such as a PI3K inhibitor), IL4 inhibitor, NFAT inhibitor, or Stat6 inhibitor is commenced approximately concurrently with administration of the CSF-1R inhibitor—without waiting for the development of dormancy or subsequent CSF-1R resistance.

However, in other embodiments the administration of an IGF-1/IGF-1R signaling pathway inhibitor (such as an IGF-1R inhibitor), PI3K signaling pathway inhibitor (such as a PI3K inhibitor), IL4 inhibitor, NFAT inhibitor, or Stat6 inhibitor is commenced subsequent to the commencement of CSF-1R inhibitor treatment, for example when the glioma is no longer regressing, or is dormant, or is rebounding/recurring, and/or has developed CSF-1R resistance.

In those embodiments that involve administration of IGF-1/IGF-1R signaling pathway inhibitors (such as IGF-1R inhibitors), PI3K signaling pathway inhibitors (such as PI3K inhibitors), IL4 inhibitors, NFAT inhibitors, or Stat6 inhibitors without CSF-1R inhibitor treatment, such inhibitors may be administered alone, or in conjunction with other non-CSF-1R-inhibitor agents, and treatment may be commenced on naïve tumors (e.g. tumors that have not yet been treated with another agent), or may be commenced after the tumor has been treated with other agents, for example after treatment with another agent has been commenced but the glioma is no longer regressing, or is dormant, or is rebounding/recurring, and/or has developed resistance to the other agent.

In some embodiments the methods of the present invention may be used to treat subjects that have previously been treated with a CSF-1R inhibitor or other agent useful for the treatment of glioma, for example subjects having a glioma that was previously sensitive to CSF-1R inhibitor treatment (or treatment with another agent), but that is no longer responsive to such treatment. Similarly, in some embodiments the methods of the present invention may be used to treat subjects having a glioma that is not, or does not appear to be, sensitive to CSF-1R inhibitor treatment or treatment with another agent.

The methods and compositions provided herein are directed to the treatment of glioma. In some embodiments the glioma may be a glioblastoma, such as a proneural glioblastoma or Glioblastoma Multiforme (GBM). In some embodiments the glioblastoma may be an astrocytoma or an oligodendroglioma.

A variety of subjects may be treated with the methods and compositions of the present invention. In some embodiments the subject is a mammal, for example a rodent (e.g. a mouse, rat, or guinea pig), a non-human primate, or a human. In addition to the specific treatment methods of the invention, subjects may also be treated using other treatment regimens known to be useful in the treatment of glioma, including, but not limited to, surgical methods (e.g. tumor resection surgery), radiation therapy, chemotherapy (for example using temozolomide), or anti-angiogenic therapy (for example using bevacizumab).

These and other embodiments are described in more detail elsewhere in this patent application, including in the Figures, Brief Description of the Figures, Detailed Description, and Examples sections of this patent application. Furthermore, it should be understood that variations and combinations of each of the embodiments described throughout this patent application are contemplated and are intended to fall within the scope of the present invention.

BRIEF DESCRIPTION OF THE FIGURES

FIG. 1A—Long-term trial design for testing BLZ945 efficacy in a PDGF-B-driven glioma (PDG) model. High-grade PDG tumors were treated with BLZ945 (200 mg/kg/d) or vehicle (20% captisol) and monitored by biweekly MM for up to 26 weeks (defined endpoint; see methods) or until symptomatic. FIG. 1B—Tumor volume curves from biweekly MRIs of long-term BLZ945 trials (n=90 animals treated, 23 representative curves are shown). Four key phases are indicated, including 7d (regressing tumor), 28d (dormant tumor), rebound (Reb; recurrent tumor, evaluated on a mouse-to-mouse basis by MM), and endpoint (EP; stable regression at the 26-week endpoint). FIG. 1C—Waterfall plots showing percent change in tumor volume between 0-14d in a representative subset of animals from FIG. 1D (BLZ945 n=71; vehicle n=4). FIG. 1D—Kaplan-Meier of BLZ945-treated (n=90) versus vehicle-treated (n=30) mice bearing high-grade PDG tumors (Log-rank Mantel-Cox test, P<5×10-17). Median survival for vehicle-treated animals was 15d post-treatment initiation, while median survival for BLZ945-treated animals was 93d. FIG. 1E—Representative MM images over time of one mouse with a rebounded tumor (top row), and another mouse that had stable disease until EP (bottom row).

FIG. 2A—Gene set variation analysis based on RNA-seq from FACS-purified EP and Reb tumor cells (PDGFRα+; see FIG. 11B). Circles to the right of the "enriched in rebound" line indicate gene sets significantly enriched in Reb tumor cells, while circles to the left of the "enriched in endpoint" line identify those enriched in EP tumor cells. The PI3K gene set is indicated with an arrow. Vertical lines indicate fold cutoff for significance (n=5-6 samples per group). FIG. 2B—Immunoblot from snap-frozen Veh, EP and Reb tumors demonstrating elevated phospho (p)-AKT in Reb tumors compared to Veh and EP (n=3 experiments, one representative blot is shown). FIG. 2C—Long-term trial design for evaluating BLZ945 and BKM120 combination therapy on PDG tumors. High-grade tumors were treated with BLZ945 until recurrent tumors developed (trial design 1) or until dormancy (28d, trial design 2), whereupon BKM120 was either added (with continuous BLZ945 treatment) or switched (discontinued BLZ945). FIG. 2D—Survival of animals with recurrent tumors treated either with BLZ945 alone (n=33), BKM120 alone (n=9), or BLZ945 in combination with BKM120 (n=16; trial design 1 in FIG. 2C). Combination of BLZ945+BKM120 led to an increase in overall survival (Log-rank Mantel-Cox test, P<0.0001), and in median survival (51d) following recurrence compared to BLZ945 (13d) or BKM120 (10d) monotherapy. FIG. 2E—Survival of animals with 28d dormant tumors treated either with BLZ945 alone (n=90; same cohort as presented in FIG. 1D), BKM120 alone (n=9), or BLZ945 in combination with BKM120 (n=11; trial design 2 in FIG. 2C). Combination of BLZ945+BKM120 led to increased overall survival compared to either monotherapy. Log-rank Mantel-Cox test was used to calculate significance. FIG. 2F—Average percent change in tumor volume (0-14d) between vehicle- or BLZ945-treated tumors, in 3 different RCAS-PDGFB-HA Nestin-Tv-a GBM models (termed PDG, p53 knockdown (KD), and Pten knockout (KO) here; see methods). BLZ945 efficacy in the p53 KD model (BLZ945 n=8 mice; vehicle n=6 mice) was comparable to the PDG model (BLZ945 n=71 mice; vehicle n=4 mice) after 2 weeks (56% and 62% volume reduction, respectively); however, BLZ945 efficacy was less pronounced in the Pten KO model (n=5 mice per treatment group; 3% volume reduction). FIG. 2G—Average percent change in tumor volume (0-28d) between vehicle- or BLZ945-treated Pten KO tumors (n=5 mice per group). BLZ945 caused 11% volume reduction after 4 weeks. Data were analyzed by Student's t-test unless indicated otherwise.

FIG. 3A—Quantification of bioluminescent imaging (BLI) from intracranially transplanted 52Reb cells into naïve mice. Results show that 52Reb cells, isolated from a recurrent PDG tumor that developed resistance to BLZ945 treatment in vivo, re-establish sensitivity to BLZ945 in the naïve setting (Student's t-test d15, P<0.05, n=10 mice). Representative BLI images at d15 are shown. FIG. 3B—Left: H&E of a rebound tumor (T) adjacent to glial scarring (S). Scale bar=500 μm. Right: Representative regions of calcification (top), reactive astrocytic barrier (middle), and recurrent tumor (bottom). Scale bars=50 μm. FIG. 3C—H&E, Von Kossa and GFAP staining on rebound tissue. Scale bars=200 μm, except GFAP 20×=50 μm as indicated. FIG. 3D—Allred score for the astrocyte marker GFAP, showing a higher intensity and proportion of GFAP+ staining in Reb tissues (n=8 mice) compared to other treatment groups (n=5 mice per group). FIG. 3E—Flow cytometry of TAMs (CD45+CD11b+Gr1−) in Veh, 28d, EP and Reb tumors (n=5-7). Data were analyzed by a one-way ANOVA and Tukey's multiple comparisons test. FIG. 3F—Heatmap showing RNA-seq expression changes via qRT-PCR of M2-like associated genes in Veh, EP and Reb TAMs (n=5-6 per group). Wound-associated genes are indicated in bold with asterisks.

FIG. 4A-G. IL4 activates wound-associated genes in rebound TAMs and is produced by T cells in the rebound tumor microenvironment. FIG. 4A—Spectrum model of macrophage activation using gene set enrichment analysis (GSEA) of transcriptional programs regulated by the indicated cytokines (see methods). Reb TAMs exhibit activation of programs driven by TGFβ1 and IL4 compared to Veh TAMs (n=5 per group). The −log 10 (P-value) is plotted for each gene set (0, 4, 8, 12, and >16 radially outward in grey concentric circles). The black line indicates a −log 10 (P-value) cutoff of 3. FIG. 4B—GSEA as in (A), confirming that Reb TAMs exhibit activation of programs driven by IL4 and TGFβ1 compared to EP TAMs (n=5-6 per group). Dotted line demarcates P<0.05. FIG. 4C—qRT-PCR analysis demonstrates that IL4 induces expression of the wound-associated genes Retnla, Chil3 and Ccl17 in bone marrow-derived macrophages (BMDMs) in culture, while recombinant TGFβ1 treatment does not. Bone marrow isolate was obtained from 5 or more independent WT mice for replicate experiments. FIG. 4D—qRT-PCR analysis of Il4 expression in snap frozen whole-tumor samples from Veh, EP or Reb treatment groups, demonstrating elevated expression in the Reb setting (n=4 tumors) compared to both Veh (n=4 tumors) and EP (n=4 tumors). FIG. 4E—Flow cytometry of total CD3+ T cells (n=5-10) and (F) CD3+ CD8+ cytotoxic T cells (n=5-10) in Veh, EP and Reb tumors. FIG. 4G—RNA-seq data from a panel of cell types (GFAP+ astrocytes, CD19+ B cells, CD3+ CD8+ cytotoxic T cells (Tc), and remaining CD3+ CD8− bulk T cells) isolated from rebound tumors by FACS (n=3,). Results show elevated Il4 expression in bulk T and Tc cells, and Il13 expression in bulk T cells. Significance values for C-F were calculated by one-way ANOVA and Tukey's multiple comparisons test.

FIG. 5A-I. The IGF-1/IGF-1R axis is induced in rebound gliomas. FIG. 5A—Volcano plot showing the fold change (log 2(fold)) between Reb (n=5) and EP (n=6) TAMs on the x-axis and the significance (−log 10(P-value)) on the y-axis. Dots the upper right quadrant indicate genes upregulated in Reb TAMs, while dots in the upper left quadrant indicate genes downregulated in Reb TAMs. Igf1 is labeled in the upper right quadrant. FIG. 5B—RNA-seq barplot depicting Igf1 transcripts per million (TPM) in Veh, EP and Reb TAMs (n=5-6 per group; one-way ANOVA and Tukey's multiple comparisons). FIG. 5C—RNA-seq barplot depicting Igf1r TPM in Veh, EP and Reb tumor cells (n=5-6 per group; one-way ANOVA and Tukey's multiple comparisons). FIG. 5D—Quantification of immunofluorescent staining of phospho (p)-IGF-1R in Veh, 28d, EP and Reb tumor tissues. Results show pIGF-1R is elevated in rebound tumors compared to all other groups (n=5-8 per group; one-way ANOVA and Dunnett's multiple comparisons to Reb). FIG. 5E—MTT assay demonstrating higher sensitivity of an early-passage primary rebound PDG cell line (74Reb, triangles) to IGF-1R inhibition with OSI906 compared to a primary treatment-naïve PDG cell line (PDGC23, squares) (n=3, one representative experiment shown). IC50 values are indicated with arrows.

FIG. 5F—MTT proliferation assays of 74Reb cells (left) compared to PDGC23 cells (right), treated with conditioned media (CM) from BMDMs that were stimulated with rebound glioma microenvironment culture CM (see FIGS. 16, I and J for details). Stimulated BMDM CM (Stim CM) induced growth of 74Reb cells more than PDGC23 cells (130% versus 58%, respectively), and this effect was blocked with an anti-IGF-1 neutralizing antibody (n=4 replicate experiments). A one-way ANOVA and Dunnett's multiple comparisons to Stim CM+PBS was used to calculate differences at 5d (P<0.0001 for all). FIG. 5G—Correlation between IGF1 and CSF1R or MRC1 expression from TCGA-GBM data. FIG. 5H—Single sample GSEA for a hallmark PI3K signature was used to assign a pathway activity score (see methods) across patients from the TCGA-GBM dataset. PI3K signature scores were then correlated with IGF1 expression levels as shown. FIG. 5I—Linear regression analysis of immunohistochemical staining for phospho (p)-AKT and MRC1 in serial sections from GBM patient tissue (n=18 patients). A significant correlation between MRC1 protein levels and AKT signaling was observed. For correlational analyses (G-I), a Spearman coefficient was used to assess significance, and a line of best fit is shown (dashed lines). The 95% confidence band (outer dashed lines) is also shown in (I).

FIG. 6A-G. NFAT and Stat6 cooperate to regulate Igf1 expression in rebound TAMs. FIG. 6A—Transcription factor (TF) network analysis from RNA-seq data showing enriched TF families (squares) connected with a line to target genes (circles). White circles indicate genes targeted by multiple TFs. FIG. 6B—Predicted NFAT TF activity in Veh, EP and Reb TAMs, showing a high score specifically in Reb TAMs (n=5-6 per group). FIG. 6C—qRT-PCR analysis of Igf1 in BMDMs derived from WT, Stat6−/− or Il4ra flox; LysM-cre mice, treated +/− recombinant mouse IL4 (10 ng/ml; n=5 independent experiments). Student's t-test was used for pairwise comparisons within each genotype. FIG. 6D—qRT-PCR analysis of Igf1 in BMDMs derived from WT mice, treated +/− recombinant mouse IL4 (10 ng/ml), a Stat6 inhibitor (AS1517499, 50 nM) and/or an NFAT inhibitor (INCA-6, 40 μM; n=6 independent experiments). A one-way ANOVA and Dunnett's multiple comparisons to the +IL4 condition was used to calculate significance. FIG. 6E—Survival of PDG animals with high-grade tumors treated first with BLZ945 alone until dormancy (28d), and then enrolled on combination therapy with either AS1517499 (n=10), FK506 (NFAT inhibitor; n=17), or EtOH vehicle control (n=9). Combination therapy with either inhibitor led to a significant increase in overall survival (FK506=82% survival P<0.0001; AS1517499=50% survival P<0.05), compared to vehicle control (22% survival). Log-rank Mantel-Cox test was used to calculate significance. FIG. 6F—Survival curve representing animals with recurrent tumors treated either with continuous BLZ945 alone (n=33) or BLZ945+AS1517499 (n=9). Combination therapy led to a significant increase in overall survival (Log-rank Mantel-Cox test, P<0.05), and in median survival following recurrence (45d) compared to BLZ945 monotherapy (13d). FIG. 6G—qRT-PCR analysis of Igf1, CD36, Arg1 and Mrc1 levels in a subset of animals from (F). Results show a significant reduction of Igf1 expression in rebound tumors following Stat6 inhibition (n=5 per group, P<0.01), and a reduction of known IL4-Stat6 transcriptional targets (CD36 P<0.05; Arg1 P<0.05; Mrc1 P<0.01), confirming drug efficacy in the brain (n=5 for all, Mann-Whitney test).

FIG. 7A—Long-term trial design for testing BLZ945 and OSI906 combination therapy on PDG tumors. High-grade tumors were treated with BLZ945 until recurrent tumors developed (trial design 1) or until dormancy (28d, trial design 2), whereupon OSI906 was either added (with continuous BLZ945) or switched (discontinued BLZ945). FIG. 7B—Survival of animals with recurrent tumors treated either with BLZ945 alone (n=33), OSI906 alone (n=13), or BLZ945 in combination with OSI906 (n=13; trial design 1 in FIG. 7A). Combination therapy of BLZ945+OSI906 led to an increase in overall survival (Log-rank Mantel-Cox test, P<0.001), and in median survival following recurrence (63d) compared to BLZ945 (13d), or OSI906 (12d) monotherapy. FIG. 7C—Ki67:CC3 (cleaved caspase 3) proliferation:apoptosis index from immunofluorescent staining of recurrent tumors treated with BLZ945 alone versus BLZ945+OSI906 for 2 weeks (Mann-Whitney test, P<0.01, n=7-8 mice). FIG. 7D—Representative H&E and immunofluorescent images corresponding to data in (C). Scale bars=50 μm. FIG. 7E—Bioluminescent imaging (BLI) from orthotopically xenografted patient-derived tumorspheres (TS573) that were subject to 24d of treatment with BLZ945 (lower/dotted line) versus vehicle control (upper/solid grey line). The dashed line extending from the lower dotted line after the arrow indicating addition of OS1906 is data obtained with BLZ945+vehicle, while the solid line extending from the lower dotted line after the arrow indicating addition of OS1906 is data obtained with BLZ945+OSI906. Results demonstrate that treatment with BLZ945+OSI906 blunts outgrowth of rebound tumors compared to BLZ945+ vehicle. Mann-Whitney test was used to calculate P-values for each time point (n=5-20 mice). FIG. 7F—Ki67:CC3 index from immunofluorescent staining of TS573 orthotopic xenograft tissues (Mann-Whitney test, P<0.01, n=5 mice per group). FIG. 7G—Kaplan-Meier analysis of PDG animals treated either with BLZ945 alone (n=90; same cohort as presented in FIG. 1D), OSI906 alone (n=6) or with BLZ945 in combination with OSI906 during dormancy (n=9; trial design 2 in FIG. 7A). Combination therapy of BLZ945+ OSI906 extended overall survival compared to either monotherapy. Log-rank Mantel-Cox test was used to calculate significance. FIG. 7H—BLI of orthotopically xenografted U251 cells genetically engineered to express an IGF1R-targeted doxycycline (dox)-inducible shRNA (sh; n=15-16 mice; bottom 2 lines) or a scrambled control vector (Scr; n=4-5 mice; upper two lines). Arrows indicate respective administration of dox. Graph shows two combined shRNAs; data for individual hairpins are shown in FIG. 21E. Mann-Whitney test was used to calculate significance.

FIG. 9A-F. Gliomas that acquire resistance to CSF-1R inhibition are high-grade and highly proliferative. FIG. 9A—Comparison of tumor volumes (mm3) by MII at the time of trial enrollment between vehicle- and BLZ945-treated animals (corresponding to animals presented in FIG. 1C). Starting tumor volume at the time of enrollment was ≥2 mm3, as measured by MM, in all cases. Results demonstrate that vehicle-treated tumors (n=4 representative mice) were significantly smaller at 0d compared to BLZ945-treated tumors (n=71 representative mice; Mann-Whitney test, P<0.05), yet animals still died significantly earlier in survival trials. FIG. 9B—Representative immunofluorescent staining for phospho (p)-CSF-1R in tumors from vehicle-treated mice, or tumors from BLZ945-treated mice that developed recurrence. Images show that CSF-1R phosphorylation is efficiently decreased in BLZ945-resistant rebound tumors. Scale bar=50 μm. FIG. 9C—H&E images of vehicle (Veh), 7d, 28d, endpoint (EP), and rebound (Reb) tumors compared to adjacent normal brain tissue. The diffuse and aggressive growth pattern of rebound tumors is evident (lower right). Scale bar=50 μm. FIG. 9D—Histological grading demonstrates that BLZ945 treatment reduces tumor grade over time, while the majority of rebound tumors are grade III. Lesions that were classified as "residual" showed a histological response, characterized by pronounced tumor cell depopulation. Veh, 7d and 28d n=6, EP n=10, Reb n=8. FIG. 9E—Average tumor volume (mm3) by MM in vehicle (n=8 mice) versus rebound (n=33 mice) tumors at the time of sacrifice (n.s.=non-significant). FIG. 9F—Immunostaining for Ki67 and cleaved caspase 3 (CC3) was performed on Veh, 7d, 28d, EP and Reb tissue sections, and proliferation:apoptosis (Ki67:CC3) indices were calculated (see methods) and graphed on a log scale. Results confirm histologically that tumors categorized as regressing or dormant by MII have a ratio <1, whereas vehicle and rebound tumors have a ratio >>1 (n=7-12 mice per group). Data were analyzed by Student's t-test unless indicated otherwise. Where relevant, Tukey's outliers are shown as points on the box plot graphs and are included in statistical comparisons.

FIG. 11 A-H. Pharmacological blockade of PI3K efficiently targets rebound tumors. FIG. 11B—Gene Set Variation Analysis (GSVA) was performed on Veh, EP, and Reb tumor cell samples. Nominal P-values and fold changes are shown for each comparison. Significant differentially enriched gene sets were identified with a fold change of >2 or <0.5, and a false discovery rate of 10%. Data were obtained from n=5-6 RNA-seq samples per group.

FIG. 12A-I. The tumor microenvironment supports acquired resistance to BLZ945 treatment. FIG. 12A—MTT proliferation assays show that viability of primary cell lines generated from rebound PDG tumors (74Reb, 52Reb, 89BReb, 48Reb and 89AReb) is not directly affected by high BLZ945 concentrations (6,700 nM) in culture (n=3 replicate experiments). Axes are the same in each of the 5 panels (i.e. viability (fold) plotted against days in culture). FIG. 12B-D—Quantification of immunofluorescent staining of TAMs (CD68 and Iba1) in 52Reb (n=8 mice), 48Reb (n=7-8 mice), and 74Reb (n=8-10 mice) orthotopic transplantation trials. Similar to the PDG model, macrophage numbers are maintained in xenografts following BLZ945 treatment (Student's t-test, all non-significant). FIG. 12E-F—BLI measurements of intracranially transplanted rebound cell lines (48Reb n=9-10 mice; 74Reb n=8-9 mice) into naïve mice. Results show that rebound cells isolated from recurrent PDG tumors that were resistant to BLZ945 treatment in vivo re-establish sensitivity to BLZ945 in the naïve setting (Student's t-test at d15, P<0.05 in both cases). Representative BLI images of vehicle- and BLZ945-treated tumors on d15 are shown. FIG. 12G—Quantification of immunofluorescent staining for pimonidazole (PMO) demarcating regions of hypoxia in Veh, EP and Reb tumors. Rebound tumors show a significant increase in tissue hypoxia compared to EP tumors (n=4-6 mice per group; one-way ANOVA and Tukey's multiple comparisons, P<0.05). FIG. 12H—Quantification of immunofluorescent staining for CD31+ vessels in Veh, EP and Reb tumors. Both Reb and EP tumors have significantly fewer CD31+ cells compared to Veh tumors (n=4-5 mice per group; one-way ANOVA and Tukey's multiple comparisons, P<0.01). FIG. 12I—Quantification of the proportion of tumors that exhibit a scar phenotype, characterized by the presence of calcification, reactive astrocytes, and adjacent tumor outgrowth.

FIG. 13A-G. Quantification of immunofluorescent staining for CD68 (n=6-15 mice) or Iba1 (n=8-11 mice) in Veh, 28d, EP, and Reb tumors. Results corroborate those determined by flow cytometry in FIG. 3E, showing reduced numbers of macrophages in rebound tumors compared to other treatment groups. FIG. 13B—Gating strategy to assess the proportion of putative recruited BMDMs versus resident microglia in rebound tumors by flow cytometry, distinguished here by CD45 high versus CD45 low respectively (see methods). FIG. 13C—Proportion of CD45hi CD11b+ and CD45lo CD11b+ cells as a percent of total CD45+ events in Veh, EP and Reb tumors is depicted. Results show an enrichment for the CD45lo CD11b+ population after prolonged treatment with BLZ945 in both EP and Reb tumors compared to Veh tumors (n=5 per group). FIG. 13D—Representative flow cytometry plots corresponding to the data presented in FIG. 13C. FIG. 13E—Quantification of immunofluorescent staining for CD68 and Ki67 in Veh, EP and Reb tumors. Results show increased proliferation of CD68+ cells in rebound tumors (n=3-5 mice per group; n.s.=non-significant). FIG. 13F—Quantification of immunofluorescent staining for CD206 and Ki67 in Veh, EP and Reb tumors. Results show increased proliferation of CD206+ cells in rebound tumors (n=3-4 mice per group). FIG. 13G—Representative immunofluorescence image of a rebound tumor co-stained for CD206 and Ki67, showing rare but detectable double-positive cells. Scale bar=50 μm. Data were analyzed by Student's t-test unless indicated otherwise.

FIG. 14A—Principal component analysis was used to visualize global gene expression correlations among Veh (left dots), EP (middle dots) and Reb (right dots) TAMs, based on RNA-seq results from FACS-purified Gr1-CD11b+ cells (see methods; n=5-6 per group). The first component represents 20.6% of the variance, the second component represents 12.9% of the variance, and the third component represents 8.5% of the variance. FIG. 14B—RNA-seq scatterplots depicting Retnla, Chil3 and Ccl17 transcripts per million in 28d TAMs vs Reb TAMs. No significant differences were found (n=3-4 per group). FIG. 14C—RNA-seq barplots depicting Il4ra and Tgfbr1 transcripts per million in Veh, EP and Reb TAMs and tumor cells (n=5-6 per group). FIG. 14D—qRT-PCR analysis demonstrating that the TGFβ-type 1 receptor inhibitor SB431542 does not alter baseline expression of Retnla, Chil3 or Ccl17 expression in bone marrow-derived macrophages (BMDMs) in culture. SB431542 was used to account for any potential autocrine TGFβ1 signaling in BMDMs. Bone marrow isolate was obtained from 5 or more independent mice for replicate experiments. FIG. 14E—Quantification of immunofluorescent staining for phosphorylated (p)-Stat6 in Veh, 28d, EP, and Reb tumors, demonstrating significantly elevated signaling in the Reb setting compared to all other treatment groups as indicated (n=3-8 mice per group). FIG. 14F—Representative immunofluorescence images of Veh, 28d, EP, and Reb tumors stained for p-Stat6 (red), corresponding to data presented in FIG. 14E. Scale bar=50 μm. Data were analyzed by Student's t-test unless indicated otherwise.

FIG. 15A-I. Immuno-profiling of BLZ945-resistant tumors. FIG. 15A-G—Flow cytometry analysis of (FIG. 15A) CD11b+Ly6G+ neutrophils (n=5-8 mice per group), (FIG. 15B) CD11b+Ly6C+ monocytes (n=5-8), (FIG. 15C) CD11b+ CD11c+ (n=5-8) and MHCII+ cells (n=5-10), (FIG. 15D) CD11b+ Tie2+ monocytes (TEMs) (n=5-8), (FIG. 15E) CD19+ B cells (n=4-6), (FIG. 15F) CD3+ CD4+ helper T cells (n=5-10), and (FIG. 15G) CD3+ FOXP3+ regulatory T cells (n=5-10) in Veh, EP and Reb tumors. Mann-Whitney test was used to calculate P-values as indicated (n.s.=non-significant). FIG. 15H—RNA-seq expression data from a panel of different cell types (GFAP+ astrocytes, CD19+ B cells, CD3+ CD8+ cytotoxic T cells (Tc), and remaining CD3+ CD8- bulk T cells; n=3) isolated from rebound tumors by FACS. Results show high fidelity of sort purity, whereby cell-specific markers are appropriately enriched. FIG. 15I—qRT-PCR analysis of IL4 (upper panel) and IL13 (lower panel) across a panel of human cell lines, including B cells, monocyte subsets, T cell subsets, eosinophils, granulocytes, neutrophils, NK cells, macrophages (all isolated from donor human buffy coats; n=3 independent blood collections), human astrocytes, human brain microvascular cells, HUVECs (primary human cell lines; n=3 different passages), and the human glioma cell lines U251 and TS573 (n=3 different passages). In this human cell panel, IL4 was expressed at detectable levels in CD8+ T cells, as well as in monocytes, eosinophils, astrocytes, and brain microvascular cells, potentially explaining our xenograft results where T and B cells are absent in the NOD/SCID model. All human qRT-PCR was normalized to the HPRT1 housekeeping gene.

FIG. 16A—RNA-seq scatterplots depicting Igf1 transcripts per million in 28d TAMs vs Reb TAMs (n=3-4 per group; P<0.01). FIG. 16B—Volcano plot showing the fold change (log 2) between Reb and EP TAMs on the x-axis and the significance (−log 10 (P-value)) on the y-axis. Significant differentially expressed IL4-responsive genes (see methods) are shown in red, with Igf1 labeled in the upper right quadrant (n=5-6 per group). FIG. 16C—Representative immunofluorescence images showing elevated phosphorylated (p)-IGF-1R in rebound tumors, corresponding to data presented in FIG. 5D. Scale bar=50 µm. FIG. 16D—Left: Representative immunoblots from snap-frozen Veh, EP and Reb tumors demonstrating elevated p-IGF-1R in Reb tumors compared to Veh and EP. Total IGF-1R in Reb tumors shows a similar increase in protein expression levels as predicted from the RNA-seq analysis presented in FIG. 5C. Right: Quantitation of p-IGF-1R normalized to total IGF-1R in replicate immunoblots, representing n=3 mice per treatment group. Each replicate blot is represented by a different diamond on the graph. Within each set of replicates, Reb tumors had the highest level of p-IGF-1R in all cases. FIG. 16E—qRT-PCR analysis of Igf1 expression in snap frozen whole-tumor samples from Veh, EP or Reb treatment groups, demonstrating elevated expression in the Reb setting compared to both Veh (P<0.05) and EP tumors (P<0.05; n=4-6 per group). FIG. 16F—RNA-seq barplots depicting Igf1 and Igf1r transcripts per million in Veh, EP and Reb tumor cells and TAMs. FIG. 16G—Western blot of primary cell lines derived from dormant (28d) and rebound PDG tumors, demonstrating higher baseline p-AKT and p-IGF-1R in rebound lines. Furthermore, an inhibitor of IGF-1R (OSI906) effectively blocks p-IGF-1R and downstream p-AKT in both cases, confirming sensitivity to pharmacological inhibition. Three early passage replicates were used for each cell line ranging from passage 2-4 as indicated. FIG. 16H—MTT assays demonstrating higher sensitivity of an early-passage primary rebound PDG cell line (74Reb, triangles) to IGF-1R inhibition with AEW541, ADW742, or BMS754807 compared to a primary treatment-naïve PDG cell line (PDGC23, squares) (n=3, one representative experiment shown). IC50 values are indicated with arrows. FIG. 16I—Flow cytometry analysis of a panel of immune cell markers in primary glioma microenvironment cultures (GMECs) derived from rebound tumors, showing that a variety of different cell types are present at passage 1, including macrophages (CD11b+Gr1−), myeloid progenitors (CD11b+Gr1+), T cells (CD3+) and astrocytes (GLAST+), among others. FIG. 16J—Experimental design for the ex vivo GMEC experiments presented in FIG. 5F. Passage 1 GMECs were isolated from primary rebound tumors, and conditioned media was collected after 24 h. This media (GMEC CM) was used to stimulate a suspension culture of bone marrow-derived macrophages (BMDMs) from WT BL6 animals for 24 h. Conditioned media from these GMEC-stimulated BMDMs (Stim CM) was then collected and applied to either rebound tumor cells (74Reb) or naïve tumor cells (PDGC23), +/− a neutralizing antibody against IGF-1. An MTT proliferation assay was used to assess changes in growth over a 5d period, in response to each treatment condition. Data were analyzed by Student's t-test unless indicated otherwise.

FIG. 17A—Log 2 gene expression values were downloaded from the TCGA for GBM and are shown for the following genes: IGF1, CD163, MRC1, CSF1R, CD68, AIF1, GFAP and ALHD1L1. To determine whether IGF1 gene expression correlated with gene expression markers of macrophages (CD163, MRC1, CSF1R, CD68, and AIF1) or astrocytes (GFAP and ALDH1A1), we assessed pairwise correlations with a Spearman correlation test. The Spearman correlation, r, and corresponding P-values are shown for each comparison. Each column indicates the gene expression shown on the x-axis, and each row indicates the gene shown on the y-axis. A line of best fit is shown. FIG. 17B—Representative immunohistochemical images corresponding to data presented in FIG. 5I, showing staining for phospho (p)-AKT and MRC1 (scale bar=500 µm). FIG. 17C—qRT-PCR analysis of IGF1 expression in a panel of human cell types, including B cells, classical and non-classical monocytes, CD8+ T cells, Tregs, eosinophils, granulocytes, neutrophils, NK cells, macrophages (all derived from human donor buffy coats; n=3 blood collections), human astrocytes, human endothelial cells (including brain microvascular cells and HUVECs; n=3 different passages), and human glioma cell lines (TS573 and U251 cells; n=3 different passages). Results show the highest level of IGF1 expression in macrophages. Expression was normalized to the HPRT1 housekeeping control gene. FIG. 17D—Log 2 gene expression values for IGF1 are plotted representing TAMs and the remaining tumor bulk (see methods). IGF1 is enriched in TAMs compared to the tumor bulk. FIG. 17E—IGF1 expression was evaluated across molecular subtypes—Classical (C; n=145 patients), Mesenchymal (M; n=157 patients), Neural (N; n=88 patients), and Proneural (P; n=138 patients)—in the TCGA-GBM cohort. Data were analyzed by one-way ANOVA and Tukey's multiple comparisons test. FIG. 17F—Kaplan Meier analyses of patient RNA-seq data from the TCGA filtered for those with updated clinical information from the Broad Firehose, demonstrating (left) no significant difference in overall survival in IGF1low versus IGF1high tumors when split by median expression, (middle) a significant difference in overall survival when comparing the top 10% of IGF1high patients (Log-rank Mantel-Cox test, P<0.017), and (right) no significant difference in overall survival when comparing the top 10% of AIF1high patients. Results suggest that the change in overall survival in IGF1high tumors is not simply a reflection of higher macrophage content.

FIG. 18A—Transcription factors (TFs) were ranked based on differential activity between Reb and EP TAMs (see methods). Seven TF families were identified that showed enriched activity in Reb TAMs compared to EP TAMs, including HSF1, RXR, MYF, EP300, HBP1/HMGB, NFAT and EVI1 families (indicated in red). Data corresponds to results shown in FIG. 6A. FIG. 18B—qRT-PCR analysis of Igf1 expression in BMDMs in response to treatment with either IL4 versus IL4+*INCA*-6 NFAT inhibitor (NFATi), or TGFβ1 versus TGFβ1+NFATi. IL4, but not TGFβ1, is able to induce Igf1 expression in BMDMs, and this effect is reduced by the NFATi (n=6 replicate experiments; one-way ANOVA and Tukey's multiple comparisons test). FIG. 18C—qRT-PCR analysis of Retnla, Chil3 and Ccl17 in BMDMs derived from WT, Stat6−/− or Il4ra flox; LysM-cre mice, treated +/− recombinant mouse IL4 (10 ng/ml). Results show that IL4 treatment is able to induce expression of each of these genes in WT BMDMs, but not in the Stat6- or Il4ra-deficient BMDMs compared to (−) treatment controls (n=3-5 independent experiments; student's t-test was used for pairwise comparisons within each genotype). Note baseline levels of Chil3 were higher in Stat6- and Il4ra-deficient BMDMs compared to WT BMDMs. FIG. 18D—qRT-PCR analysis of Retnla, Chil3 and Ccl17 in BMDMs derived from WT mice, treated +/− recombinant mouse IL4 (10 ng/ml), a Stat6 inhibitor (AS1517499; 50 nM) and/or an NFAT inhibitor (*INCA*-6; 40 Results show that IL4 treatment is able to induce expression of each of these genes, and that expression is modulated by either or both inhibitors (n=6 independent experiments; one-way ANOVA and Dunnett's multiple comparisons to the +IL4 condition was used to calculate significance).

FIG. 19A—MTT proliferation assays on BMDMs treated with multiple inhibitors of IGF-1R (AEW541, ADW742, BMS754807 and OSI906) at increasing concentrations from 0-100 over the course of 3 days (n=7 independent experiments). BMDMs were least sensitive to OSI906 compared to other IGF-1R inhibitors, highlighting its potential for in vivo use as an IGF-1R inhibitor that preferentially targets tumor cells. FIG. 19B—Representative immunofluorescent staining for phospho (p)-IGF-1R in rebound tumors that were either treated with BLZ945 alone, or BLZ945+OSI906 combination therapy for 2 weeks. Images show reduced p-IGF-1R after treatment with BLZ945+OSI906. Scale bar=50 µm. FIG. 19C—Individual tumor volumes by MM of rebound tumors treated for two weeks with BLZ945+OSI906 versus BLZ945 alone. Results demonstrate the rapid progression of rebound tumors two weeks post-diagnosis (Reb versus 2 wk: n=26 mice, P<0.001), compared to the stasis/regression that is achieved with BLZ945+OSI906 combination therapy (Reb versus 2 wk: n=14 mice, non-significant). Data were analyzed by Student's t-test. FIG. 19D—Long-term trial design for testing OSI906 monotherapy on treatment-naïve PDG tumors. High-grade tumors were treated with OSI906 (40 mg/kg/d) or vehicle (25 mM tartaric acid) and monitored by biweekly MIll up to 26 wk (defined endpoint; see methods) or until symptomatic. FIG. 19E—Kaplan-Meier analysis of animals with treatment-naïve PDG tumors treated with OSI906 (n=16 mice), or vehicle control (25 mM Tartaric acid; n=13 mice). OSI906 as a single agent on treatment-naïve animals results in a significant though modest survival benefit compared to vehicle control (median survival post-treatment initiation 12d versus 20d; Log-rank Mantel-Cox test, P<0.05).

FIG. 20A—Schematic of combination trial design with BLZ945+OSI906 in orthotopic xenograft models, incorporating regular non-invasive bioluminescent imaging (BLI). FIG. 20B—BLI measurements from orthotopically xenografted human U251 cells that were subject to 24d of treatment with BLZ945 (dotted line to left of arrow) versus vehicle control (upper/solid line). Once BLZ945-treated tumors reached 3× the volume of their lowest BLI measurement (arrow), mice were randomly assigned to BLZ945+OSI906 (solid line to right of arrow) or BLZ945+vehicle (dashed line to right of arrow) treatment groups. Results demonstrate that the combination of BLZ945+OSI906 blunts the outgrowth of rebound tumors compared to BLZ945+vehicle controls. A Mann-Whitney test was used to calculate P-values for each time point. FIG. 20C—Quantification of immunofluorescent staining for Ki67:CC3 ratios, Iba1, and CD68 in U251 orthotopic xenograft trials as shown in FIG. 20B (n=5-9 tumors per group; n.s.=non-significant). FIG. 20D—Quantification of immunofluorescent staining for Iba1 and CD68 in TS573 orthotopic xenograft trials as shown in FIG. 7E (n=5 tumors per group). FIG. 20E—Quantification of immunofluorescent staining for CD206 in TS573 and U251 orthotopic xenograft trials (corresponding to FIG. 7E and FIG. 20B), demonstrating elevated M2-associated protein levels in vehicle-treated and rebound tumors, which is reduced in rebound tumors by the addition of OSI906 (n=3-4 mice). A panel of representative immunofluorescence images are also presented (lower panel). FIG. 20F—Quantification of immunofluorescent staining for phospho (p)-IGF-1R in TS573 and U251 orthotopic xenograft trials (corresponding to FIG. 7E and FIG. 20B), demonstrating elevated signaling in rebound tumors, which is reduced by the addition of OSI906 (n=4-5 mice). Representative immunofluorescent images are presented (lower panel). Data were analyzed by Student's t-test unless indicated otherwise.

FIG. 21A—Schematic of orthotopic xenograft trials with doxycycline (dox)-inducible IGF1R hairpins (TRIPZ backbone; see methods), incorporating bioluminescent imaging (BLI) every 3 days. FIG. 21B—Western blot validation of dox-inducible IGF1R shRNAs in U251 cells. FIG. 21C—Representative immunofluorescent images of orthotopically xenografted human U251 cells expressing two independent dox-inducible shRNAs against IGF1R. In both cases, a positive signal was observed for the dox-inducible RFP reporter in +Dox treatment groups. FIG. 21D—BLI measurements from U251 tumors expressing a dox-inducible Scramble shRNA control vector. Animals were enrolled into either Vehicle (upper two lines) or BLZ945 (lower two lines) treatment groups, in combination with either dox chow (solid line) or normal chow (dashed line; n=4-5 per group). With a control TRIPZ hairpin, BLZ945 treatment initially reduced tumor growth, but tumors eventually rebounded, as in FIG. 7E and FIG. 20B. FIG. 21E—BLI measurements from U251 tumors expressing IGF1R shRNA 1 (upper) or 2 (lower). In both cases, BLZ945 treatment (-dox) initially blunted tumor progression, but tumors eventually rebounded after 12d of treatment (shRNA 1 n=19 mice; shRNA 2 n=17 mice), recapitulating results from U251 trials in FIGS. 20B and 21D. When dox treatment was added at 12d to induce expression of the IGF1R hairpins (black arrow; continued BLZ945 treatment), rebound tumor growth was blunted (solid line; shRNA 1 n=9 mice; shRNA 2 n=7 mice) compared to -dox controls (hatched line; shRNA 1 n=9 mice; shRNA 2 n=6 mice). Mann-Whitney test was used to calculate P-values for each time point.

DETAILED DESCRIPTION

Figure 1A:
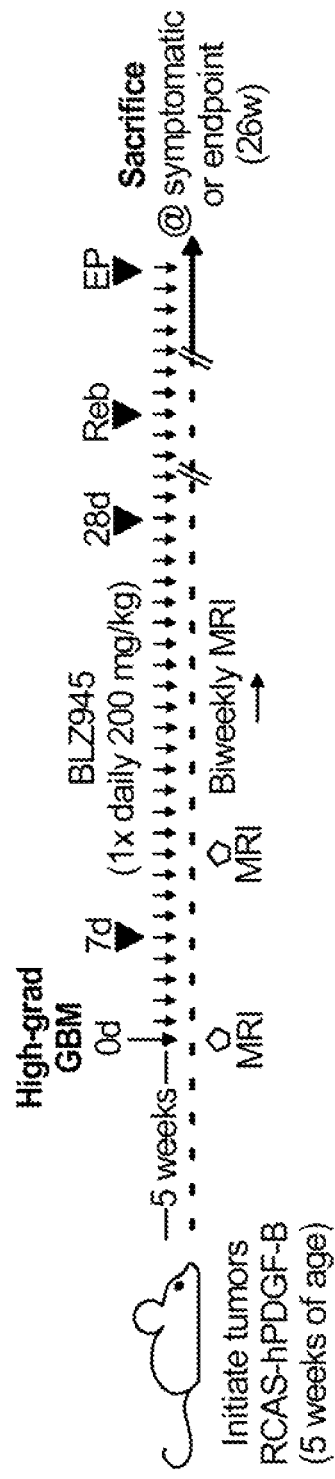
FIG. 1A-E. 56% of GBMs develop resistance to CSF-1R inhibition in long-term preclinical trials.

Some of the main embodiments of the present invention are described in the above Summary of the Invention section of this patent application, as well as in the Figures, Brief Description of the Figures, Examples, and Claims sections of this application. This Detailed Description section provides certain additional description relating to the compositions and methods of the present invention, and is intended to be read in conjunction with all other sections of the present patent application. The sub-headings provided below, and throughout this patent disclosure, are not intended to denote limitations of the various aspects or embodiments of the invention, which are to be understood by reference to the specification as a whole.

Definitions & Abbreviations

As used in this specification and the appended claims, the singular forms "a," "an," and "the" include plural referents, unless the context clearly dictates otherwise. The terms "a" (or "an") as well as the terms "one or more" and "at least one" can be used interchangeably Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Units, prefixes, and symbols are denoted in their Système International de Unites (SI) accepted form unless otherwise stated. Numeric ranges provided herein are inclusive of the numbers defining the range. Where a numeric term is preceded by "about," the term includes the stated number and values ±10% of the stated number.

The acronym "CSF-1" refers to colony stimulating factor 1. The acronym "CSF-1R" refers to the CSF-1 receptor.

The acronym "PI3K" refers to phosphatidylinositol 3-kinase.

The acronym "IGF-1" refers to insulin-like growth factor 1. The acronym "IGF-1R" refers to the IGF-1 receptor.

The acronym "IL4" refers to interleukin 4.

The acronym "NFAT" refers to nuclear factor of activated T-cells—a family of transcription factors.

The acronym "Stat6" refers to signal transducer and activator of transcription 6—a member of the Stat family of transcription factors.

An "active agent" is an agent (e.g. a small molecule, or a protein/peptide (such as an antibody)), for example as described and/or claimed herein, that has the recited activity—such as CSF-1R signaling pathway inhibitory activity, IGF-1/IGF-1R signaling pathway inhibitory activity, PI3K signaling pathway inhibitory activity, IL4 inhibitory activity, NFAT inhibitory activity, or Stat6 inhibitory activity. "Active agents" include, but are not limited to, the specific inhibitors described in this patent disclosure. It is also contemplated that, in each of the embodiments of the present patent disclosure that involve use of specified active agents, analogues, variants, or derivatives of each of such specified active agents can be used. One of skill in the art can readily determine whether an analogue, variant, or derivative of any of such specified active agent is suitable for use in accordance with the compositions and methods of the present invention, for example based on whether the analogue, variant, or derivative has one or more of the desired activities, such as, for example, CSF-1R inhibitory activity, IGF-1R inhibitory activity, PI3K inhibitory activity, IL4 inhibitory activity, NFAT inhibitory activity, and/or Stat6 inhibitory activity.

As mentioned above, in some embodiments active agents can be antibodies. The term "antibody," as used herein, encompasses intact polyclonal antibodies, intact monoclonal antibodies, antibody fragments (such as Fab, Fab', F(ab')2, and Fv, and single chain Fv (scFv) fragments, single-domain antibodies (sdAb or nanobodies)), fusion proteins comprising an antigen determination portion of an antibody, bispecific antibodies generated from at least two intact antibodies, chimeric antibodies, humanized antibodies, human antibodies, and any other modified immunoglobulin molecule(s) comprising an antigen recognition site—so long as the antibodies have the desired and/or recited biological activity—such as CSF-1R inhibitory activity, IGF-1R inhibitory activity, PI3K inhibitory activity, L4 inhibitory activity, NFAT inhibitory activity, and/or Stat6 inhibitory activity. Various different types of antibody fragments, and methods of making and using such antibody fragments, are known in the art. See, for example, Fridy et al., Nature Methods. 2014 December; 11(12):1253-60 (the contents of which are hereby incorporated by reference) for a description of the production of nanobody repertoires multi-specific antibodies. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well-known subunit structures and three-dimensional configurations. Antibodies can be naked, or conjugated to other molecules such as toxins, radioisotopes, or any of the other specific molecules recited herein.

The terms "inhibit," "block," "reduce," and "suppress" are used interchangeably and refer to any statistically significant decrease in biological activity, including—but not limited to—full blocking of the activity.

Various other terms are defined elsewhere in this patent disclosure, where used. Furthermore, terms that are not specifically defined herein may be more fully understood in the context in which the terms are used and/or by reference to the specification in its entirety. Where no explicit definition is provided, all technical and scientific terms used herein have the meanings commonly understood by those of ordinary skill in the art to which this invention pertains.

CSF-1R Inhibitors

In certain embodiments the present invention provides methods for the treatment of gliomas that comprise administration of one or more CSF-1R signaling pathway inhibitors (such CSF-1R inhibitors). In certain other embodiments the present invention provides compositions comprising one or more CSF-1R signaling pathway inhibitors (such CSF-1R inhibitors). In some of such embodiments, any suitable CSF-1R signaling pathway inhibitor can be used. In some embodiments the suitability of a CSF-1R signaling pathway inhibitor for use in accordance with the methods of the present invention may be ascertained from the literature (for example from published studies demonstrating anti-tumor activity, such as anti-glioma activity), or may be ascertained by employing various assays for anti-tumor activity (such as anti-glioma activity), such as those described in the Examples section of the present patent application. Several CSF-1R inhibitors that are known in the art can be used in conjunction with the present invention. For example, in some embodiments, any one or more of the following CSF-1R inhibitors (or classes of inhibitors) may be used: BLZ945, GW2580, ABT-869 (Linifanib), OSI-930, CEP-32496, AC708, PLX3397, AZD6495, CYC10268, IMC-CS4, RG7115, pyridyl bisamides, thiazolyl bisamides, 6-O-substituted benzoxazoles, and 6-O-substituted benzothiazoles. In some embodiments, any suitable variant, analogue or derivative of any one of such CSF-1R inhibitors may be used. In some embodiments the CSF-1R inhibitor may be a small molecule, or an antibody, or any other suitable agent that has CSF-1R inhibitory activity. In some embodiments the CSF-1R inhibitor used is one that can permeate the blood-brain barrier. In some embodiments the CSF-1R inhibitor may be linked to, or capable or co-delivery with, another agent that can confer upon the CSF-1R inhibitor the ability to permeate the blood-brain barrier. In some embodiments, the CSF-1R inhibitor is one of those described in WO 2012/151541, WO 2007/121484, US 2015/0080556, US 2014/0336363, US 2014/0065141, US 2014/0057972, US 2013/0005949, US 2012/0225861, US 2010/0280006, US 2010/0261679, US 2010/0130490, US 2009/0054411, US 2008/0045528, or US 20040014774. In some embodiments, the CSF-1R inhibitor used is BLZ945, or an analogue, variant, or derivative thereof. BLZ945 (or 4-((2-(((1R,2R)-2-hydroxycyclohexyl)amino) benzo[d]thiazol-6-yl)oxy)-N-methylpicolinamide, CAS Registry No.: 953769-46-5) is an orally active, potent and selective CSF-1R inhibitor, which inhibits CSF-1R activity with an IC50 of 1 nM and is more than 1000-fold selective against its closest receptor tyrosine kinase homologs c-KIT and Platelet-derived Growth Factor Receptor beta (PDGFRb). See Pyonteck et al., "CSF-1R inhibition alters macrophage polarization and blocks glioma progression;" Nat. Med. 2013 October; 19(10):pp. 1264-72, the contents of which are hereby incorporated by reference.

IGF-1R Inhibitors

In certain embodiments the present invention provides methods for the treatment of gliomas that comprise administration of one or more IGF-1/IGF-1R signaling pathway inhibitors (such as IGF-1R inhibitors). In certain other embodiments the present invention provides compositions comprising one or more IGF-1/IGF-1R signaling pathway inhibitors (such as IGF-1R inhibitors). In some of such embodiments, any suitable IGF-1/IGF-1R signaling pathway inhibitor can be used. In some embodiments the suitability of an IGF-1R inhibitor for use in accordance with the methods of the present invention may be ascertained from the literature (for example from published studies demonstrating anti-IGF-1R activity), or may be ascertained by employing various assays for IGF-1R activity known in the art, or may be ascertained by employing one of the assays described in the Examples section of the present patent application to demonstrate improved anti-tumor activity when the IGF-1R inhibitor is employed in conjunction with a CSF-1R inhibitor. Several IGF-1R inhibitors that are known in the art can be used in conjunction with the present invention. For example, in some embodiments, any one or more of the following IGF-1R inhibitors (or classes of inhibitors) may be used: OSI906 (linsitinib), NVP-AEW541, GSK1904529A, NVP-ADW742, BMS-536924, picropodophyllin (PPP), GSK1838705A, AG-1024, PQ401, and BMS-754807. In some embodiments, any suitable variant, analogue or derivative of any one of such IGF-1R inhibitors may be used. In some embodiments the IGF-1R inhibitor may be a small molecule, or an antibody, or any other suitable agent that has IGF-1R inhibitory activity. In some embodiments the IGF-1R inhibitor used is one that can permeate the blood brain barrier. In some embodiments the IGF-1R inhibitor may be linked to, or capable or co-delivery with, another agent that can confer upon the IGF-1R inhibitor the ability to permeate the blood-brain barrier. In some embodiments, the IGF-1R inhibitor is one of those described in US 2009/0054508, US 2010/0226884 or US 2014/0086830. In some embodiments, the CSF-1R inhibitor used is OSI906 (CAS Registry No. 867160-71-2), or an analogue, variant, or derivative thereof. See Mulvihill et al. "Discovery of OSI-906: A Selective and Orally Efficacious Dual Inhibitor of the IGF-1 Receptor and Insulin Receptor;" Future Med. Chem. 2009 September; 1(6): pp. 1153-71, the contents of which are hereby incorporated by reference.

PI3K Inhibitors

In certain embodiments the present invention provides methods for the treatment of gliomas that comprise administration of one or more PI3K signaling pathway inhibitors (such as PI3K inhibitors). In certain other embodiments the present invention provides compositions comprising one or more PI3K signaling pathway inhibitors (such as PI3K inhibitors). In some of such embodiments, any suitable PI3K signaling pathway inhibitor can be used. In some embodiments the suitability of a PI3K inhibitor for use in accordance with the methods of the present invention may be ascertained from the literature (for example from published studies demonstrating anti-PI3K activity), or may be ascertained by employing various assays for PI3K activity known in the art, or may be ascertained by employing one of the assays described in the Examples section of the present patent application to demonstrate improved anti-tumor activity when the PI3K inhibitor is employed in conjunction with a CSF-1R inhibitor. Several PI3K inhibitors that are known in the art can be used in conjunction with the present invention. For example, in some embodiments, any one or more of the following PI3K inhibitors (or classes of inhibitors) may be used: BKM120 (NVP-BKM120, buparlisib), idelaisib, SAR245409, SAR245408, BYL-719, GDC-0980, GDC-0941, wortmannin, Ly294002, demethoxyviridin, perifosine, delaisib, PX-866, IPI-145, BAY 80-6946, BEZ235, RP6530, TGR1202, RP5264, SF1126, INK1117, palomid529, GSK1059615, ZSTK474, PWT33597, IC87114, TG100-115, CAL263, RP6503, PI-103, GNE-477, CUDC-907, and AEZS-136. In some embodiments, any suitable variant, analogue or derivative of any one of such PI3K inhibitors may be used. In some embodiments the PI3K inhibitor may be a small molecule, or an antibody, or any other suitable agent that has PI3K inhibitory activity. In some embodiments the PI3K inhibitor used is one that can permeate the blood brain barrier. In some embodiments the PI3K inhibitor may be linked to, or capable or co-delivery with, another agent that can confer upon the PI3K inhibitor the ability to permeate the blood-brain barrier. In some embodiments, the PI3K inhibitor used is BKM120 (CAS Registry No. 944396-07-0), or an analogue, variant, or derivative thereof.

IL4 Inhibitors

In certain embodiments the present invention provides methods for the treatment of gliomas that comprise administration of one or more IL4 signaling pathway inhibitors (such IL4 inhibitors). In certain other embodiments the present invention provides compositions comprising one or more IL4 signaling pathway inhibitors (such IL4 inhibitors). In some of such embodiments, any suitable IL4 signaling pathway inhibitor can be used. In some embodiments the suitability of an IL4 signaling pathway inhibitor for use in accordance with the methods of the present invention may be ascertained from the literature, or may be ascertained by employing various assays for anti-tumor activity (such as anti-glioma activity), such as those described in the Examples section of the present patent application. Several IL4 inhibitors that are known in the art can be used in conjunction with the present invention. In some embodiments, any suitable variant, analogue or derivative of any one of such IL4 inhibitors may be used. In some embodiments the IL4 inhibitor may be a small molecule, or an antibody, or any other suitable agent that has IL4 inhibitory activity. In some embodiments the IL4 inhibitor used is one that can permeate the blood-brain barrier. In some embodiments the IL4 inhibitor may be linked to, or capable or co-delivery with, another agent that can confer upon the IL4 inhibitor the ability to permeate the blood-brain barrier.

NFAT Inhibitors

In certain embodiments the present invention provides methods for the treatment of gliomas that comprise administration of one or more NFAT pathway inhibitors (such NFAT inhibitors). In certain other embodiments the present invention provides compositions comprising one or more NFAT pathway inhibitors (such NFAT inhibitors). In some of such embodiments, any suitable NFAT pathway inhibitor can be used. In some embodiments the suitability of an NFAT signaling pathway inhibitor for use in accordance with the methods of the present invention may be ascertained from the literature, or may be ascertained by employing various assays for anti-tumor activity (such as anti-glioma activity), such as those described in the Examples section of the present patent application. Several NFAT inhibitors that are known in the art can be used in conjunction with the present invention. For example, in some embodiments, any one or more of the following NFAT inhibitors (or classes of inhibitors) may be used: Met-Ala-Gly-Pro-His-Pro-Val-Ile-Val-Ile-Thr-Gly-Pro-His-Glu-Glu (i.e. VIVIT peptide, CAS registry number 249537-73-3), 11R-VIVIT peptide, FK506, and *INCA*-6. In some embodiments, any suitable variant, analogue or derivative of any one of such NFAT inhibitors may be used. In some embodiments the NFAT inhibitor may be a small molecule, or an antibody, or any other suitable agent that has NFAT inhibitory activity. In some embodiments the NFAT inhibitor used is one that can permeate the blood-brain barrier. In some embodiments the NFAT inhibitor may be linked to, or capable or co-delivery with, another agent that can confer upon the NFAT inhibitor the ability to permeate the blood-brain barrier.

Stat6 Inhibitors

In certain embodiments the present invention provides methods for the treatment of gliomas that comprise administration of one or more Stat6 pathway inhibitors (such Stat6 inhibitors). In certain other embodiments the present invention provides compositions comprising one or more Stat6 pathway inhibitors (such Stat6 inhibitors). In some of such embodiments, any suitable Stat6 pathway inhibitor can be used. In some embodiments the suitability of an Stat6 signaling pathway inhibitor for use in accordance with the methods of the present invention may be ascertained from the literature, or may be ascertained by employing various assays for anti-tumor activity (such as anti-glioma activity), such as those described in the Examples section of the present patent application. Several Stat6 inhibitors that are known in the art can be used in conjunction with the present invention. For example, in some embodiments, the Stat6 inhibitor AS1517499 may be used. In some embodiments, any suitable variant, analogue or derivative of any one of such Stat6 inhibitors may be used. In some embodiments the Stat6 inhibitor may be a small molecule, or an antibody, or any other suitable agent that has Stat6 inhibitory activity. In some embodiments the Stat6 inhibitor used is one that can permeate the blood-brain barrier. In some embodiments the Stat6 inhibitor may be linked to, or capable or co-delivery with, another agent that can confer upon the Stat6 inhibitor the ability to permeate the blood-brain barrier.

Methods of Treatment & Prevention

In certain embodiments the present invention provides methods for the treatment and/or prevention of gliomas in subjects in need thereof, such methods comprising administering to the subject an effective amount of certain active agents.

The term "glioma" is used herein in accordance with its normal usage in the art and includes a variety of different tumor types, including, but not limited to gliomas, glioblastoma multiforme (GBM), astrocytomas, and oligodendrogliomas.

As used herein, the terms "treat," "treating," and "treatment" encompass a variety of activities aimed at achieving a detectable improvement in one or more clinical indicators or symptoms associated with glioma. For example, such terms include, but are not limited to, reducing the rate of growth of a glioma (or of glioma cells, or of other cells within a glioma), halting the growth of a glioma (or of glioma cells, or of other cells within a glioma), causing regression of a glioma (or of glioma cells, or of other cells within a glioma), reducing the size of a glioma (for example as measured in terms of tumor volume or tumor mass), reducing the grade of a glioma, eliminating a glioma (or glioma cells, or other cells within a glioma), preventing, delaying, or slowing recurrence (rebound) of a glioma, improving symptoms associated with glioma, improving survival from glioma, inhibiting or reducing spreading of a glioma (e.g. metastases), and the like.

For each of the methods and compositions described herein that are directed to "treatment" of glioma, in some embodiments such methods and compositions can be employed for "prevention" of glioma. As used herein the terms "prevent" and/or "prevention" refer to prophylactic or preventative measures that prevent and/or slow the development of a glioma. Thus, those in need of prevention include those at risk of, or susceptible to, glioma. In certain embodiments, a glioma is successfully prevented according to the methods provided herein if the patient develops, transiently or permanently, e.g., fewer or less severe symptoms associated with the glioma, or a later onset of symptoms associated with the glioma, than a patient who has not been subject to the methods and/or compositions of the invention.

In certain embodiments the methods of treatment and/or prevention provided herein may be employed together with other glioma treatment and/or prevention methods, including, but not limited to, surgical methods (e.g. for tumor resection), radiation therapy methods, treatment with chemotherapeutic agents (e.g. temozolomide, carmustine (BCNU), or cisplatin), treatment with antiangiogenic agents (e.g. bevacizumab), or treatment with tyrosine kinase inhibitors (such as gefitinib or erlotinib). Similarly, in certain embodiments the methods of treatment and/or prevention provided herein may be employed together with procedures used to monitor disease status/progression, such as biopsy methods and diagnostic methods (e.g. MM methods or other imaging methods).

Subjects

The terms "subject," "individual," and "patient"—which are used interchangeably herein, are intended to refer to any subject, preferably a mammalian subject, and more preferably still a human subject, for whom therapy or prophylaxis desired. Mammalian subjects include humans, domestic animals, farm animals, sports animals, and zoo animals including, e.g., humans, non-human primates, dogs, cats, mice, rats, guinea pigs, and the like. In most of the embodiments of the present invention the subject has, or is suspected of having, a glioma—such as glioblastoma multiforme (GBM), an astrocytoma, or an oligodendroglioma.

Administration Routes

In carrying out the treatment and/or prevention methods described herein, any suitable method or route of administration can be used to deliver the active agents.

In some embodiments systemic administration may be employed. "Systemic administration" means that the active agent is administered such that it enters the circulatory system, for example, via enteral, parenteral, inhalational, or transdermal routes. Enteral routes of administration involve the gastrointestinal tract and include, without limitation, oral, sublingual, buccal, and rectal delivery. Parenteral routes of administration involve routes other than the gastrointestinal tract and include, without limitation, intravenous, intramuscular, intraperitoneal, intrathecal, and subcutaneous.

In some embodiments (including, but not limited to, those in which one or more of the agents used is not able to permeate the blood-brain barrier), local administration may be employed.

"Local administration" means that a pharmaceutical composition is administered directly to where its action is desired (e.g., at or near the site of a glioma), for example via intracranial (e.g. intracerebral) delivery, such as via direct intratumoral injection. For example, ins some embodiments pressure-driven infusion through an intracranial catheter, also known as convection-enhanced delivery (CED) may be used.

It is within the skill of one of ordinary skill in the art to select an appropriate route of administration taking into account the nature of the specific active agent being used and nature of the specific glioma to be treated.

Effective Amounts

As used herein the terms "effective amount" or "therapeutically effective amount" refer to an amount of an active agent as described herein that is sufficient to achieve, or contribute towards achieving, one or more desirable clinical outcomes, such as those described in the "treatment" and "prevention" descriptions above. An appropriate "effective" amount in any individual case may be determined using standard techniques known in the art, such as dose escalation studies, and may be determined taking into account such factors as the desired route of administration (e.g. systemic vs. intracranial), desired frequency of dosing, etc. Furthermore, an "effective amount" may be determined in the context of the co-administration method to be used. For example, rather than perform dosing studies using an IGF-1R inhibitor alone, or a PI3K inhibitor alone, dosing studies may be performed in conjunction with administration of a CSF-1R inhibitor, because, as described herein, the effects of such agents may be synergistic. One of skill in the art can readily perform such dosing studies to determine appropriate doses to use, for example using assays such as those described in the Examples section of this patent application—which involve administration of a CSF-1R inhibitor together with either an IGF-1R inhibitor or a PI3K inhibitor.

Pharmaceutical Compositions

In certain embodiments, the present invention provides compositions, for example pharmaceutical compositions. The term "pharmaceutical composition," as used herein, refers to a composition comprising at least one active agent as described herein, and one or more other components useful in formulating a composition for delivery to a subject, such as diluents, buffers, saline (such as phosphate buffered saline), cell culture media, carriers, stabilizers, dispersing agents, suspending agents, thickening agents, excipients, preservatives, and the like. "Pharmaceutical compositions" permit the biological activity of the active agent, and do not contain components that are unacceptably toxic to the living subject to which the composition would be administered.

Pharmaceutical compositions can be in numerous dosage forms, for example, tablet, capsule, liquid, solution, soft-gel, suspension, emulsion, syrup, elixir, tincture, film, powder, hydrogel, ointment, paste, cream, lotion, gel, mousse, foam, lacquer, spray, aerosol, inhaler, nebulizer, ophthalmic drops, patch, suppository, and/or enema. The choice of dosage forms and excipients will depends upon the active agent to be delivered and the specific disease or disorder to be treated or prevented, and can be selected by one of ordinary skill in the art without having to engage in any undue experimentation.

The present invention can be further understood a by reference to the following "Example"—which is non-limiting and provided for illustration purposes only. It will be apparent to those skilled in the art that many modifications, both to materials and methods, can be practiced without departing from the scope of the present disclosure.

EXAMPLE

Numbers in parentheses following text in this Example represent the numbered references provided in the Reference List that follows.

Therapies targeted against the tumor microenvironment (TME) represent a promising approach for treating cancer. This appeal arises in part from the decreased likelihood of acquired resistance through mutations in target TME cells, as is frequently observed with cancer cell-targeted therapies. As multiple TME-directed therapies are currently advancing through different clinical trials (1, 2), this necessitates an understanding of potential mechanisms of intrinsic or acquired resistance. This experiments presented herein address this issue by investigating whether resistance to a macrophage-targeted therapy emerges during the course of long-term trials in various preclinical models of high-grade glioma (glioblastoma multiforme; GBM).

GBM is the most common and aggressive adult primary brain tumor, and survival is only minimally prolonged by current standard of care treatment, including surgery, radiation and temozolomide chemotherapy (3). Accordingly, targeting the glioma TME is emerging as a promising alternative therapeutic strategy. In GBM, tumor-associated macrophages and microglia (TAMs) comprise up to 30% of the bulk tumor mass (4). In many cancers, including glioma, elevated TAM numbers are associated with high grade and poor patient prognosis (4-7). As such, targeting TAMs in GBM represents an attractive therapeutic approach.

Macrophages critically depend on colony stimulating factor-1 (CSF-1) for multiple functions; consequently, strategies to target TAMs often include CSF-1 receptor (CSF-1R) blockade (8-10). In clinical trials, several approaches to inhibit CSF-1R are currently being employed including antibodies and small molecules (7, 11, 12). However, the long-term effects of these agents on clinical outcome are still under evaluation, and thus gaining insight into potential mechanisms of drug resistance and/or inefficacy is now critical.

In the work described herein a potent and highly selective small-molecule CSF-1R inhibitor, BLZ945, as used. It has been shown that BLZ945 blocks early gliomagenesis, while short-term treatment of advanced, high-grade glioma causes robust tumor debulking after just 7 days (8). Interestingly, CSF-1R inhibition has no direct effect on glioma cell viability, as these cells do not express CSF-1R in the models used here. Instead, glioma TAMs remain abundant and become anti-tumorigenic in response to treatment, by downregulating markers of M2-like macrophage polarization/alternative activation and adopting a pronounced phagocytic phenotype (8). This example addresses the unanswered question of whether long-term CSF-1R inhibition in aggressive late-stage GBM has a sustainable anti-tumorigenic effect, or instead leads to acquired resistance.

A Subset of GBMs Develop Resistance to CSF-1R Inhibition in Long-Term Preclinical Trials The kinetics of GBM response to continuous long-term BLZ945 treatment was analyzed using a transgenic platelet-derived growth factor-driven glioma (PDG) model (RCAS-hPDGF-B/Nestin-Tv-a; Mk4a/Arf$^{-/-}$) (8, 13) (FIG. 1A). Two weeks into the trial maximal tumor regression was observed with an average volume reduction of 62% (FIGS. 1, B and C). At this time point, 8% of animals showed no evidence of residual tumor by MRI. By contrast, vehicle-treated tumors exhibited a 2522% increase in volume over the same period (FIG. 1C).

Figure 1B:
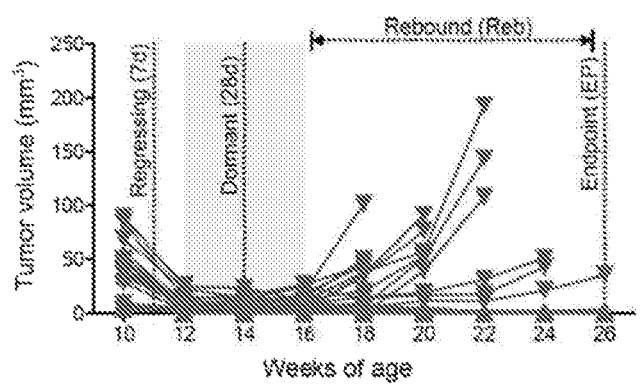
Figure 1C:
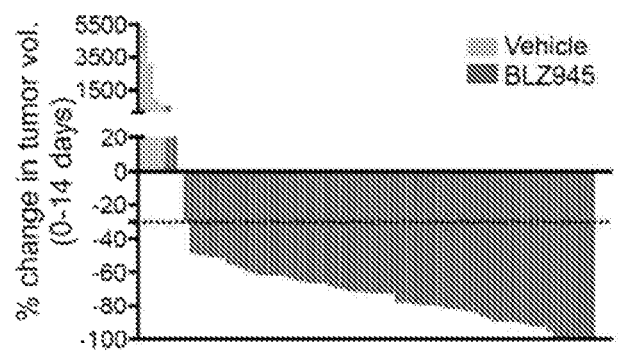
Figure 1D:
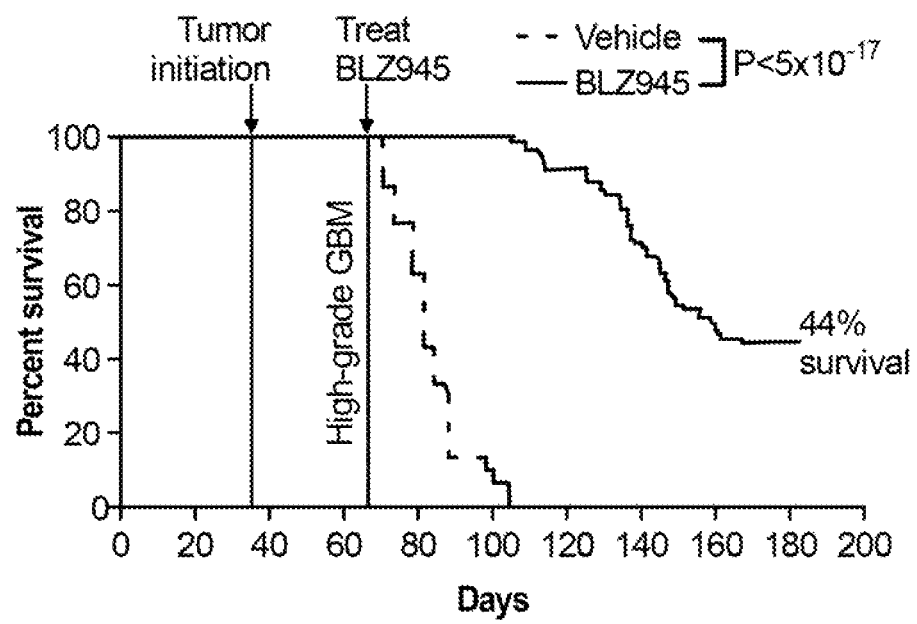
Figure 1E:
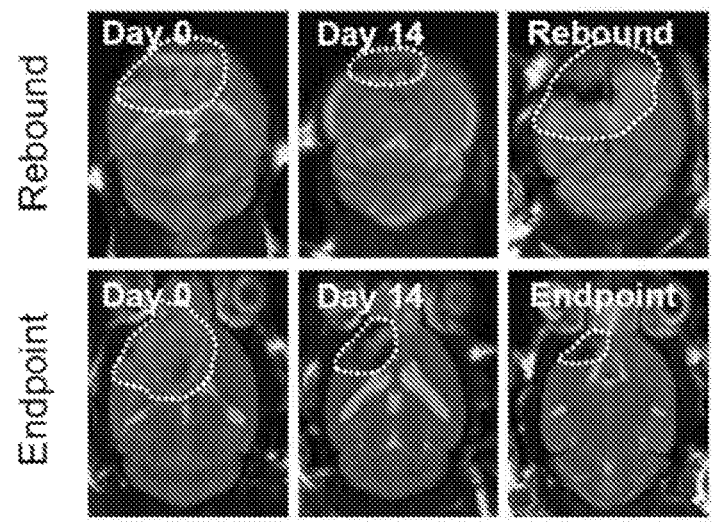
Figure 9A:
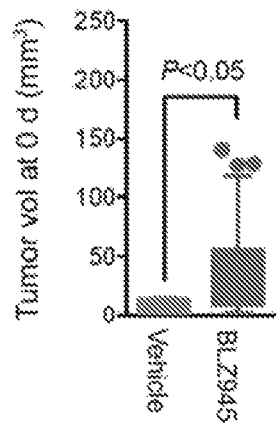
Figure 9B:
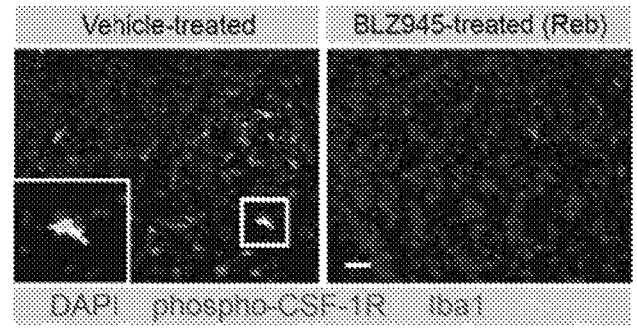

Following this regression phase, all BLZ945-treated tumors entered a dormancy phase, lasting for ≥4 weeks (FIG. 1B). 44% of treated animals remained symptom-free and survived to the trial endpoint of 26 weeks (FIG. 1D; P<5×10$^{17}$), with minimal or, in some cases, no evidence of residual tumor by MM and histology (FIG. 1E). This is in stark contrast to vehicle-treated GBMs, which were purposely selected to be smaller in size upon treatment initiation (FIG. 9A), yet median survival was only 15d post-treatment initiation (vs. 93d for BLZ945), and no animals survived beyond 6 weeks (FIG. 1D). Following the dormancy phase observed in all BLZ945-treated animals, however, 56% eventually developed resistance and tumors rebounded, despite effective, continued inhibition of CSF-1R phosphorylation in TAMs (FIGS. 1, B and D, and FIG. 9B).

Figure 9C:
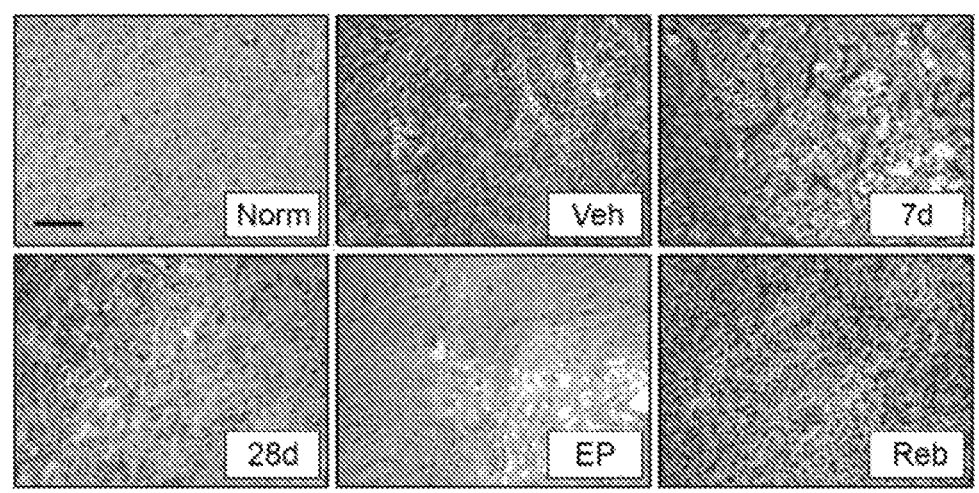

Experiments were performed to determine how this resistance to the CSF-1R inhibitor emerged, and several time points were chosen throughout the long-term trial for comparison, including Veh (vehicle; 20% Captisol until symptomatic), 7d (BLZ945-responsive, regressing), 28d (BLZ945-responsive, dormant), Reb (BLZ945-resistant, actively rebounding), and EP (26-week endpoint, stably regressed) (FIG. 1B). Histological analysis showed that after 7d of BLZ945, tumor grade was significantly reduced. At 28d and EP, histological grade remained low, with 33% and 50% of mice respectively showing no evidence of tumor by histology, and the remainder of animals exhibiting either residual disease or grade II tumors (FIGS. 9, C and D). By comparison, the majority of rebound tumors were grade III or IV, and similar in size to Veh tumors at sacrifice (FIG. 9, C to E). Both Veh and Reb tumors also exhibited a high proliferation: apoptosis index (Ki67: CC3) indicating a state of rapid growth (FIG. 9F).

Glioma Cells Resistant to CSF-1R Inhibition In Vivo Exhibit Elevated PI3K Signaling.

Figure 2A:
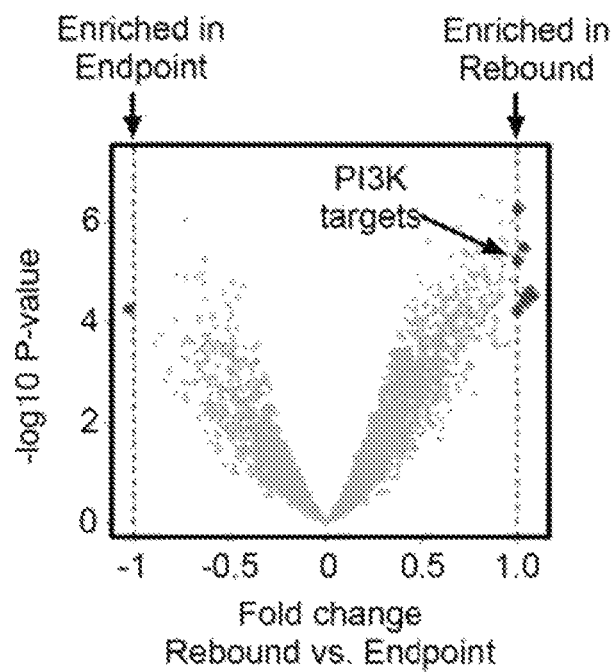
FIG. 2A-G. Combined CSF-1R and PI3K inhibition improves survival in the PDG model.
Figure 2B:
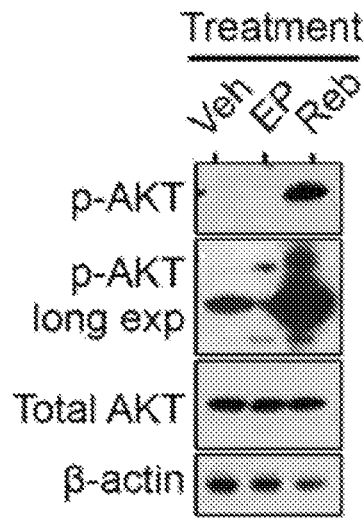
Figure 10A:
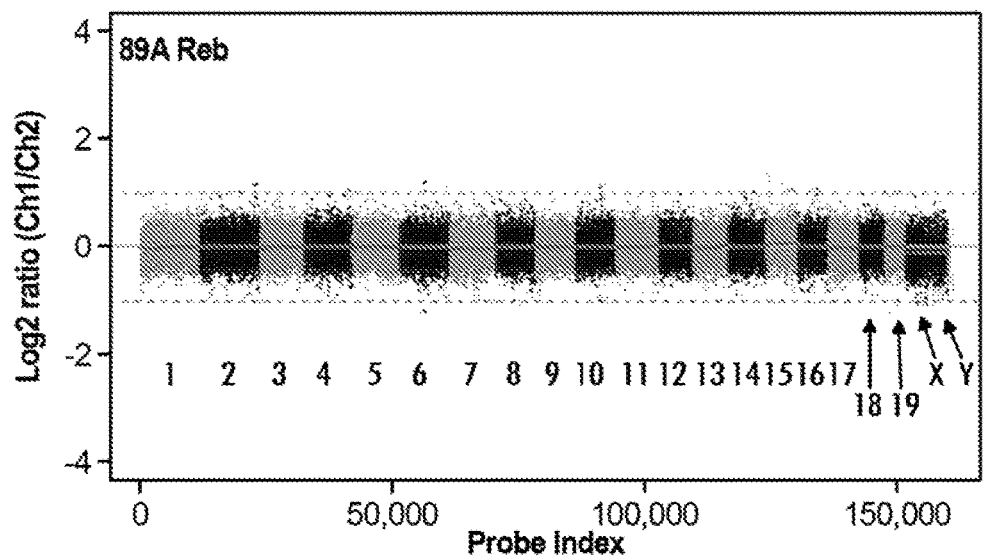
FIG. 10A-C. Array comparative genomic hybridization (aCGH) of primary rebound neurospheres. aCGH was performed on primary rebound neurospheres derived from BLZ945-resistant PDG tumors (passage 1). Three representative cell lines are shown, including (FIG. 10A) 89AReb, (FIG. 10B) 89BReb, and (FIG. 10C) 74Reb. In all cases, results showed no changes in copy number compared to reference DNA (liver from PDG mice).
Figure 10B:
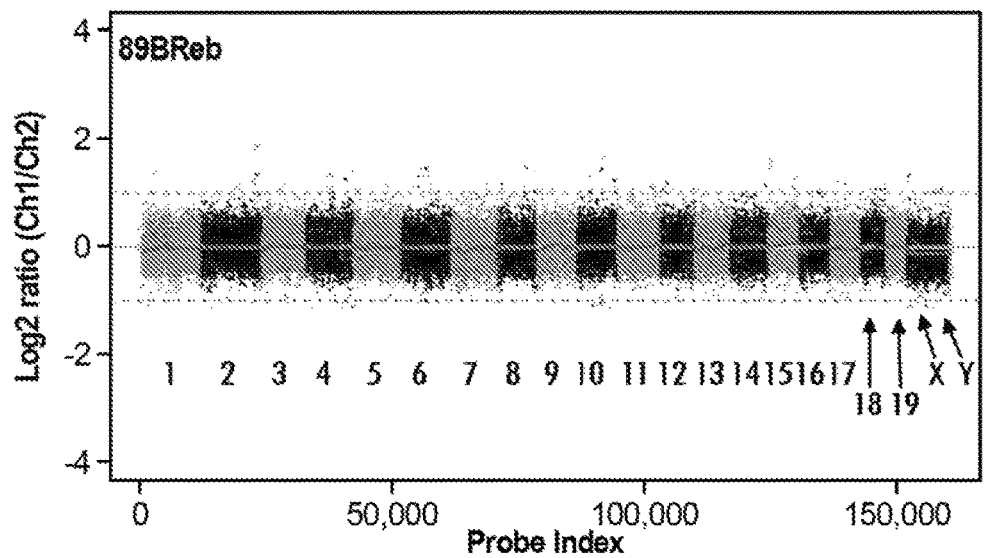
Figure 10C:
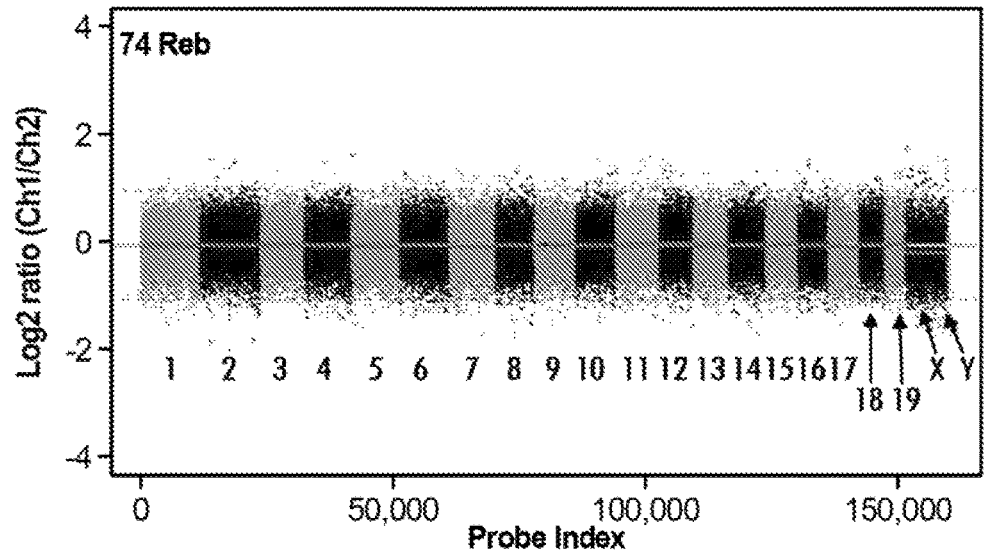

To determine the mechanism by which tumor cells acquire resistance, array comparative genomic hybridization (aCGH) analyses were performed and no copy number alterations were found in primary rebound glioma tumorsphere lines (passage 1; FIG. 10). To then assess which signaling pathways are altered specifically in recurrent tumors, glioma cells (PDGFRα$^+$) were first FACS-purified from Veh, EP and Reb lesions, and RNA-sequencing was performed. Glioma cells were isolated from EP lesions that were stably regressed, but still detectable by MM. Gene ontology analysis demonstrated that Veh and Reb tumor cells showed an enrichment of cell cycle-related genes, compared to EP tumor cells (FIG. 11A), corroborating the observed changes in Ki67 levels (FIG. S1F), and supporting the notion that EP tumors were in a state of cell cycle dormancy. To interrogate which pathways were differentially regulated between the three groups, gene set variation analysis (14) was used for each pair-wise comparison. Nine gene sets in total were significantly enriched in Reb tumor cells compared to EP (FIG. 11B), including a PI3K gene set (FIG. 2A), potentially explaining the robust differences in proliferation given the importance of PI3K signaling in cell cycle regulation. In accordance with this result, elevated phosphorylated (p)-AKT (a PI3K substrate) was found in Reb tissues compared to Veh and EP, using immunofluorescence staining and western blotting (FIG. 2B, and FIGS. 11, C and D).

Figure 11A:
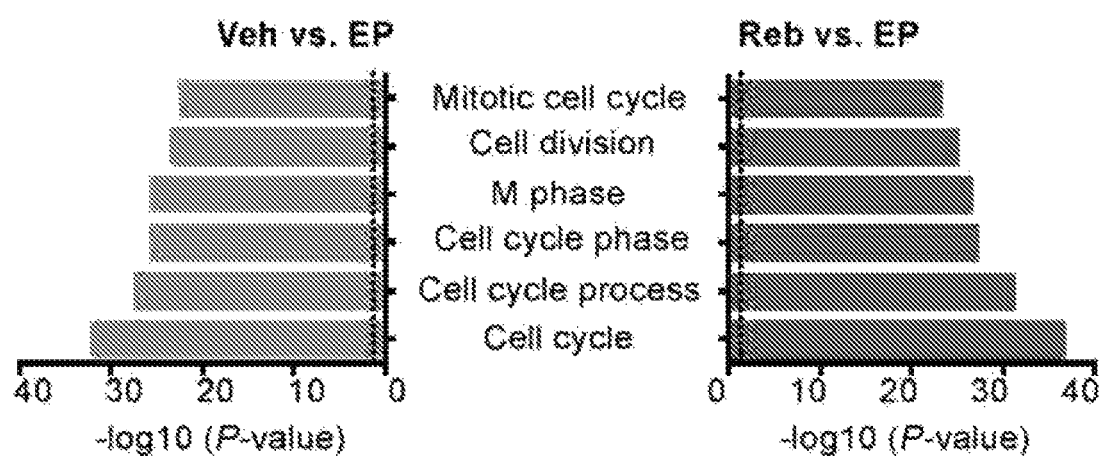
FIG. 11A—Gene ontology (GO) analyses were performed using DAVID to compare RNA-seq data from Veh versus EP tumor cells (left-hand bar plot), as well as Reb versus EP tumor cells (right-hand bar plot; n=5-6 per group; see methods). The y-axis depicts the top 6 significant GO terms for each comparison, and the x-axis depicts the –log 10 (P-value) for each term. Vertical dotted lines indicate significance cutoff (–log 10(0.05)=1.3).
Figure 11C:
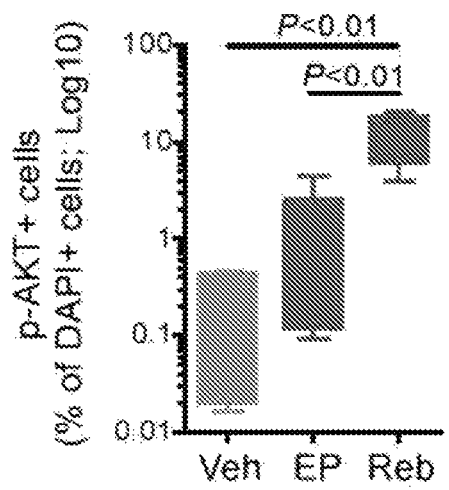
FIG. 11C—Quantification of immunofluorescent staining for phospho (p)-AKT in Veh, EP and Reb tissue samples (n=4-5).
Figure 11D:
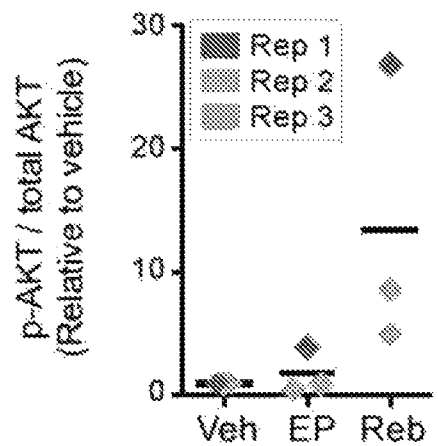
FIG. 11D—Quantitation of p-AKT normalized to total AKT in replicate immunoblots (see FIG. 2B for representative image), representing n=3 mice per treatment group. Each replicate blot is represented by a different diamond for each condition (Veh, EP, Reb) in the graph. Within each set of replicates, rebound (Reb) tumors had the highest level of p-AKT in all cases.
Figure 11E:
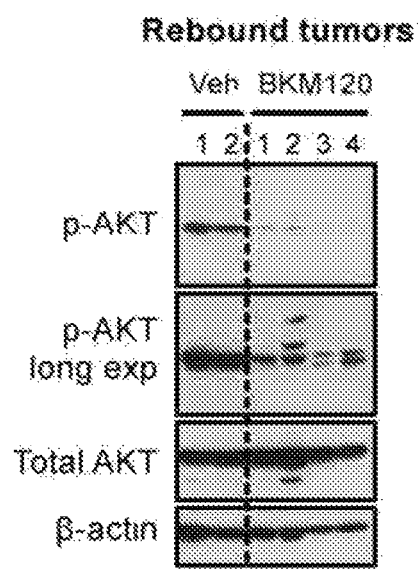
FIG. 11E—Western blot demonstrating reduced p-AKT in 4 representative BKM120-treated whole-tumor rebound samples compared to 2 representative vehicle-treated (NMP:PEG300) whole-tumor rebound samples. Results demonstrate target inhibition in the brain.
Figure 11F:
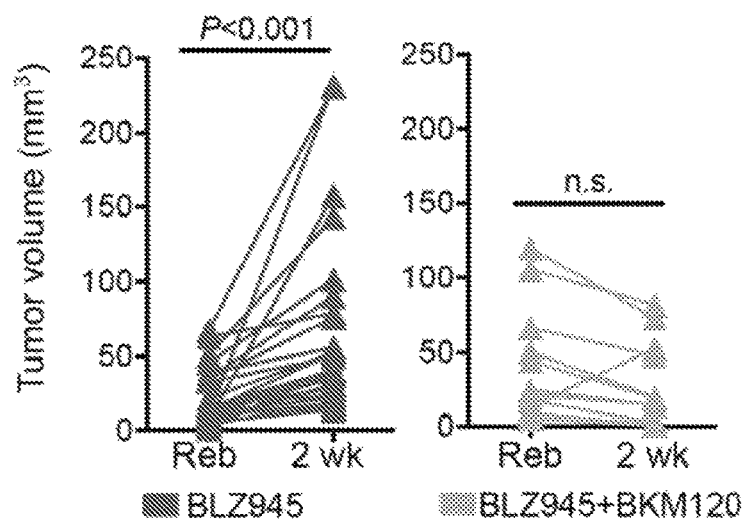
FIG. 11F—Individual tumor volumes by MM of rebound tumors treated for two weeks with BLZ945+ BKM120 versus BLZ945 alone. Results demonstrate the rapid progression of rebound tumors two weeks post-diagnosis (Reb versus 2 wk: n=26 mice, P<0.001), compared to the stasis/regression that is achieved with BLZ945+ BKM120 combination therapy (Reb versus 2 wk: n=11 mice, non-significant).
Figure 11G:
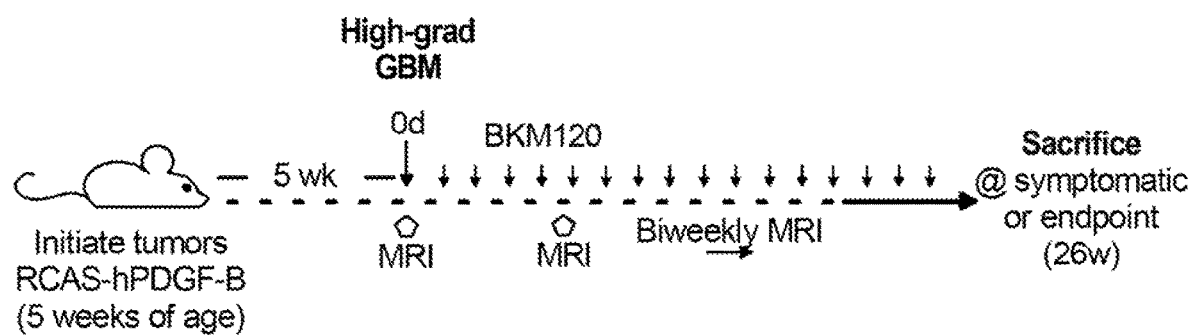
FIG. 11G—Long-term trial design for testing BKM120 monotherapy on treatment-naive PDG tumors. High-grade tumors were treated with BKM120 (20 mg/kg/d) or vehicle (NMP:PEG300) and monitored by biweekly MM up to 26 wk (defined endpoint; see methods) or until symptomatic.
Figure 11H:
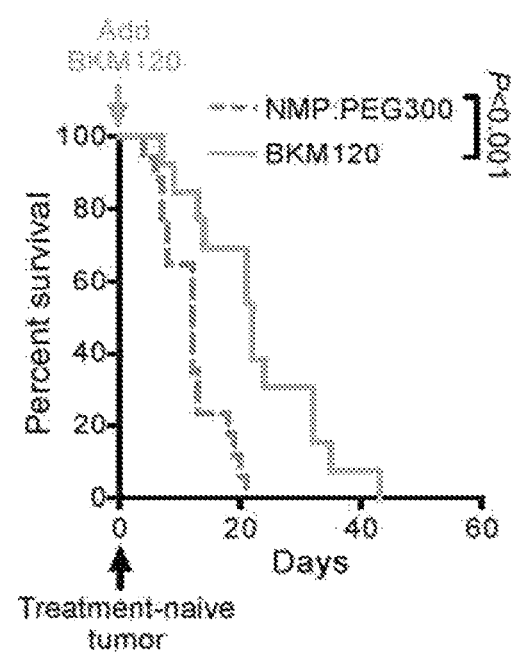
FIG. 11H—Kaplan-Meier analysis of high grade PDG tumors treated with either BKM120 (n=13 mice) or vehicle control (NMP:PEG300, n=17 mice). BKM120 as a single agent on treatment-naïve tumors provides a significant though modest survival benefit compared to vehicle control (median survival post-treatment initiation 22d versus 12d; Log-rank Mantel-Cox test P<0.001). Data were analyzed by Student's t-test unless indicated otherwise.

To investigate whether PI3K signaling is functionally important in driving recurrence, a preclinical intervention trial was performed. PDG mice bearing high-grade gliomas were treated with BLZ945 until they showed tumor rebound by MRI, at which point BKM120 treatment was performed (FIG. 2C, trial design 1, and FIG. 11E) at an appropriate dose to avoid reported off-target effects (15). BKM120 was chosen because it is a brain-penetrant pan-Class 1 PI3K inhibitor that is currently being clinically evaluated in GBM patients with recurrent disease following standard therapy. Animals with rebound tumors treated with continued BLZ945 monotherapy led to a median survival of 13d post-recurrence, whereas rebound tumors treated with BLZ945+BKM120 extended median survival to 51d (FIG. 2D) and blocked tumor progression after 2 weeks of treatment (FIG. 11F). By contrast, BKM120 monotherapy in rebound tumors (i.e. discontinued BLZ945) led to a median survival of 10d, which was indistinguishable from the vehicle control (FIG. 2D). Moreover, BKM120 was only modestly effective in treatment-naïve tumors (FIGS. 11, G and H). Collectively, these results indicate that continued CSF-1R inhibition is necessary to expose PI3K signaling dependency in rebound tumors and, consequently, a heightened sensitivity to pathway inhibition.

Figure 2C:
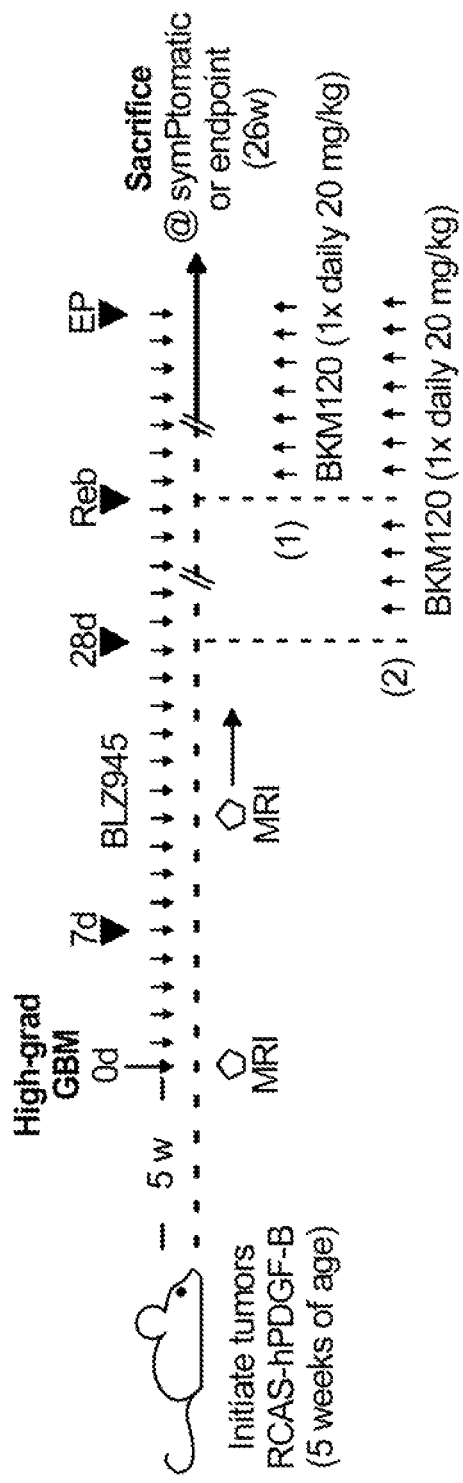
Figure 2D:
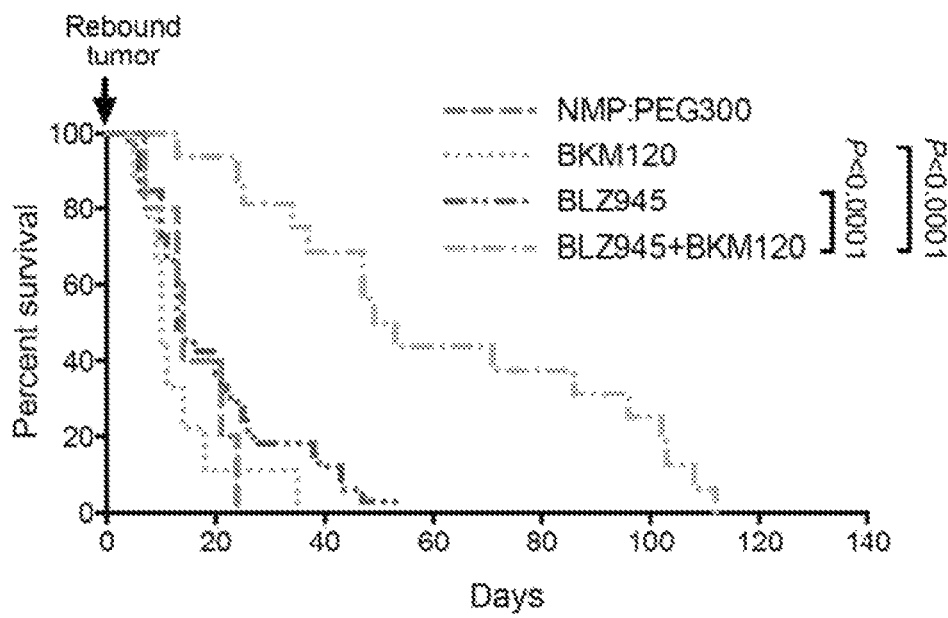
Figure 2E:
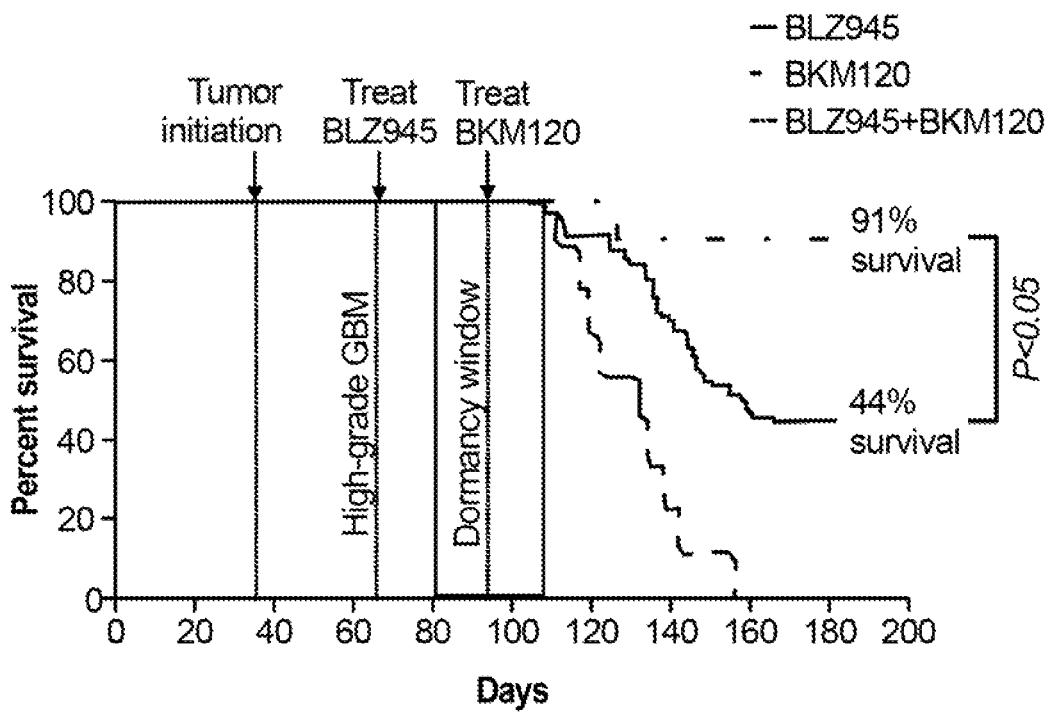

To determine if recurrence could be prevented by earlier PI3K inhibition, during the initial dormancy phase, GBM-bearing PDG mice were treated with BLZ945 alone for 28d, at which point BKM120 was added until the trial endpoint (FIG. 2C, trial design 2). With this early intervention, the percentage of animals that survived to endpoint increased substantially (91% BLZ945+BKM120) compared to single-agent treatments (44% BLZ945 alone and 0% BKM120 alone; FIG. 2E). Taken together, these results demonstrate that PI3K signaling is engaged during the acquisition of resistance to CSF-1R inhibition in the context of continued BLZ945 treatment.

Figure 2F:
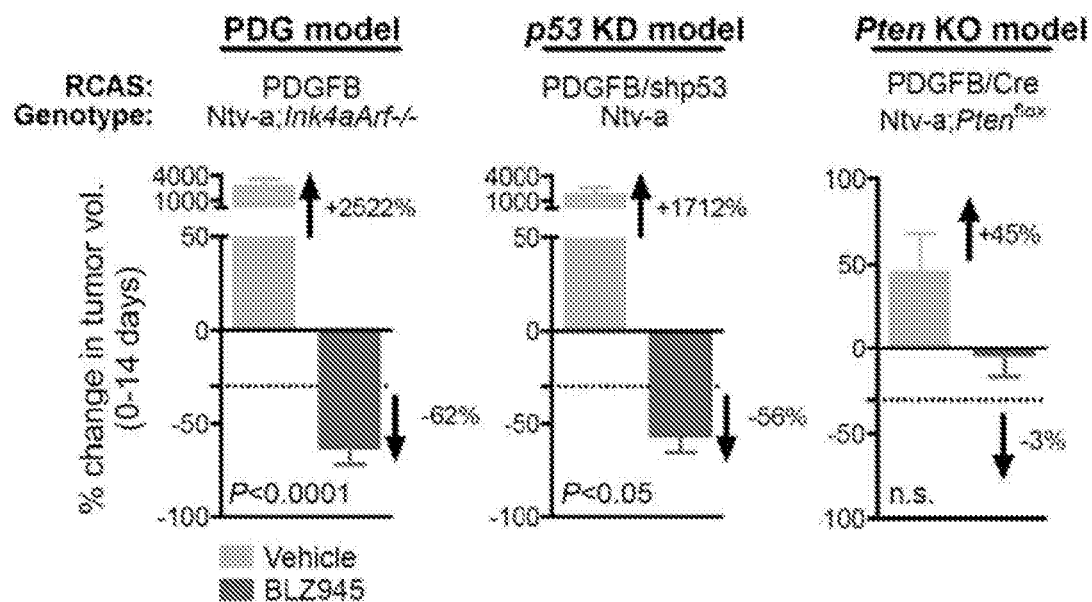
Figure 2G:
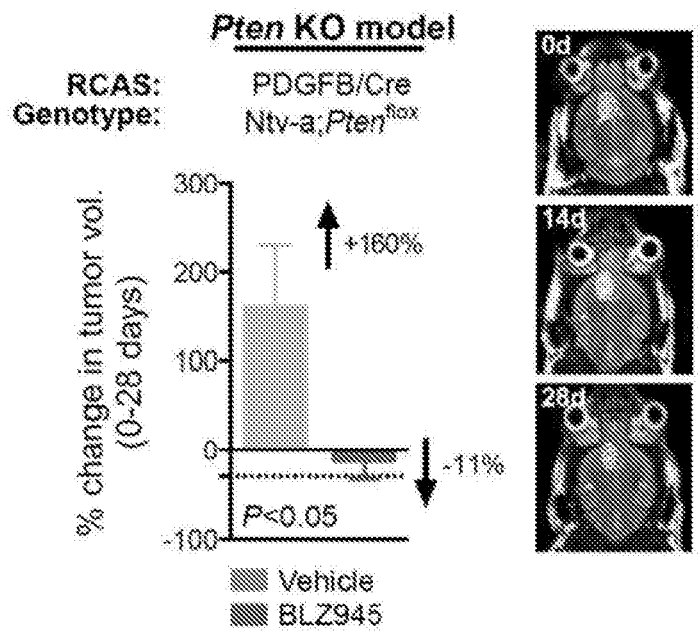

The finding that PI3K activation underlies resistance to CSF-1R inhibition was intriguing in light of the high frequency of mutations in the PI3K pathway in glioma patients (16). Therefore studies were performed to investigate whether genetic mutations in PI3K/PTEN would similarly confer a resistance-like phenotype in mouse models, which could potentially be informative in the clinical setting. To address this question, BLZ945 efficacy was compared in two additional RCAS-hPDGF-B/Nestin-Tv-a GBM models harboring distinct clinically-relevant oncogenic alterations besides Ink4a/Arf loss, including Pten deletion (Pten KO model) or p53 knockdown (p53 KD model; see methods). After 2 weeks of treatment, it was found that BLZ945 efficacy in the p53 KD model (56% reduction of tumor volume) was comparable to that of the PDG model (62% reduction). However, CSF-1R inhibition was less potent in the Pten KO model over the same time period (3% reduction; FIG. 2F). Furthermore, although a significant reduction in tumor volume was eventually observed in the Pten KO model after a prolonged treatment period of 4 weeks (11% reduction), this did not meet the response evaluation criteria in solid tumors (RECIST) standard for a partial response (FIG. 2G) (17). These results suggest that treatment efficacy of CSF-1R inhibitors may be blunted in patients with existing genetic alterations in the PTEN/PI3K pathway.

Resistance to CSF-1R Inhibition is Mediated by the Microenvironment

Figure 3A:
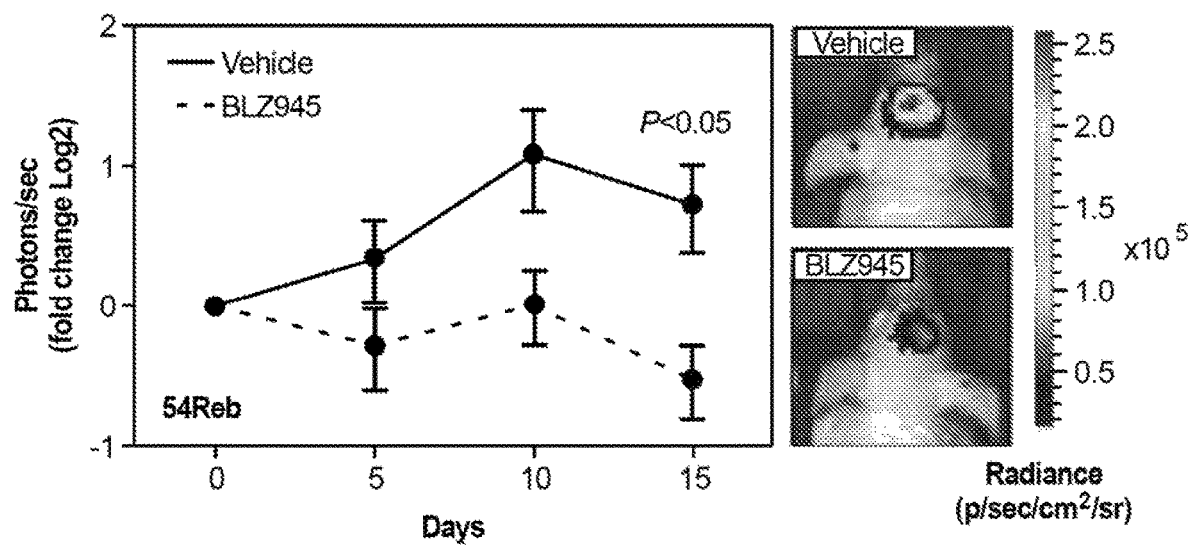
FIG. 3A-F. Resistance to CSF-1R inhibition is mediated by the microenvironment and rebound TAMs are alternatively activated.
Figure 3B:
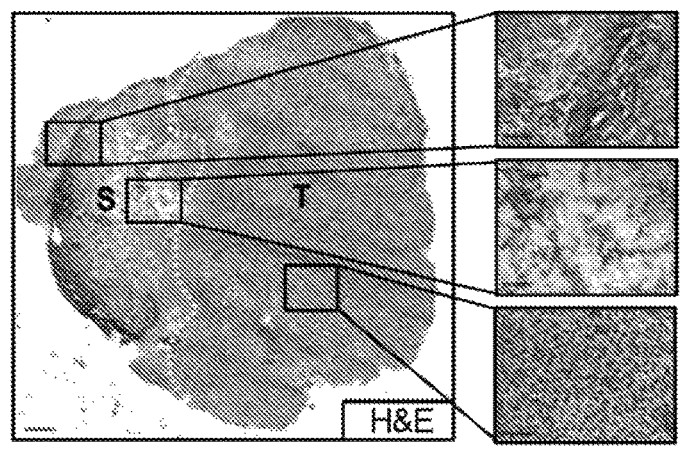
Figure 3C:
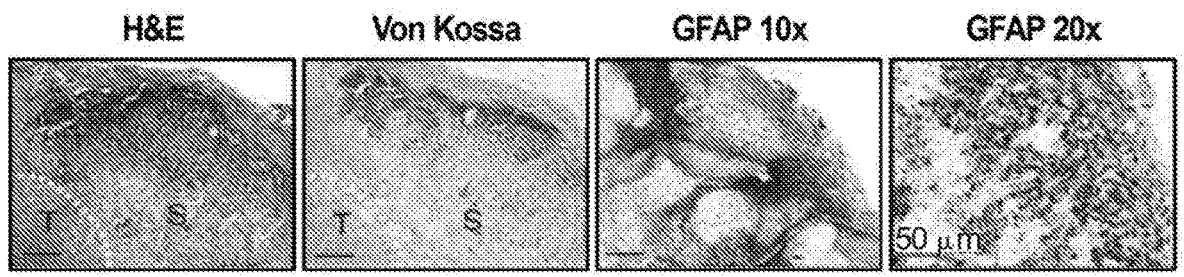
Figure 3D:
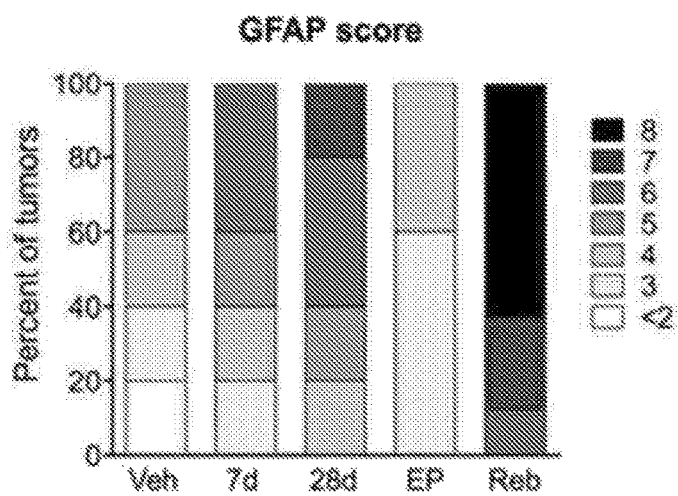
Figure 12A:
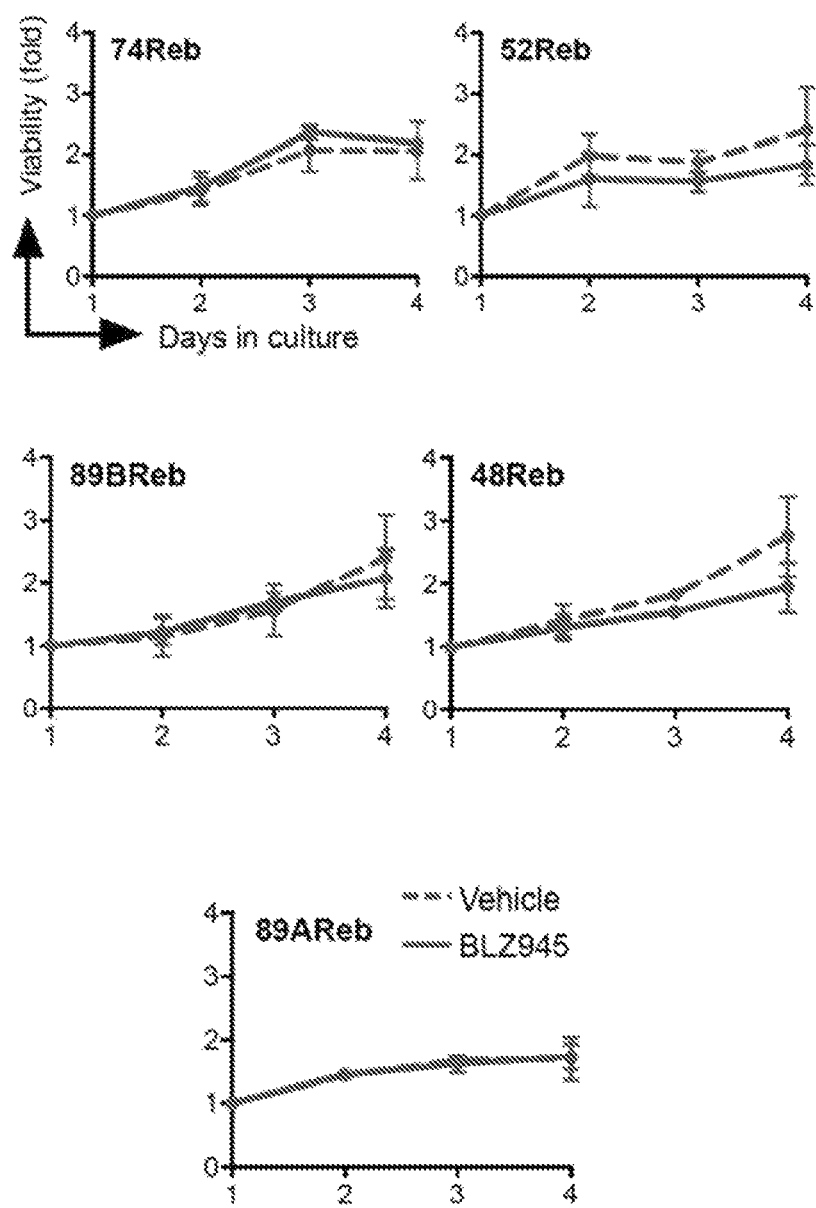
Figure 12B:
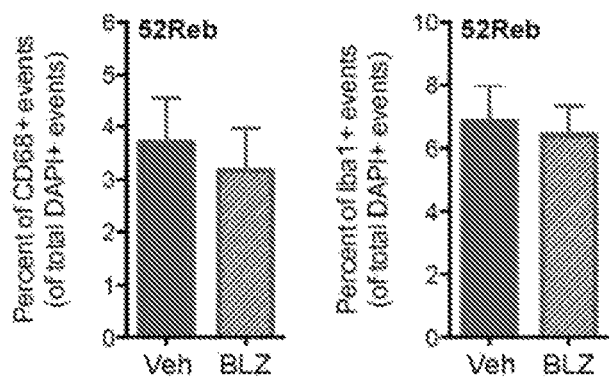
Figure 12C:
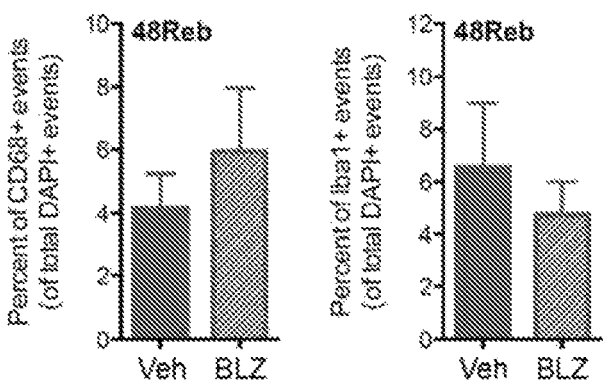
Figure 12D:
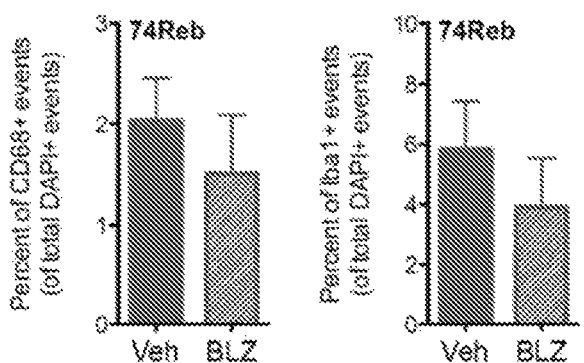
Figure 12E:
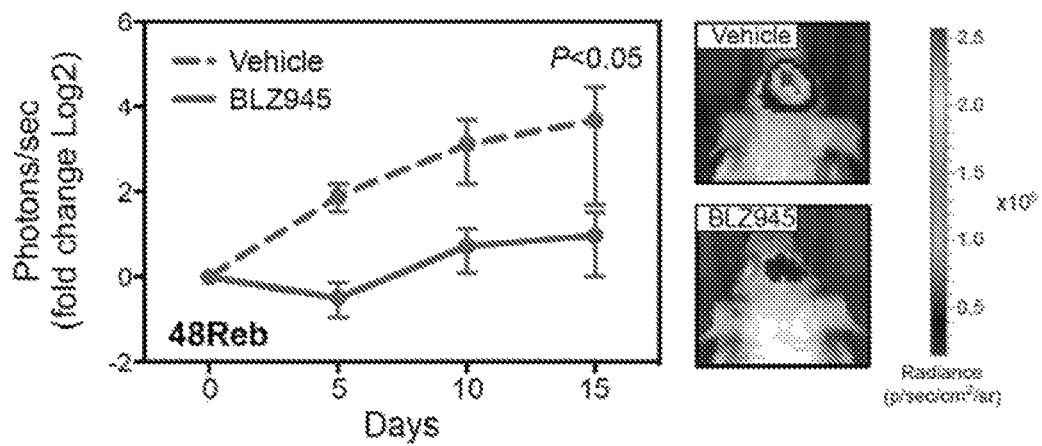
Figure 12F:
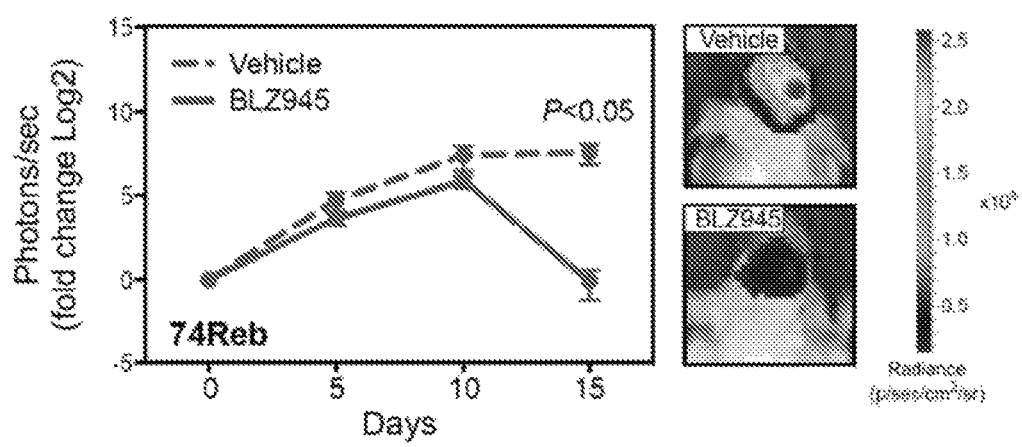

Next studies were performed to investigate how PI3K was activated in rebound tumors, and to explore whether resistance to BLZ945 was tumor cell-intrinsic or -extrinsic. It was previously established that BLZ945 does not directly affect glioma cell lines in culture (8), and it is demonstrated herein that CSF-1R inhibition also has no direct effect on viability of a panel of primary cell lines derived from rebound tumors (FIG. 12A). An intracranial tumor transplantation model was designed using early-passage Reb cells to address the following hypotheses: (i) resistance is tumor cell-intrinsic, therefore transplanted tumors will not respond to BLZ945, or (ii) resistance is mediated by the treatment-altered microenvironment, therefore transplanted tumors will re-establish sensitivity to CSF-1R inhibition in naïve animals. Interestingly, transplanted rebound tumors responded to BLZ945 treatment in the naïve setting (FIG. 3A, and FIG. 12, B to F), indicating that resistance is likely mediated by the TME.

Figure 12I:
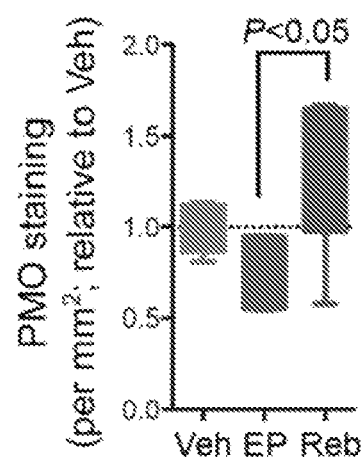
Figure 12I:
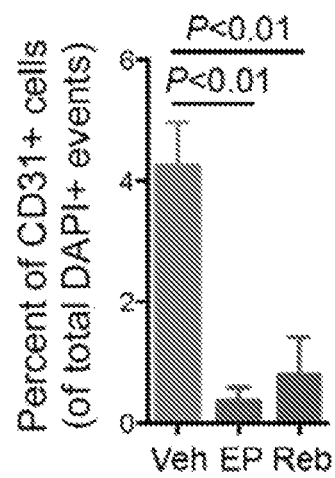
Figure 12I:
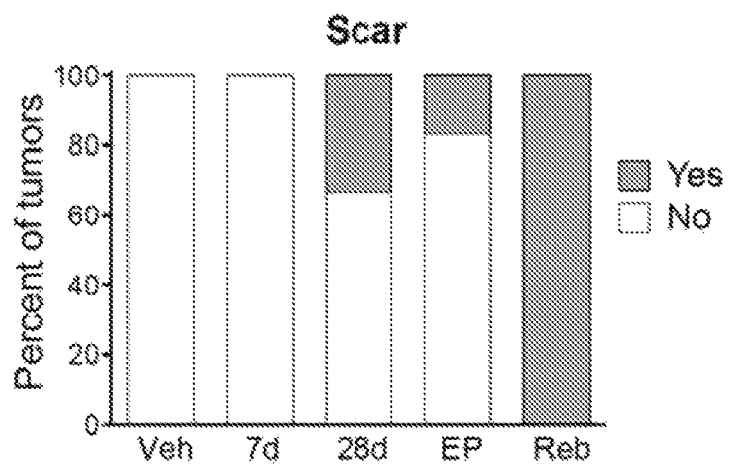

The TME was analyzed in recurrent disease to determine how resistance to CSF-1R inhibition develops. It was found that rebounding tumors always emerged adjacent to regions of glial scarring, characterized by reactive astrocytes, calcium deposition, and relatively low vascularity associated with elevated hypoxia (FIG. 3, B to D, and FIG. 12, G to I). By contrast, scarring was infrequently observed in the 28d and EP tumors (FIG. 12I). The scar tissue architecture was reminiscent of gliosis in response to neurodegeneration or physical injury (18). Given the parallels between a wound-associated microenvironment and tumorigenesis in epithelial tissues (19), it was hypothesized that this brain injury response may likewise be contributing to a microenvironment that is potentially triggering recurrent disease.

Figure 3E:
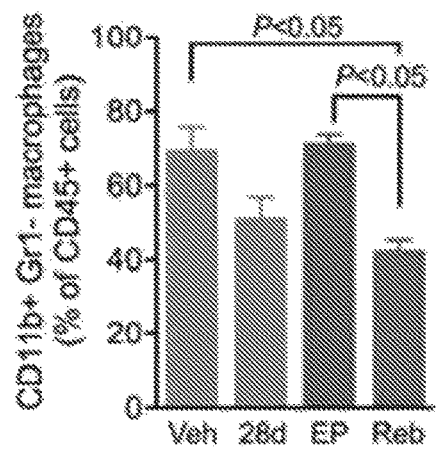
Figure 13A:
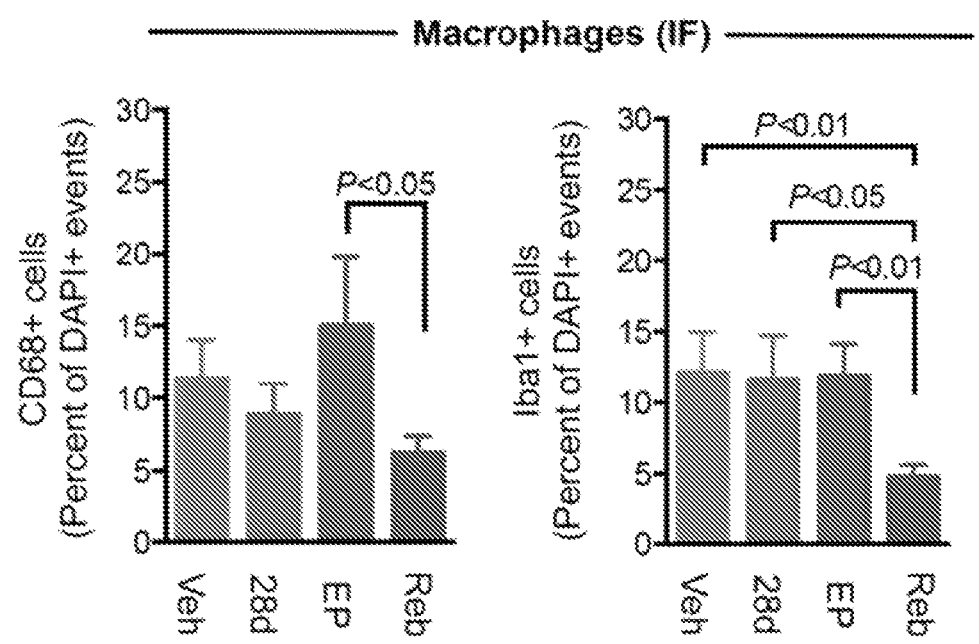
FIG. 13A-G. Analysis of TAM source and phenotype in rebound tumors.
Figure 13B:
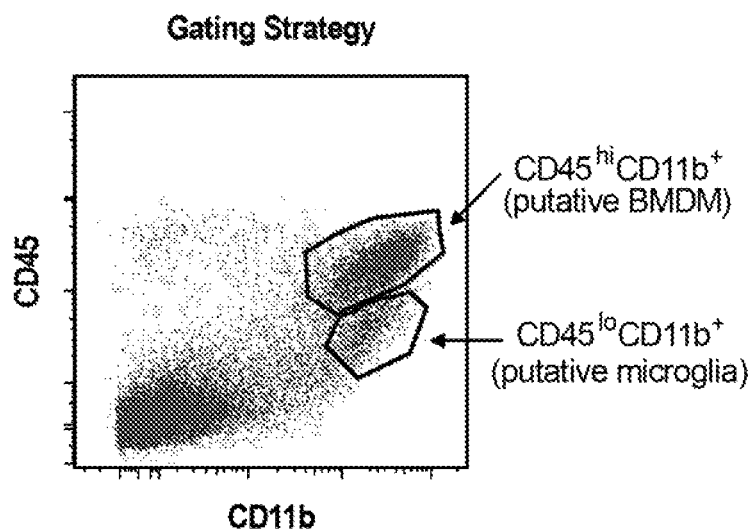
Figure 13C:
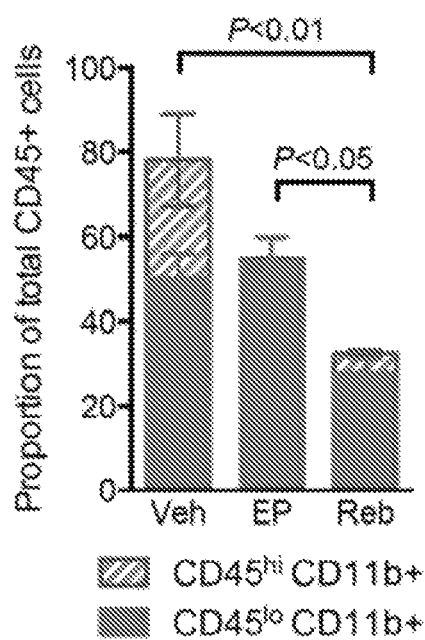
Figure 13D:
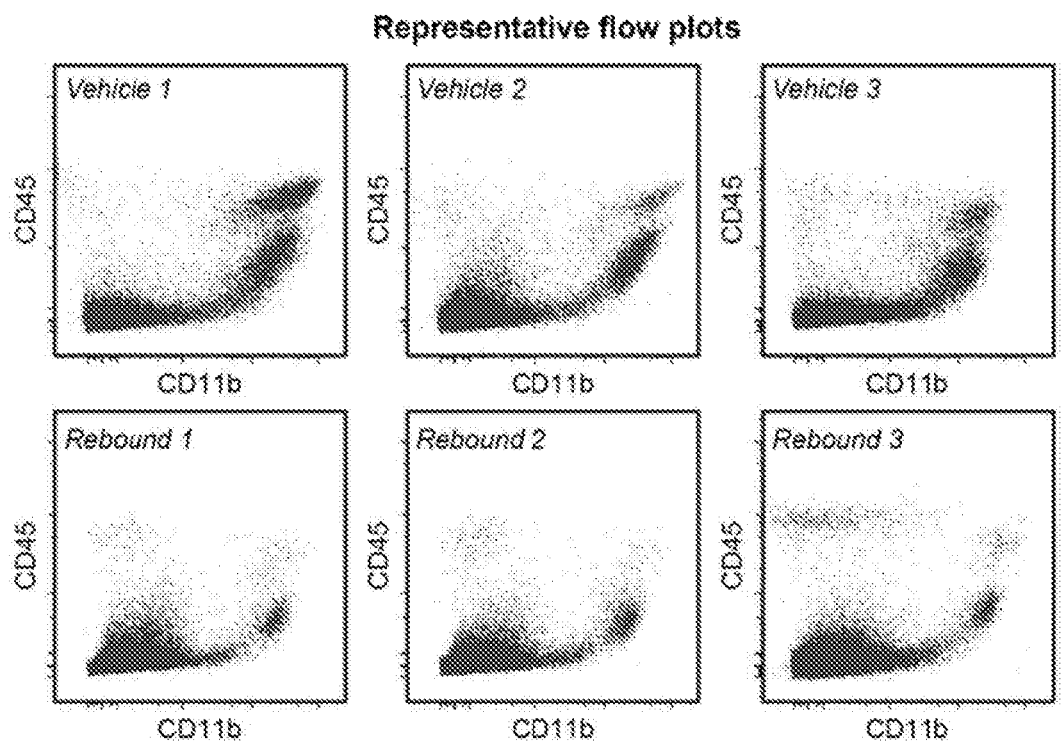
Figure 13E:
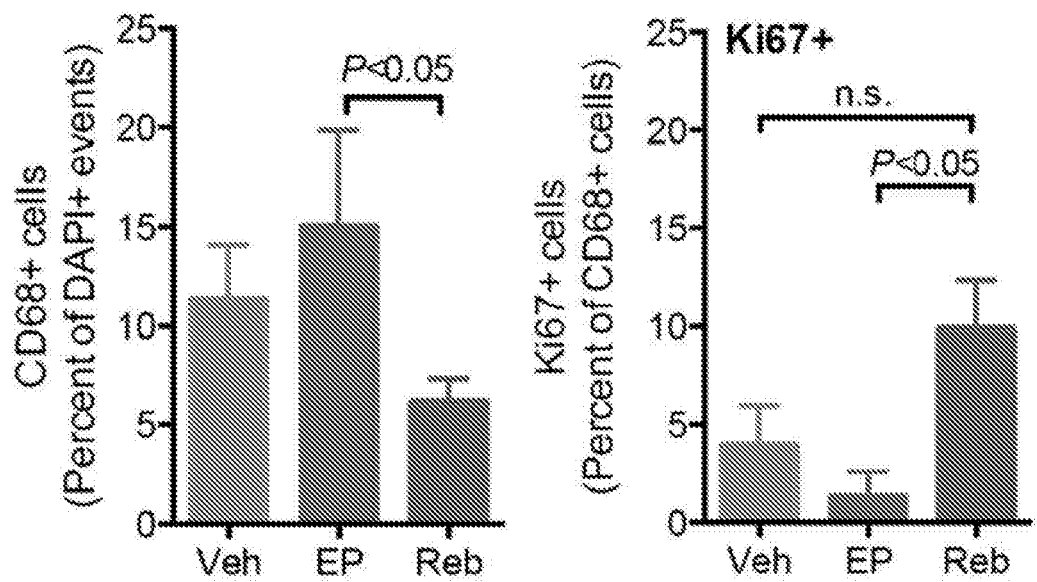
Figure 13F:
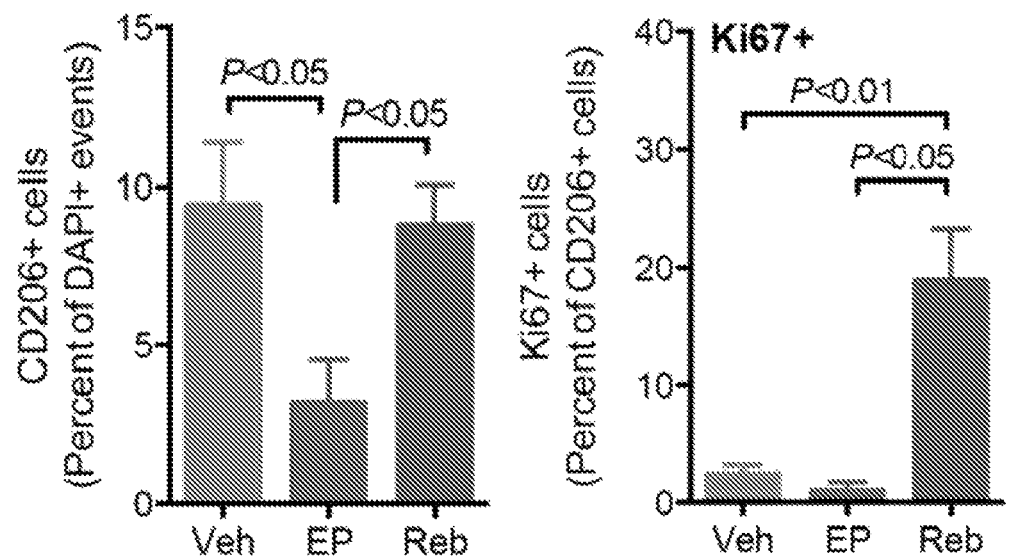
Figure 13G:
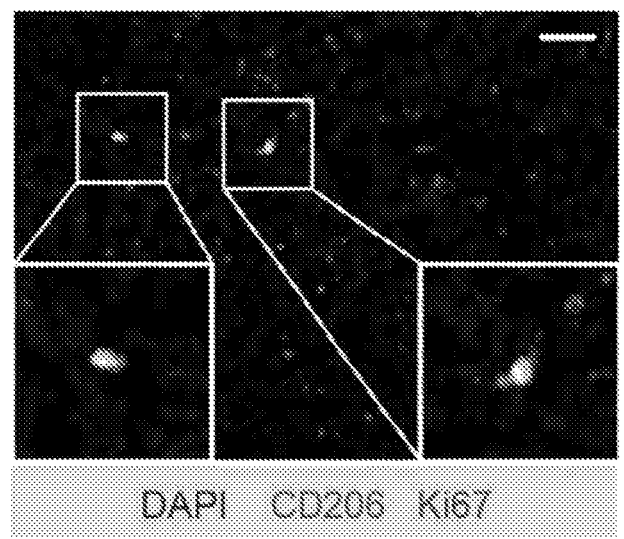

Rebound TAMs Adopt a Wound-Associated Signature that is Driven by Enhanced Interleukin-4 (IL-4) Signaling During gliosis, activated macrophages play a central role in providing growth factors and signaling molecules to nearby astrocytes and neurons, to form a reactive barrier that limits the extent of tissue damage in the brain (18, 20). Given that BLZ945 is a macrophage-targeted drug, TAM numbers and phenotype were analyzed in rebound tumors. It has previously been shown that TAMs are not depleted in the glioma TME in a 1-week trial with BLZ945, but rather downregulate expression of M2-like genes and increase phagocytosis of tumor cells (8, 21). Consistently, it is shown herein that TAMs are still present in 7d, 28d, EP or Reb tumors (FIG. 3E and FIG. 13A). Interestingly, when flow cytometry was used to discriminate between $CD45^{lo}CD11b+$ cells (putative microglia) versus $CD45^{hi}CD11b+$ cells (putative bone marrow-derived macrophages, BMDMs) (22-24) in Veh, EP and Reb tumors (FIG. 13; see methods for further discussion), it was found that long-term BLZ945 treatment enriched for $CD45^{lo}CD11b+$ TAMs (FIGS. 13, C and D). This is potentially either a consequence of phenotypic mimicry between the macrophage populations, or the result of one macrophage population responding differently to CSF-1R inhibition than the other. Co-staining of CD68 or CD206 macrophage markers in combination with Ki67 demonstrated that a subset of remaining TAMs in rebound tumors were proliferating (FIG. 13, E to G). These results suggest that rebound TAMs (enriched for $CD45^{lo}CD11b+$ cells) may undergo a low level of replication, presumably as a means to compensate for the duress caused by prolonged CSF-1R blockade.

Figure 3F:
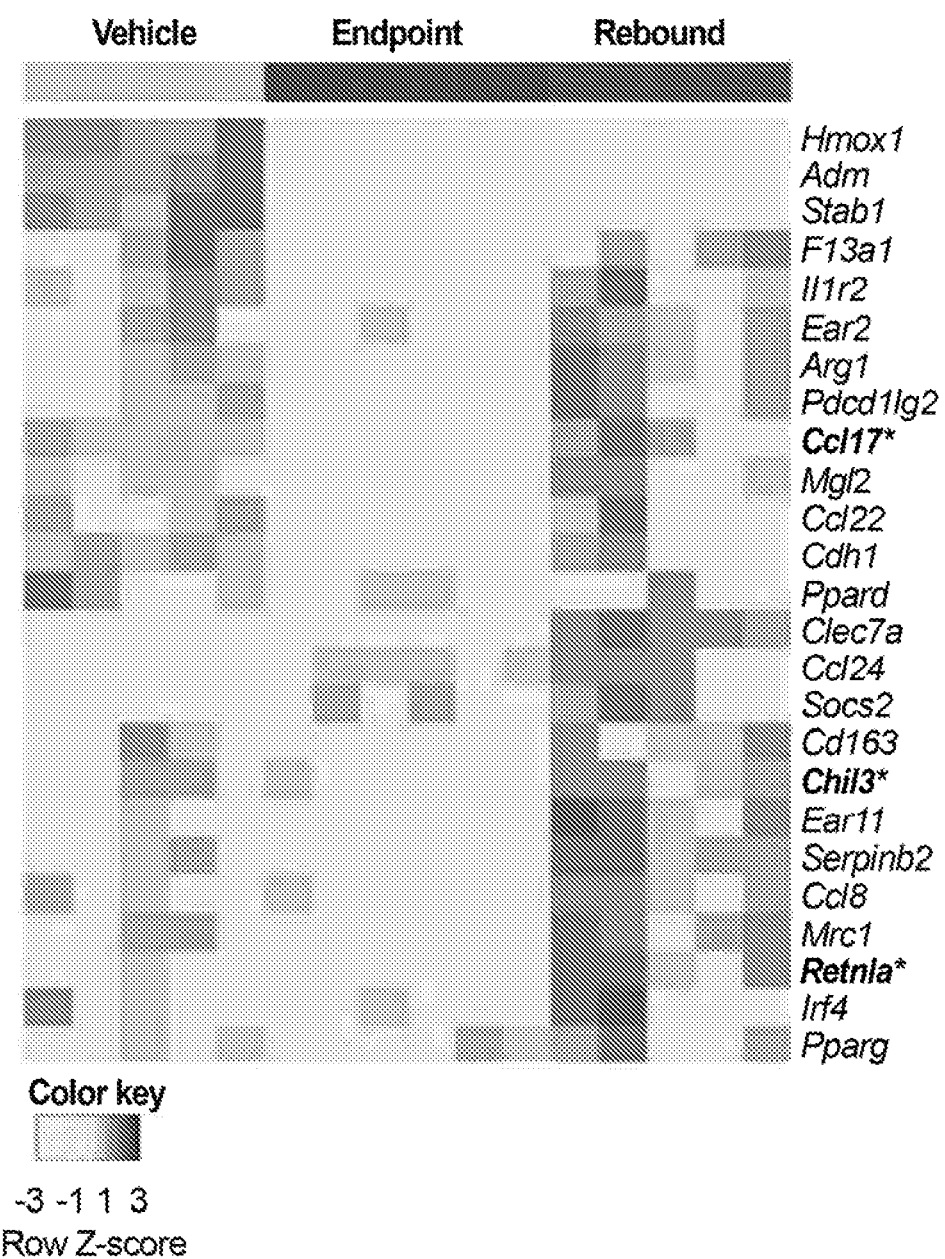
Figure 14A:
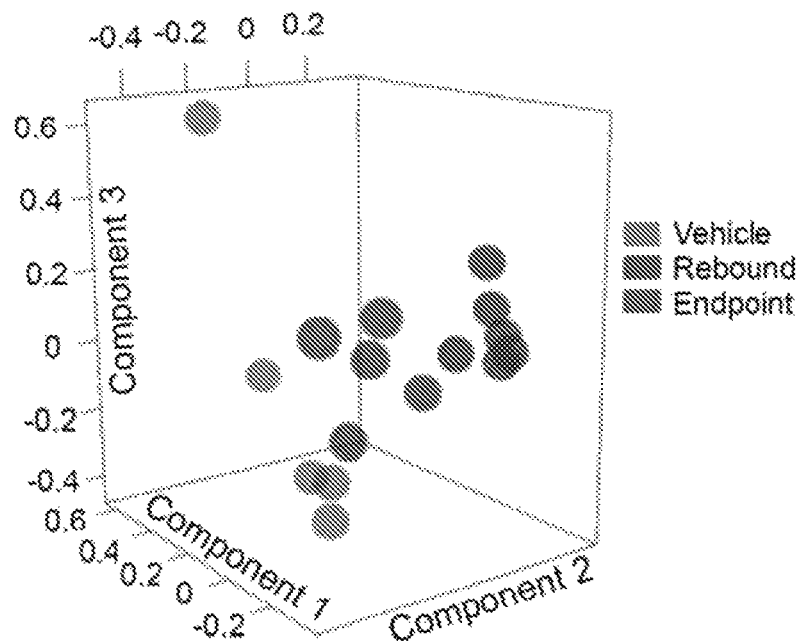
FIG. 14A-F. Validation of IL4- or TGFβ1-driven TAM activation from RNA-seq data.
Figure 14B:
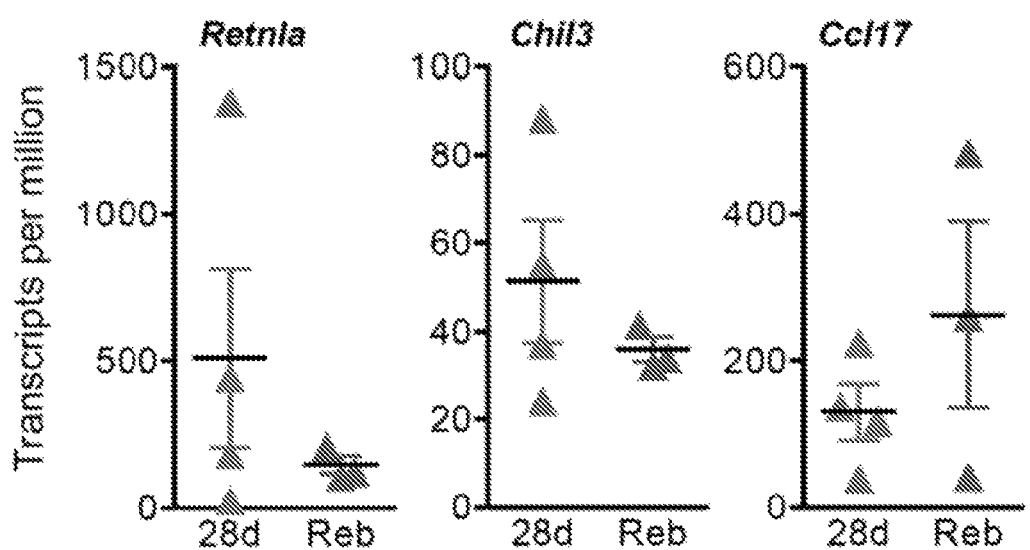
Figure 14C:
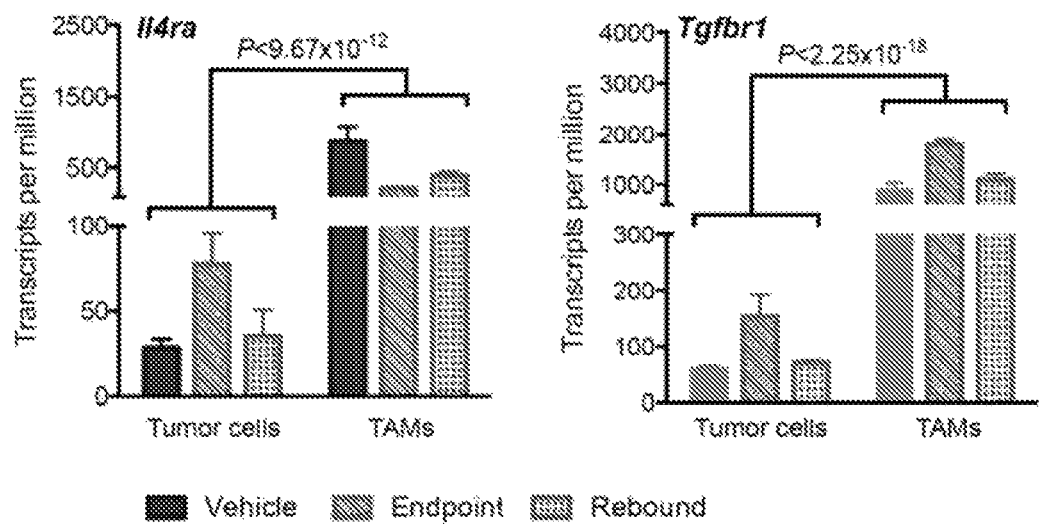
Figure 14D:
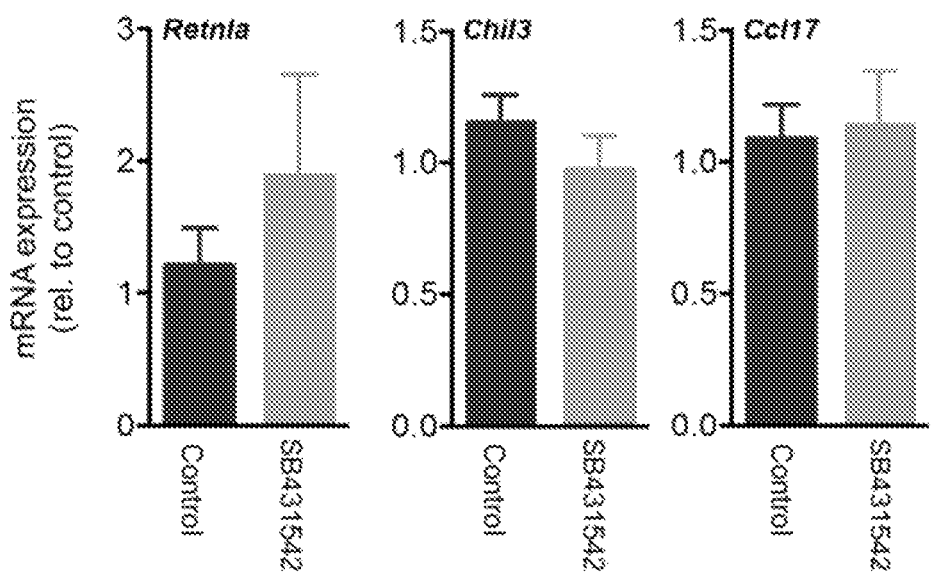
Figure 14E:
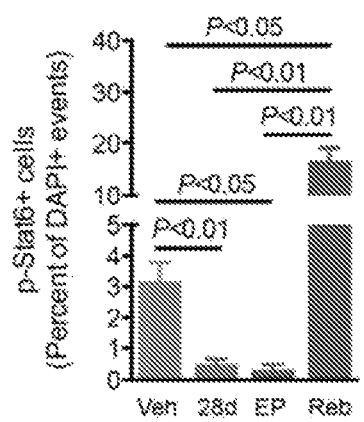
Figure 14F:
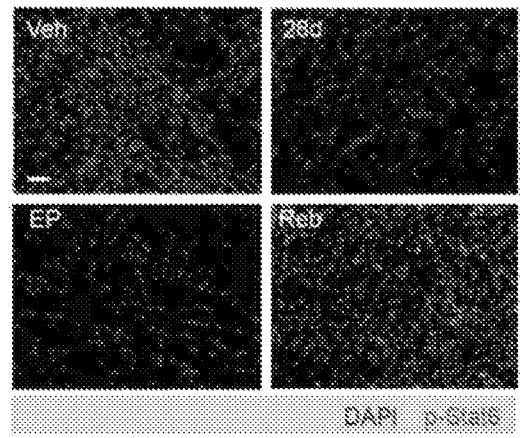

To assess potential differences in activation states, TAMs were FACS-purified from Veh, EP and Reb tumors, and RNA-seq was performed. Principal component analysis confirmed distinct global gene expression profiles for Veh, EP and Reb TAMs (FIG. 14A), and differential expression analysis revealed large numbers of differentially expressed genes between the three groups. A subset of M2-like genes previously identified as altered by CSF-1R inhibition (8, 25) was examined. It was found that compared to Veh TAMs, alternative activation was suppressed in EP TAMs, while a subset of these genes were highly expressed in Reb TAMs (FIG. 3F). In accordance with previous findings (8), no inverse relationship was observed for M1-like markers such as tumor necrosis factor α (TNFα) across the different treatment groups (25). Together these findings support the hypothesis that the Reb TME is pro-tumorigenic.

Figure 4C:
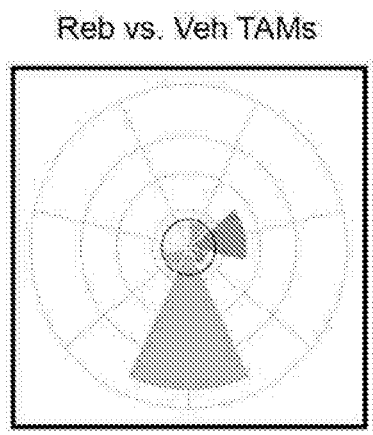
Figure 4C:
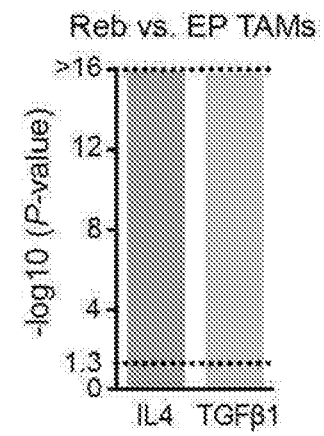
Figure 4C:
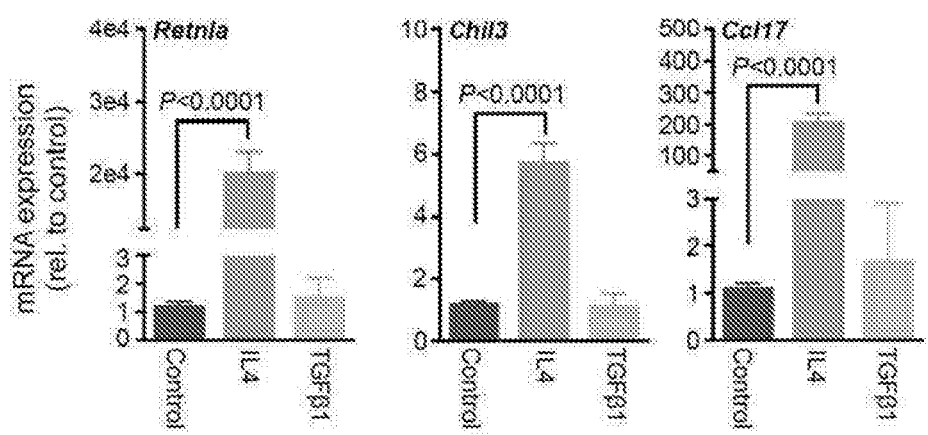
Figure 4D:
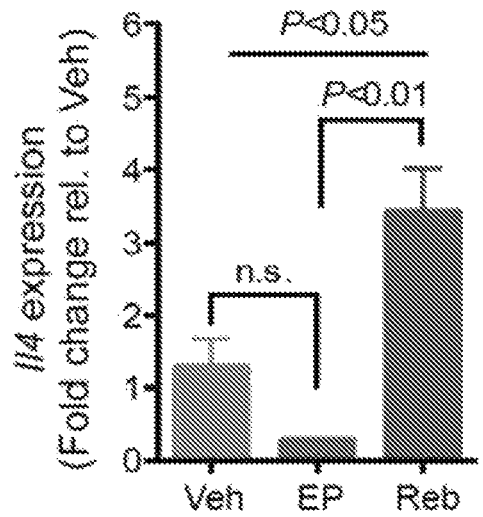
Figure 4E:
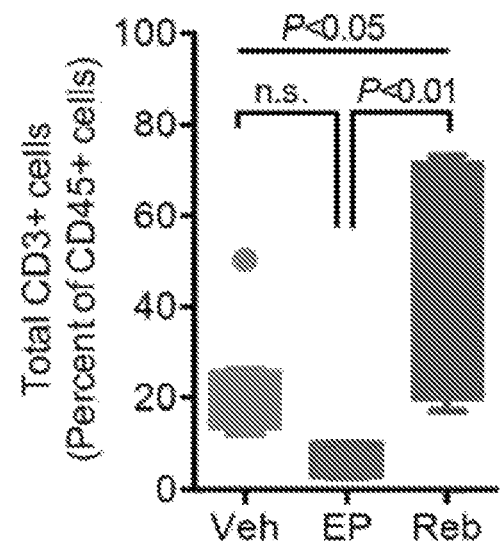
Figure 4F:
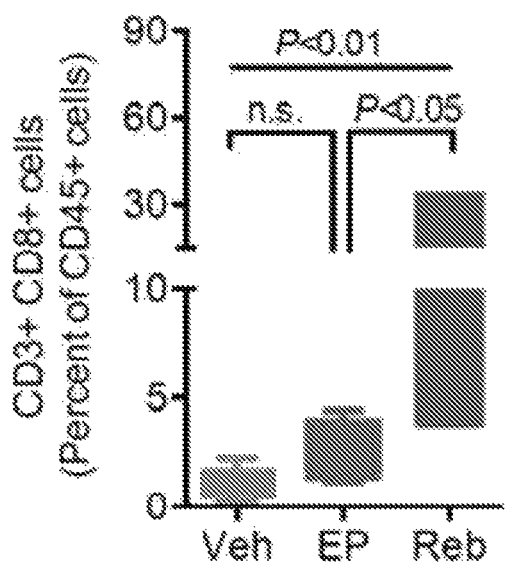

Given the similarities in alternative activation between Veh and Reb TAMs according to the M1/M2-like paradigm (26), yet clear differences in drug response between treatment-naïve and rebound tumors, a more fine-tuned approach was employed to defining macrophage phenotype. A spectrum model of macrophage activation was computationally interrogated, defined by gene sets that are altered in response to different stimuli, including interferon γ (IFNγ), IL4, TNFα, transforming growth factor β1 (TGFβ1), IL1β, and two toll-like receptor (TLR) agonists specific for TLR2 (macrophage-activating lipopeptide 2; MALP2) and TLR9 (unmethylated CpG-containing oligonucleotide; CPG) (27, 28). It was determined that IL4- and TGFβ1-targeted gene sets were significantly enriched in Reb TAMs compared to Veh TAMs (FIG. 4A), and that there was a significant enrichment of these same gene sets in Reb TAMs versus EP TAMs (FIG. 4B). Given that IL4 is a known mediator of alternative activation associated with a wound-healing phenotype in macrophages (20, 29), and the role of TGFβ1 during wound-healing and tissue turnover in multiple contexts (30, 31), these results were consistent with the observation of glial scarring in association with rebound tumors. Indeed, a number of M2-like genes expressed by macrophages involved in wound repair and resolving inflammation (Retnla, Chil3, Ccl17) were enriched in Reb TAMs (FIG. 3F). By contrast, RNA-seq analyses of an independent set of Reb and 28d TAM samples revealed no significant differences in expression across this same gene set (FIG. 14B), suggesting that a subset of 28d tumors may be rebound precursors, and that induction of M2-like gene expression precedes recurrence. When the ability of IL4 or TGFβ1 to regulate expression of these wound-associated genes in BMDMs in vitro was investigated, it was found that IL4 was a potent inducer, whereas TGFβ1 was not (FIG. 4C, and FIGS. 14, C and D), indicating the specificity of IL4 for regulation of this particular gene set. Corroborating these findings, increased expression of Il4 in rebound tumors was confirmed by qRT-PCR (FIG. 4D), and elevated canonical downstream signaling was confirmed by immunofluorescent staining for phosphorylated Stat6 (p-Stat6) in PDG tissue samples from the long-term trials (FIGS. 14, E and F).

Figure 4G:
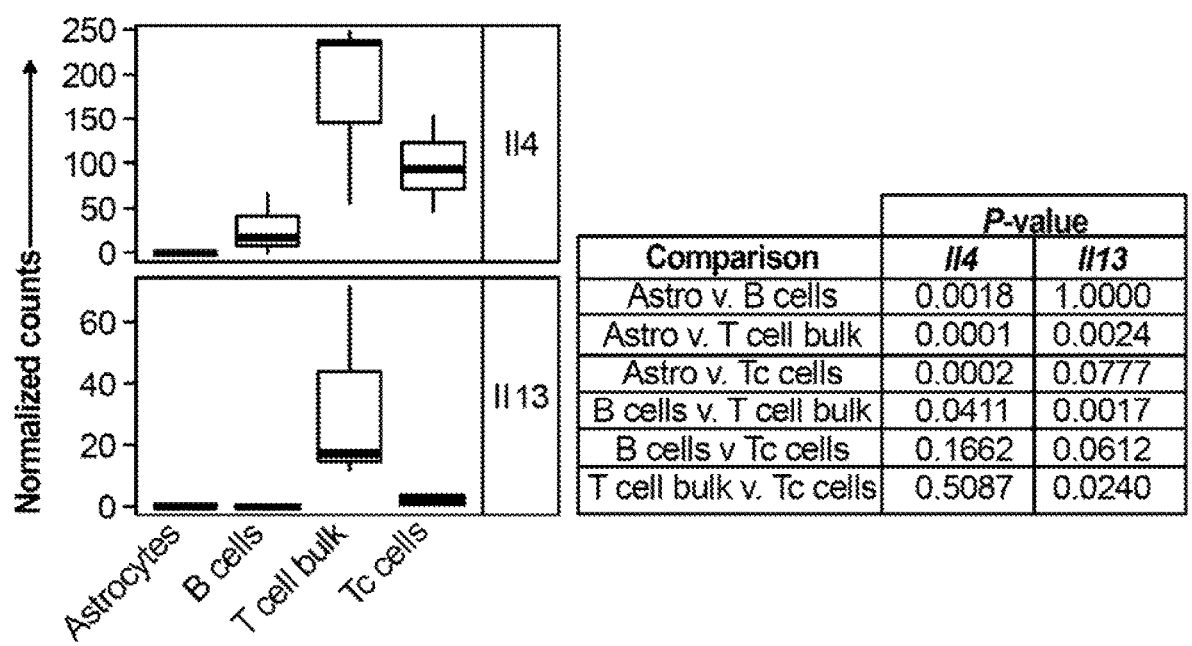
Figure 15A:
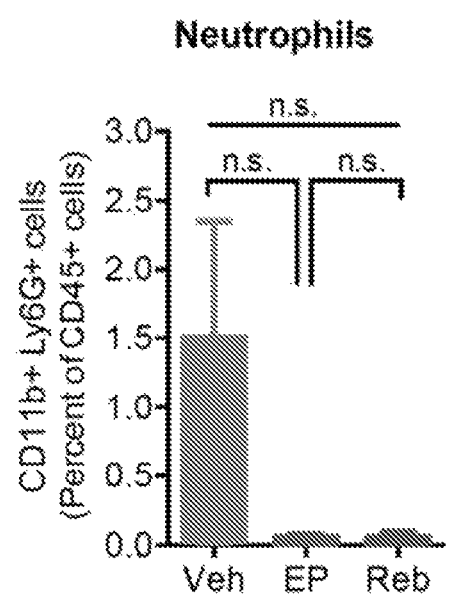
Figure 15B:
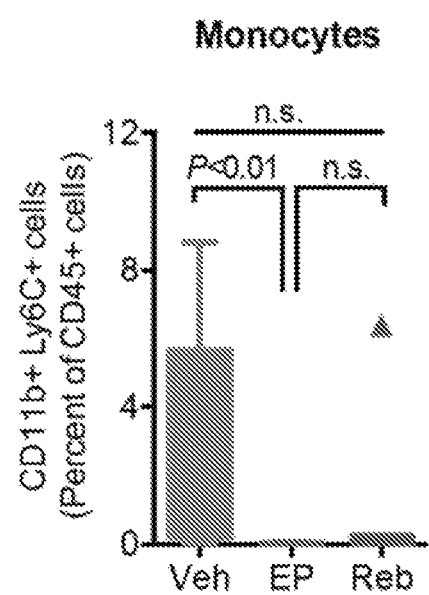
Figure 15H:
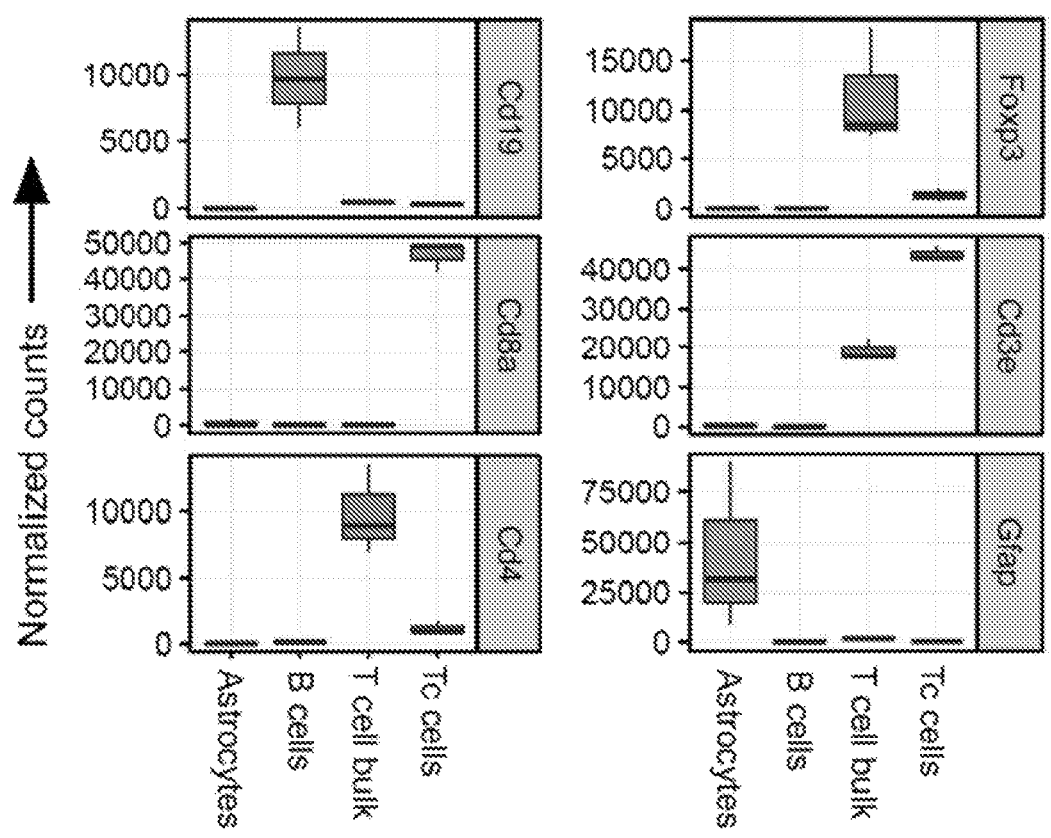
Figure 15I:
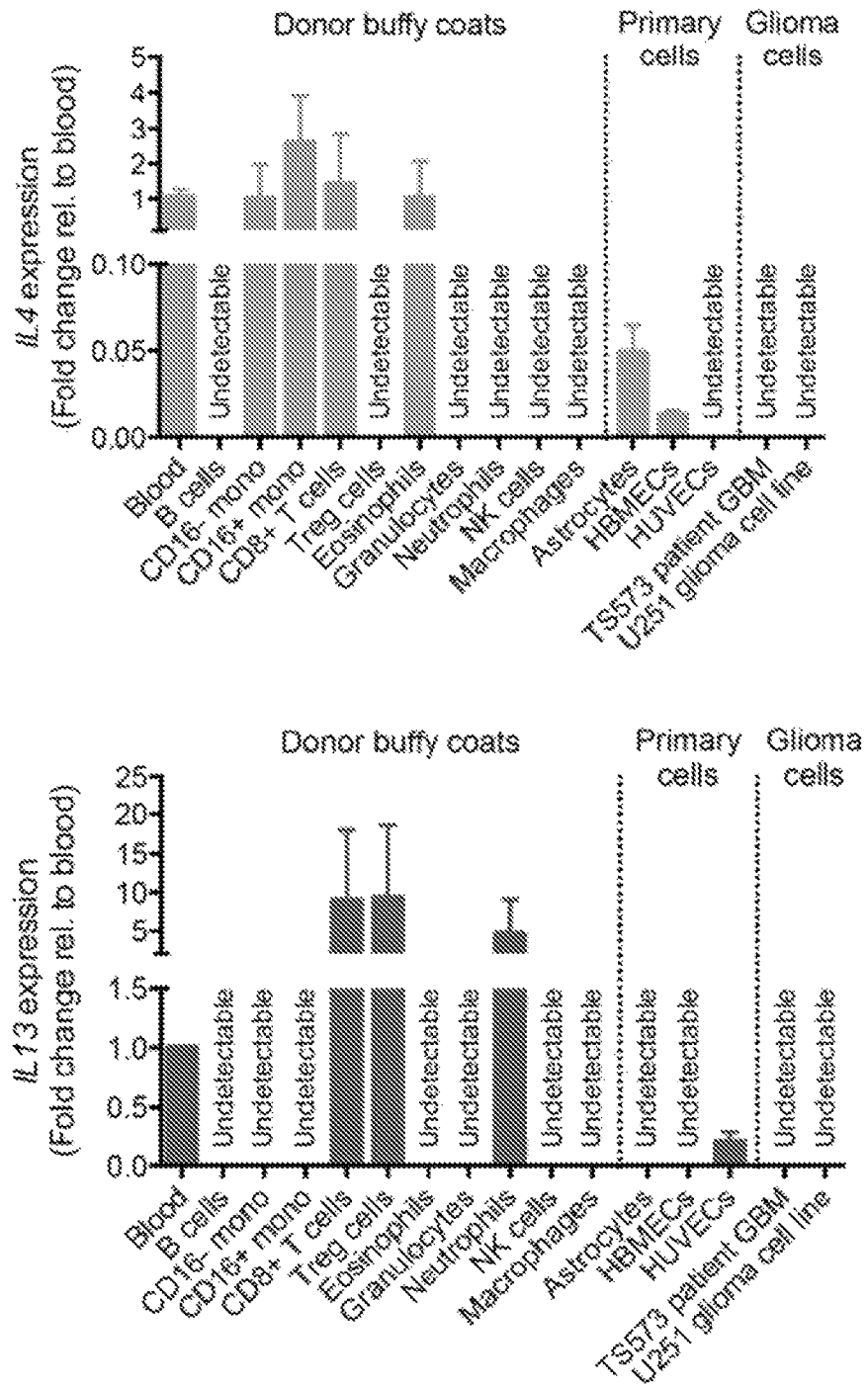

To determine the cellular source of IL4 in this model, multicolor flow cytometry was used to immune-profile Veh, EP, and Reb tumors using a panel of myeloid (CD11b, Gr1, Ly6G, Ly6C, CD11c, Tie2, MHCII) and lymphoid (CD19, CD3, CD4, CD8, FoxP3) cell markers. While it was found that few cell types were uniquely enriched in rebound tumors (FIG. 15, A to G), there was a significant increase in the proportion of CD3+ T cells in rebound tumors, driven by the CD8+ fraction (FIGS. 4, E and F). FACS-purification of these cells from rebound tumors along with other putative contributors of IL4 (including astrocytes (FIG. 3D), B cells (32-34), and bulk T cells), revealed that Il4 expression was enriched in both bulk T and CD8+ T cell fractions (FIG. 4G and FIG. 15H). By comparison, expression of Il13, a closely related cytokine that shares the IL4Rα subunit in its heterotypic receptor to initiate canonical Stat6 signaling, was enriched in the bulk T cell fraction (FIG. 4G). Expression of IL4 was assessed in a panel of human cell types, and detected in CD8+ T cells as expected, in addition to monocytes, eosinophils, astrocytes, and brain microvascular cells (FIG. 15I). This data is consistent with IL4 being produced by multiple cell types.

The IGF-1/IGF-1R Signaling Axis is Induced in Rebound Gliomas

Figure 16A:
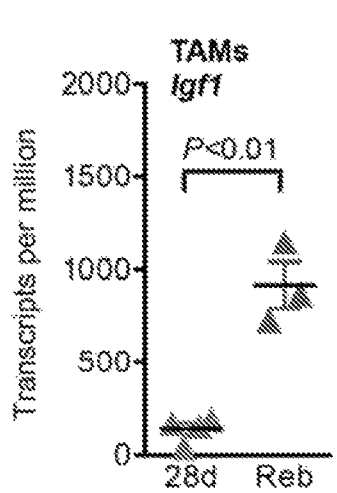
FIG. 16A-J. IGF-1R signaling is elevated in BLZ945-resistant tumors.
Figure 16B:
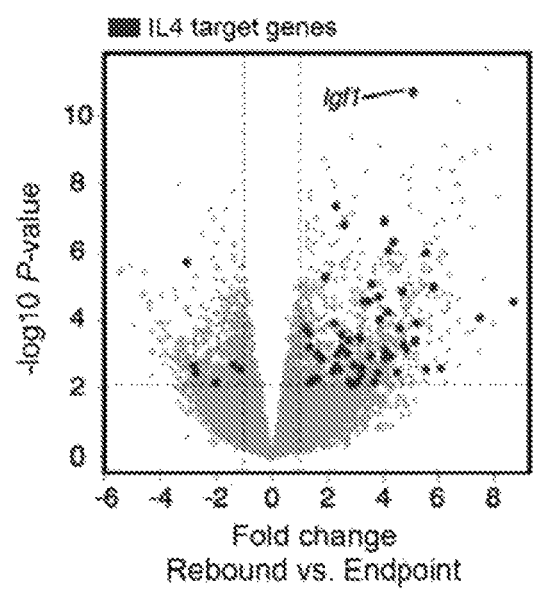
Figure 16C:
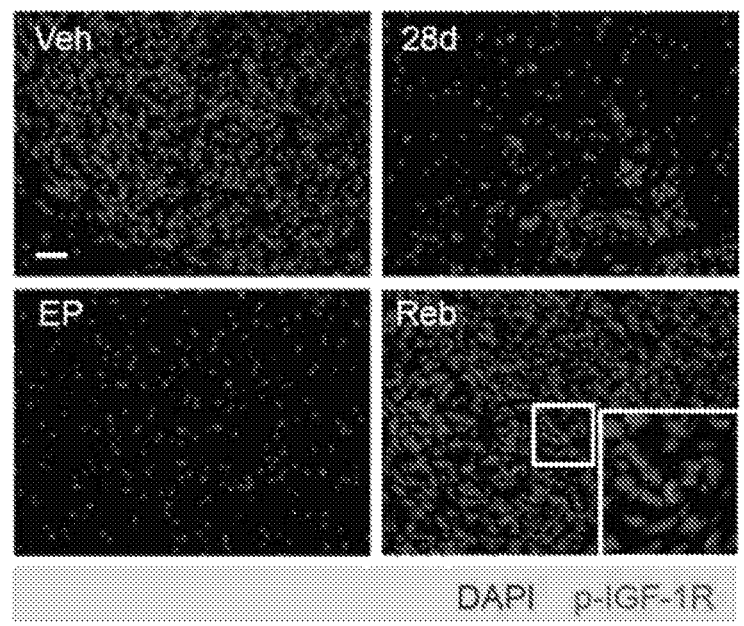
Figure 16D:
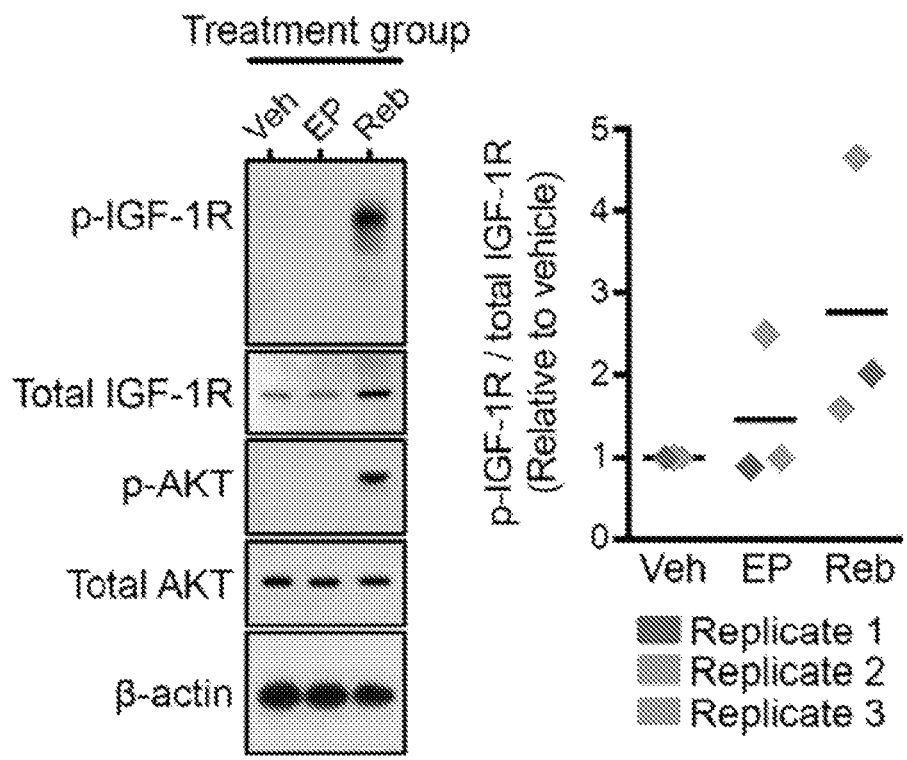
Figure 16E:
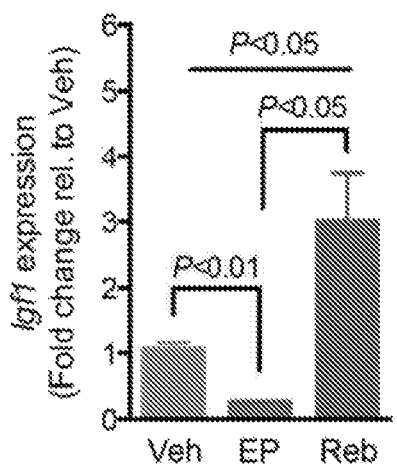
Figure 16F:
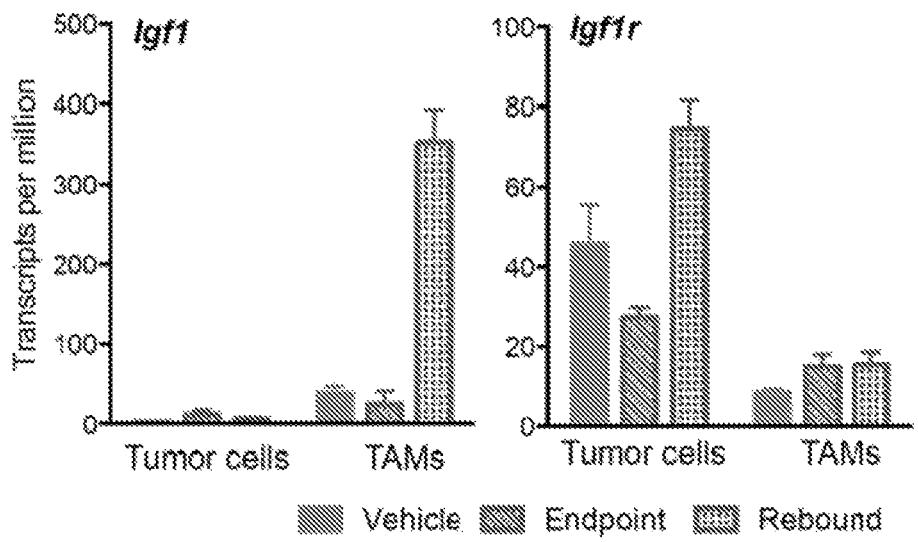

Next studies were performed to investigate how IL4 and wound-associated gene expression might be connected to PI3K signaling in rebound tumors. Differential gene expression analysis revealed that TAM-derived Igf1 was one of the most significantly upregulated genes in Reb TAMs compared to EP TAMs, which was confirmed in comparisons with Veh TAMs or 28d TAMs (FIGS. 5, A and B, FIG. 16A). This was particularly interesting as Igf1 is an IL4 target gene in macrophages (FIG. 16B) (35-37), it is a known mediator of tissue repair and neuroprotection (38-41), and importantly, one of its canonical downstream signaling pathways is PI3K/AKT (42). Congruent Igf1r upregulation was identified in glioma cells purified from rebound tumors (FIG. 5C), elevated p-IGF-1R was found in rebound tumors by immunostaining and western blotting (FIG. 5D, and FIGS. 16, C and D), and Igf1 upregulation was found in snap-frozen rebound tissue samples by qRT-PCR (FIG. 16E). Additionally, levels of Igf1 expression were substantially higher in Reb TAMs than tumor cells, while Igf1r expression was enriched in tumor cells compared to TAMs (FIG. 16F). Together these data demonstrate elevated IGF-1 signaling in recurrent disease.

Figure 16G:
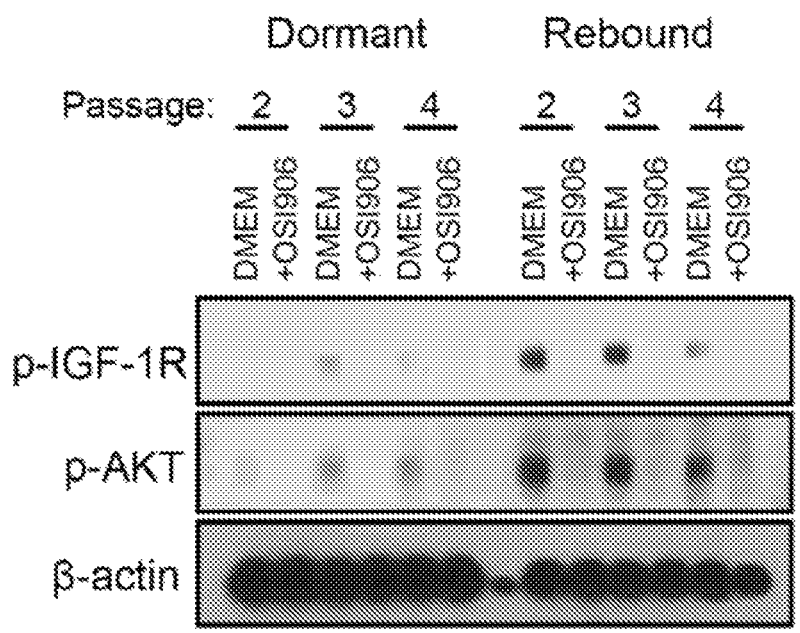
Figure 16H:
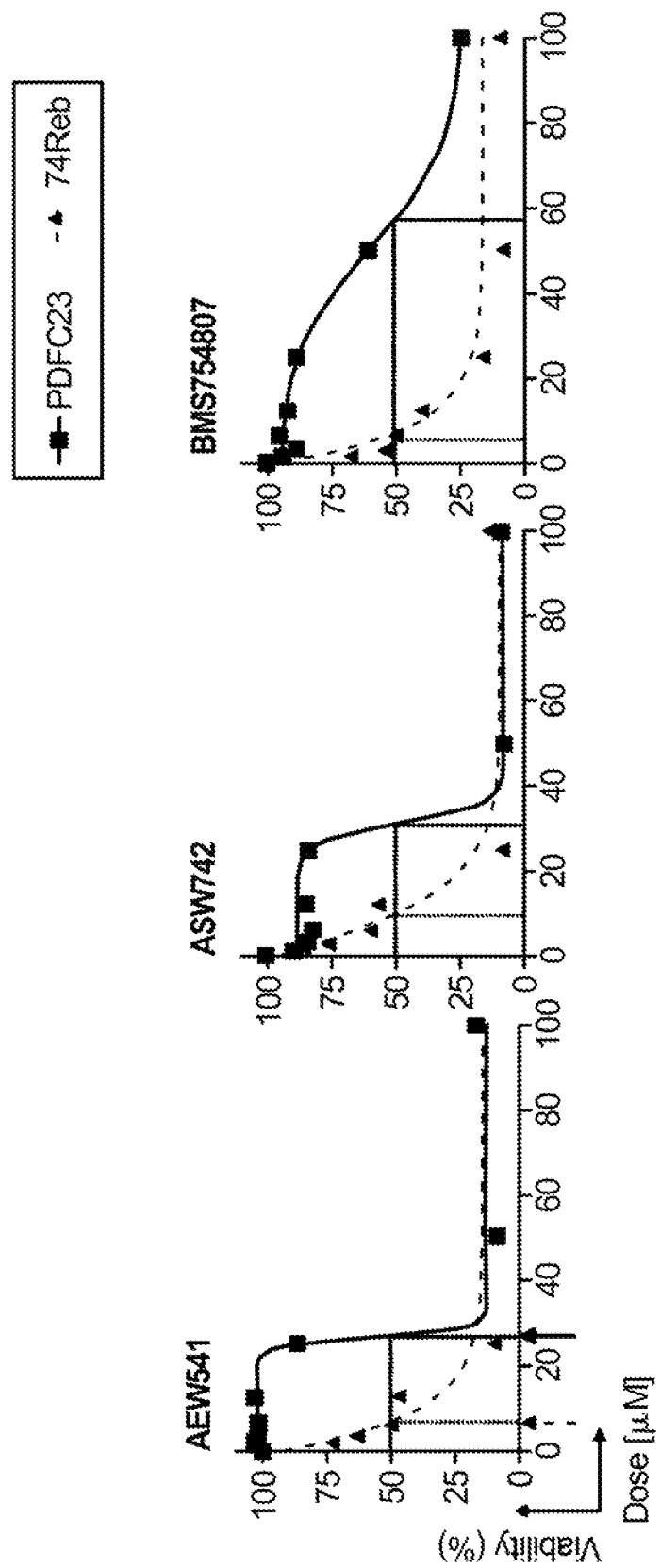

To assay the effects of IGF-1 specific to the rebound setting, multiple approaches were used: first, through western blot analysis, higher baseline levels of p-IGF-1R in early-passage rebound tumor cell lines compared to cell lines that we were able to propagate from dormant tumors in culture were confirmed (FIG. 16G; see methods). It was determined that phosphorylation and downstream signaling could be reduced in rebound cell lines by using an inhibitor of IGF-1R (FIG. 16G), and that early-passage rebound cells were more sensitive to IGF-1R blockade than naïve glioma cells in vitro using multiple pharmacological inhibitors (FIG. 5E and FIG. 16H).

Next, to model the effects of macrophage-derived IGF-1 on rebound tumor cells, an ex vivo culture system was designed using primary glioma microenvironment cultures (GMECs). GMECs contain multiple cell types from the glioma TME when harvested at early-passage, including macrophages, T cells, astrocytes, among others (FIG. 16I) (8). It was hypothesized that rebound GMECs would be able to stimulate production of IGF-1 by macrophages, and subsequent growth of tumor cells. To test this, conditioned media (CM) was collected from rebound GMECs and applied to wild-type (WT) BMDMs for 24 h. After this treatment, CM was collected from the GMEC-stimulated BMDMs (Stim CM) and applied to either rebound or naïve tumor cell lines in an MTT assay, +/− a neutralizing antibody against IGF-1 (see FIG. 16J for experimental design). It was found that Stim CM induced proliferation of rebound cell lines more effectively than naïve cell lines, and this effect was blocked by IGF-1 neutralization (FIG. 5F). These results suggest that the cells within a recurrent tumor are capable of stimulating production of IGF-1 by macrophages, which in turn gives a proliferative advantage to rebound tumor cells.

Figure 5G:
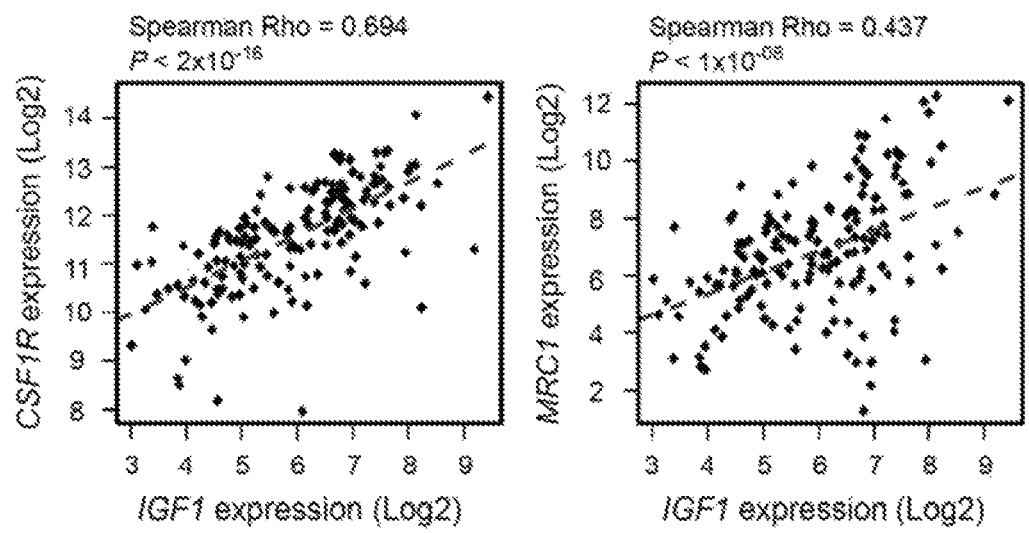
Figures 5H, 5I:
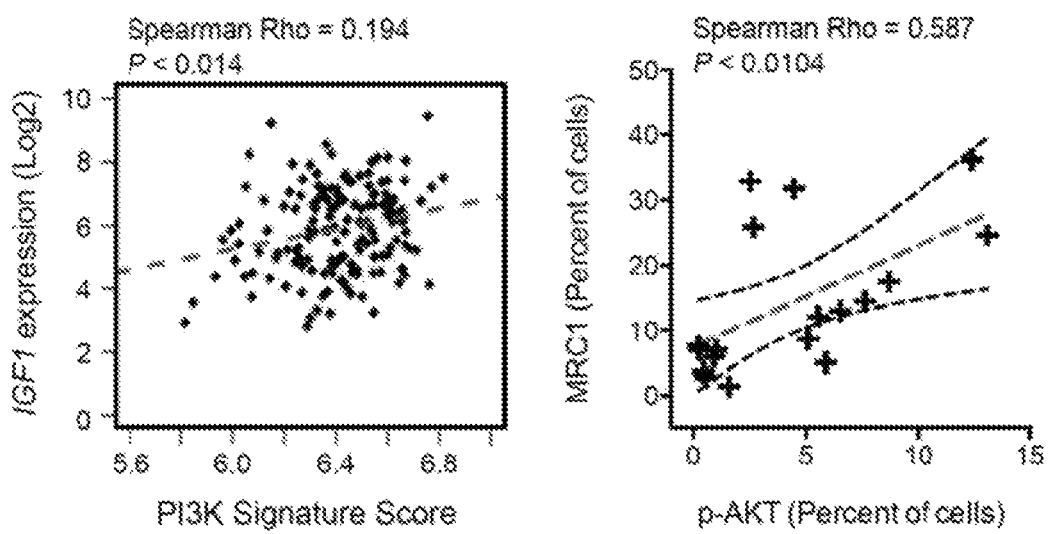
Figure 17A:
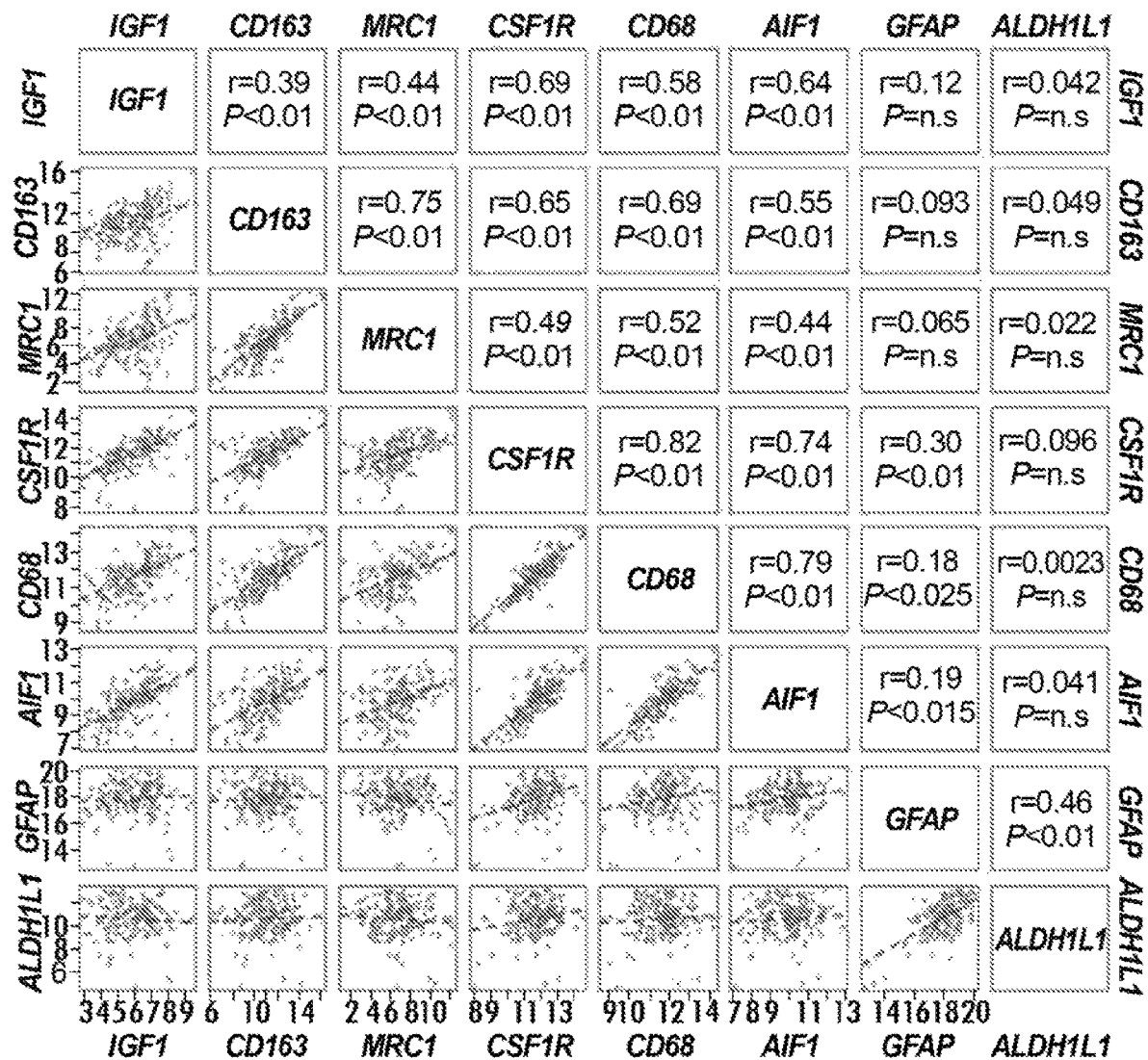
FIG. 17A-F. IGF1 expression is correlated with macrophage markers and aggressive disease in patient datasets.
Figure 17B:
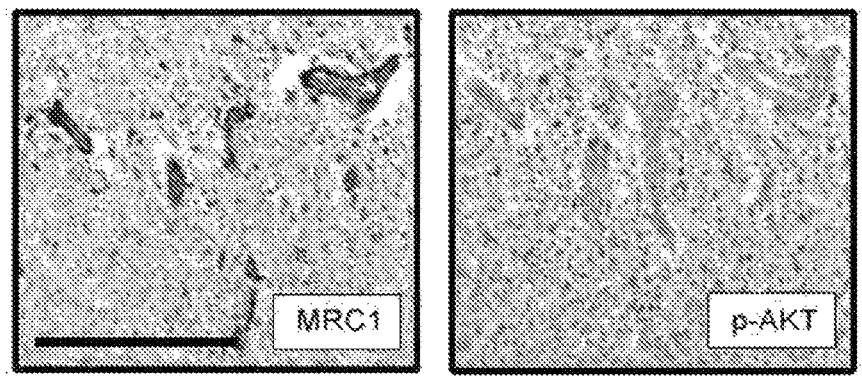

To assess the relevance of the IGF-1/IGF-1R axis in human malignancy, IGF1 expression was evaluated in publicly available human GBM gene expression datasets. It was found that IGF1 expression was significantly correlated with macrophage-specific genes (CSF1R, CD68 and AIF1) and with genes associated with an M2-like phenotype (CD163 and MRC1) in TCGA GBM samples (FIG. 5G and FIG. 17A). No such correlations were found for genes enriched in astrocytes (GFAP, ALDH1L1; FIG. 17A), another key cell type in the glial scar phenotype (18). It was also confirmed that IGF1 expression was significantly correlated with a PI3K signature score (FIG. 5H) generated from single sample gene set enrichment analysis for hallmarks of PI3K signaling (43). Consistently, IHC quantitation on an independent set of human GBM tissue samples revealed a significant association between p-AKT and the M2-associated protein MRC1 (FIG. 5I, FIG. 17B). Together these data support the hypothesis that high IGF-1 levels translate to elevated PI3K signaling in patients, and that this axis is associated with M2-like gene expression.

Figure 17C:
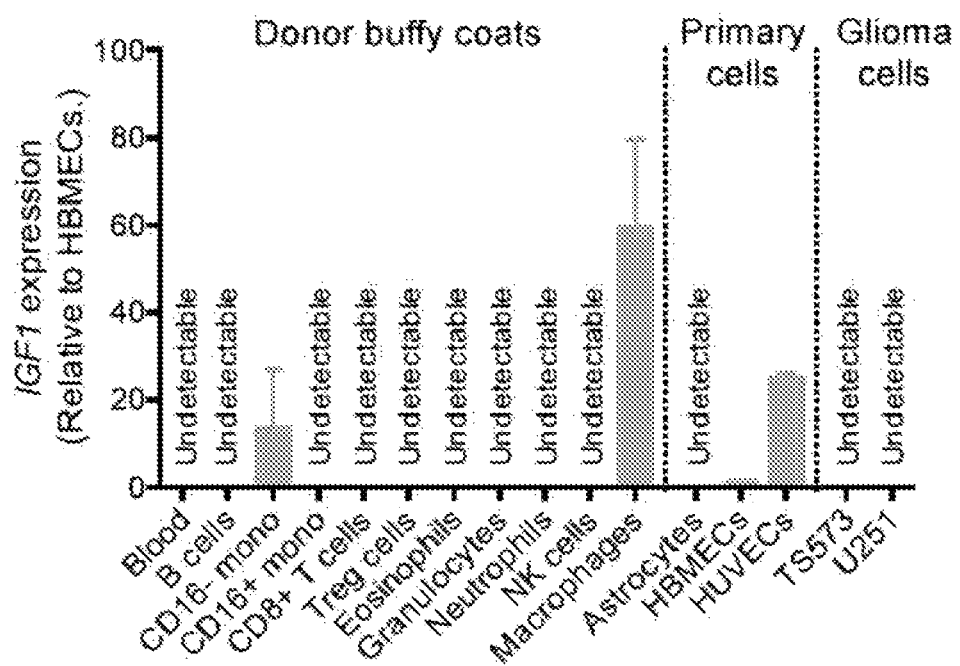
Figure 17D:
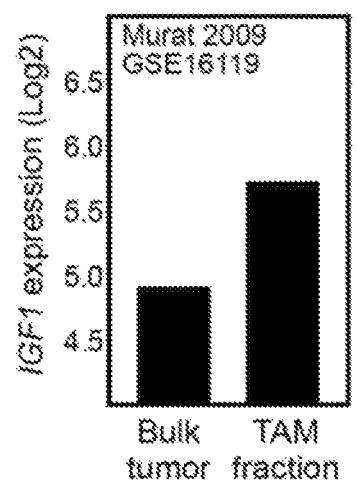
Figure 17E:
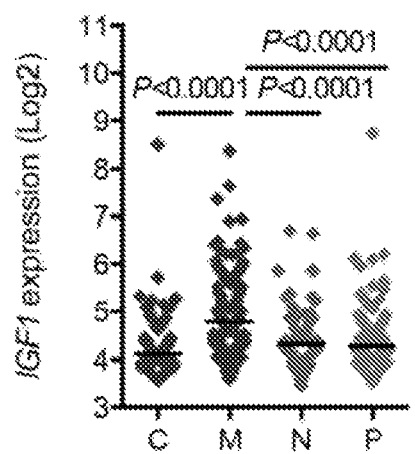

To determine if macrophages are the predominant source of IGF1 in humans, qRT-PCR was used to show that macrophages express high levels of IGF1 compared to different immune cell types, astrocytes, endothelial cells, and glioma cells (FIG. 17C). Consistently, it was found that IGF1 expression was enriched in TAMs compared to the tumor bulk in GBM (FIG. 17D) (44), and in mesenchymal GBM compared to other molecular subtypes (FIG. 17E) where high macrophage content is a hallmark histological feature. These data corroborate the findings in the PDG model and suggest that macrophages are an important source of IGF1 in human malignancy.

Figure 17F:
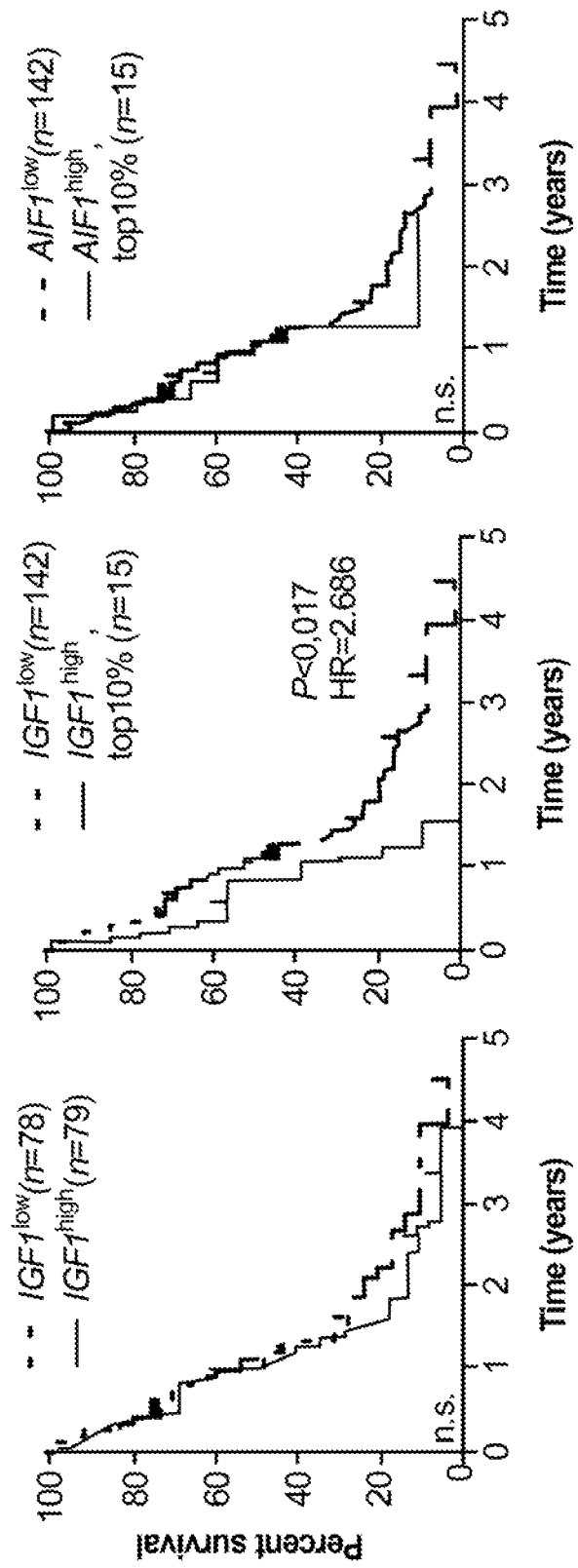

Finally, publicly available datasets were used to assess survival correlations in patients. Kaplan Meier curves were generated using a median cutoff for IGF1 expression levels, and no significant difference in overall survival between IGF1$^{high}$ and IGF1$^{low}$ patients was found (FIG. 17F). Given that baseline IGF-1 signaling is critical during normal homeostasis in the brain (41), and also the extremely rapid progression of GBM in patients, the top 10% of IGF1$^{high}$ patients (versus all remaining) was also surveyed, and a clear decrease in overall survival was found (FIG. 17F). Interestingly, when this same stringent top-10% cutoff was used for a macrophage marker (AIF1; also known as Iba1 in mouse) that correlates significantly with IGF1 expression levels (FIG. 17A), there was no separation of survival curves (FIG. 17F), suggesting that differences in survival are not simply due to differences in macrophage abundance, but rather due to differences in degree of IGF1 expression.

NFAT and Stat6 Cooperate to Regulate Igf1 Expression in Rebound TAMs

Figure 18A:
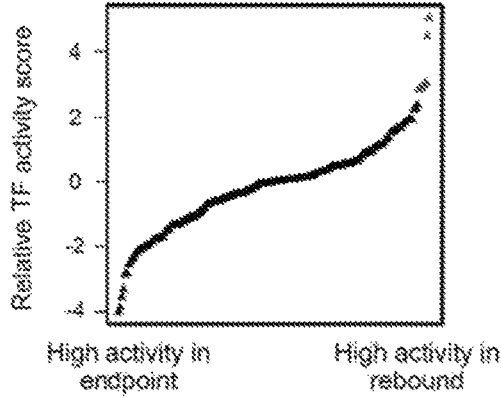
FIG. 18A-D. IL4 regulates Igf1 through NFAT and Stat6.
Figure 18B:
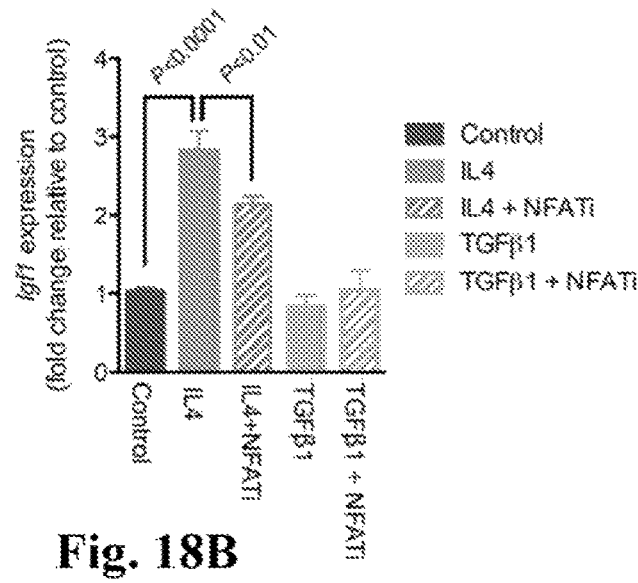

Transcription factor (TF) activity analysis was next utilized to identify putative transcriptional networks regulating Igf1 expression in rebound tumors. Seven TF families showed enriched activity in Reb TAMs compared to EP TAMs (FIG. 6A, FIG. 18A). Three of these were found to regulate Igf1 (NFAT, MYF and HMGB families; FIG. 6A), of which the NFAT family showed enriched activity specifically in Reb TAMs compared to both EP and Veh TAMs (FIG. 6B). These results were particularly interesting given the cooperative relationship between NFAT and Stat6 (canonical IL4 pathway) in transcriptional regulation (45). Corroborating these results, it was found that IL4, but not TGFβ1, induced Igf1 expression in BMDMs in vitro, which was reduced by an NFAT inhibitor (FIG. 18B).

Figure 6E:
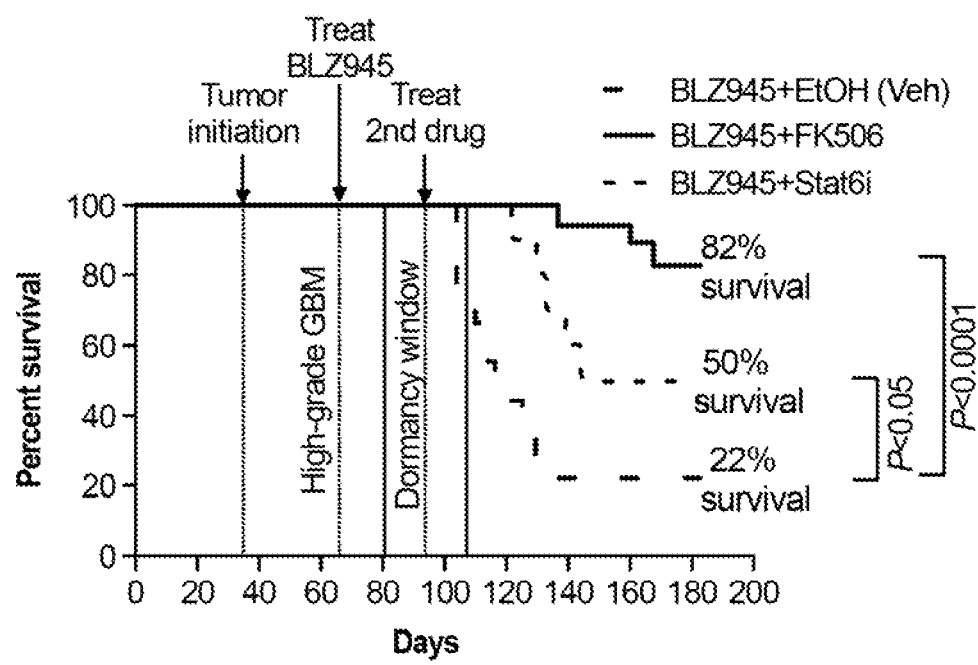
Figure 6F:
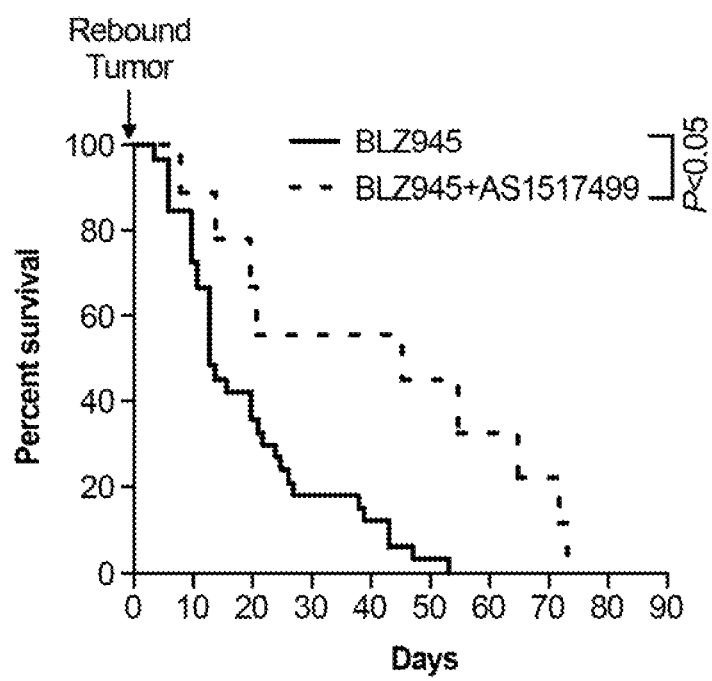
Figure 6G:
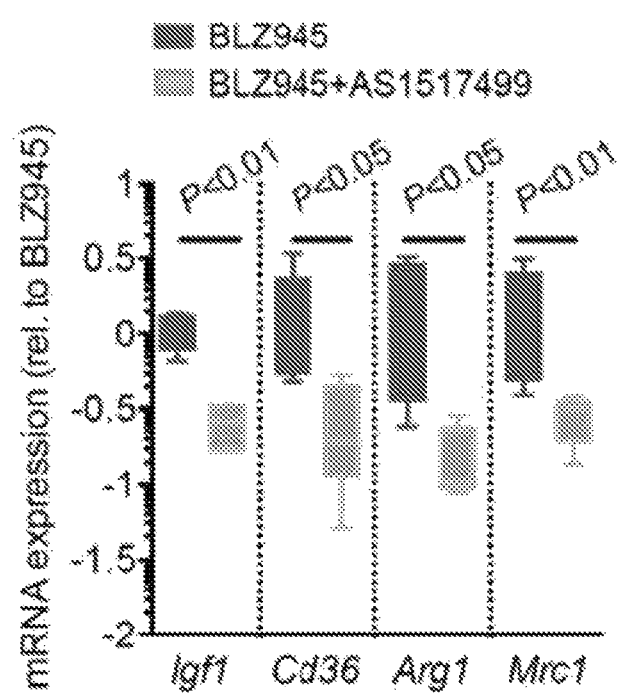
Figure 18C:
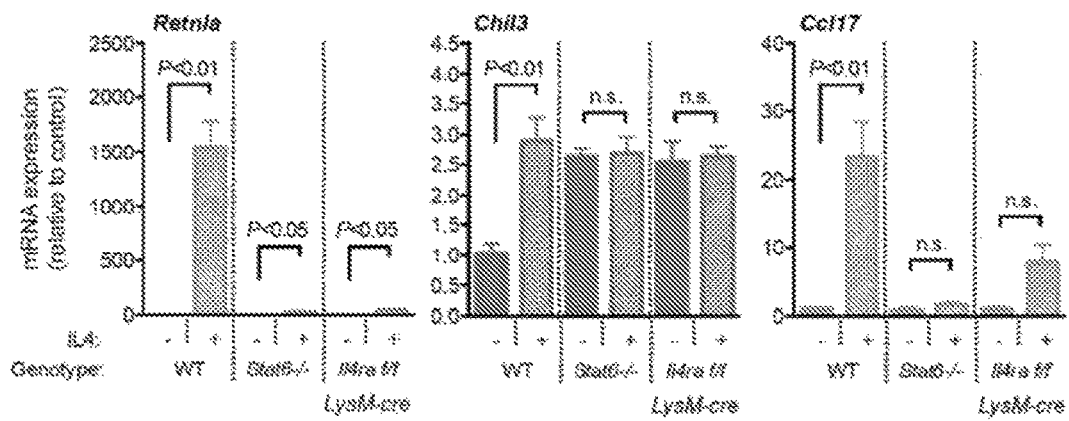
Figure 18D:
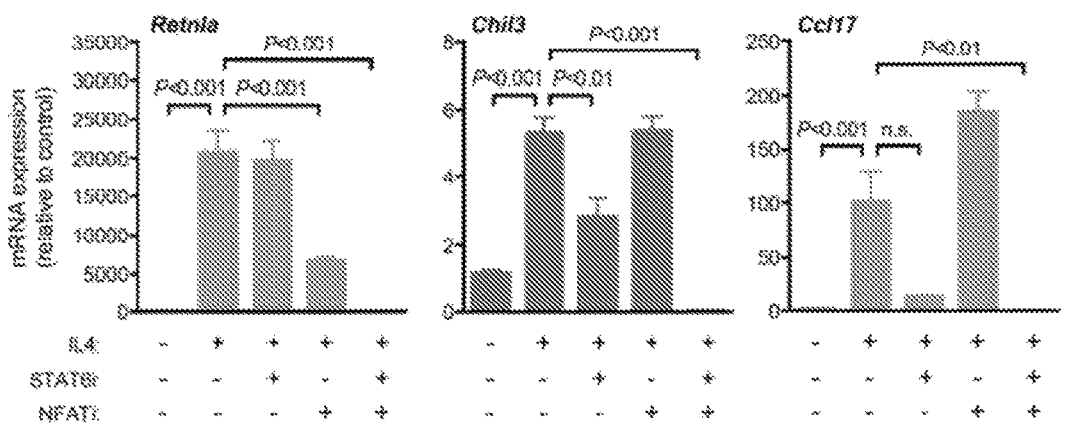

To further characterize the role of IL4-induced NFAT and/or Stat6 signaling in Igf1 regulation, a series of in vitro and in vivo experiments were performed. First, it was confirmed that IL4 strongly induced expression of Igf1 and the three representative alternative activation/wound-associated genes (Retnla, Chil3 and Ccl17) in WT BMDMs, and that this capacity was reduced in BMDMs from either Stat6−/− or Il4ra flox; LysM-cre mice (FIG. 6C and FIG. 18C). Furthermore, while pharmacological inhibition of either Stat6 or NFAT partially reversed the effects of IL4 on Igf1, Retnla, Chil3 and Ccl17 expression, dual inhibition of these pathways in WT BMDMs completely blocked the effects of IL4 on this gene set (FIG. 6D and FIG. 18D). To validate the significance of these pathways in vivo, PDG mice with high-grade GBMs were treated continuously with BLZ945 alone until 28d, at which point FK506 (a NFAT-calcineurin inhibitor) or AS Ser. No. 15/171,499 (a Stat6 inhibitor) was added until the trial endpoint. With addition of either of these inhibitors, the percentage of animals that survived to endpoint was significantly increased (22% BLZ945+Veh, 50% BLZ945+AS1517499, and 82% BLZ945+FK506; FIG. 6E). In accordance with these results, when animals were treated with AS1517499 in combination with continued BLZ945 treatment at a later time point, during the rebound phase, survival was extended (FIG. 6F), and qRT-PCR analysis of these tumors confirmed reduced levels of Igf1 expression along with additional known targets of IL4-Stat6 signaling (CD36, Arg1 and Mrc1; FIG. 6G) (27). Collectively these data suggest that both NFAT and/or Stat6 signaling contribute to macrophage activation and IGF-1 regulation in rebound tumors, and that pharmacological blockade of either of these pathways is sufficient to reduce the incidence of disease recurrence.

Combination of CSF-1R and IGF-1R Inhibition Improves Outcome

Figure 7A:
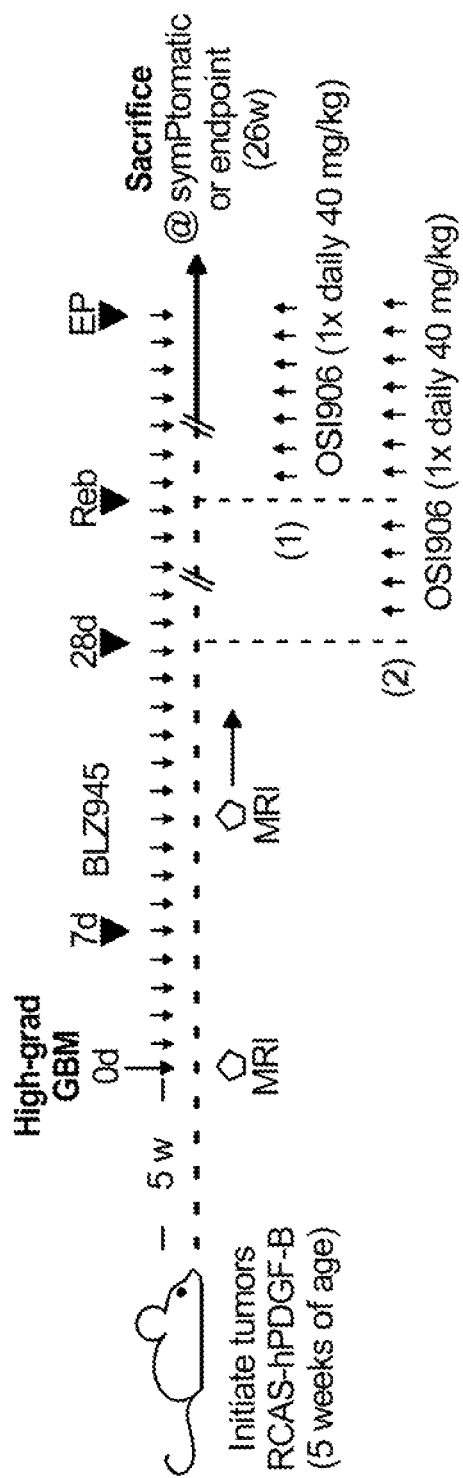
FIG. 7A-H. Combination of CSF-1R inhibition and IGF-1R inhibition significantly improves outcome in preclinical models.
Figure 7B:
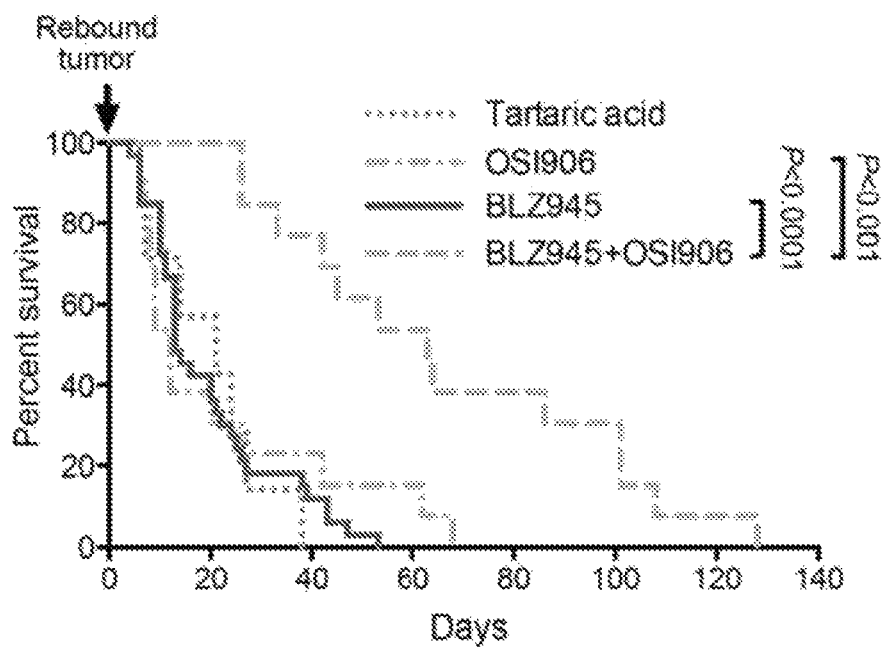
Figure 7C:
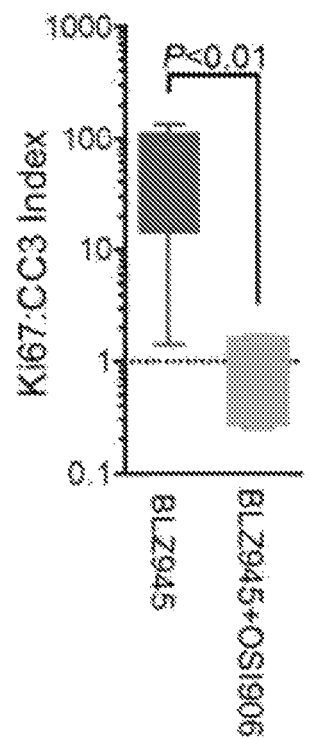
Figure 7D:
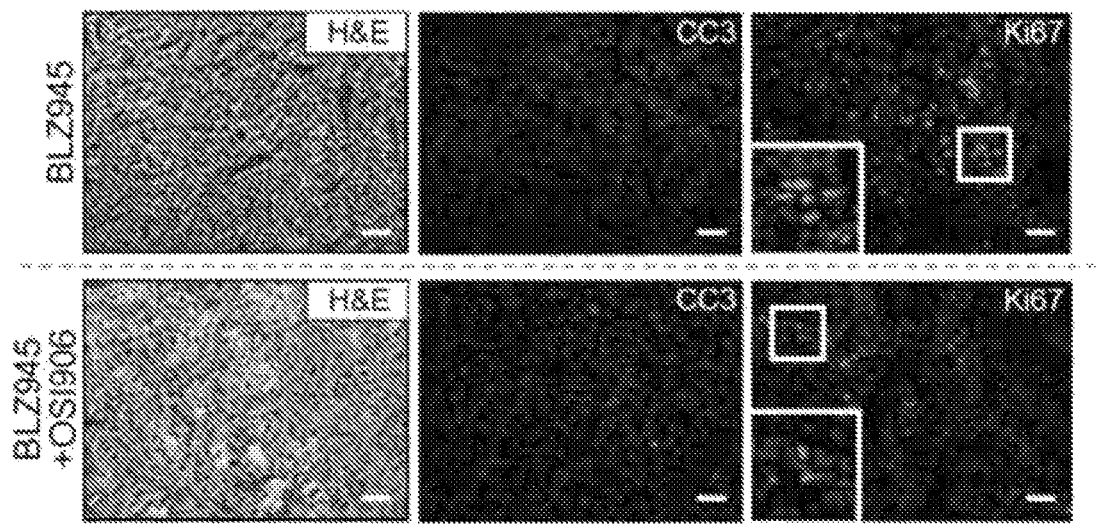
Figure 7E:
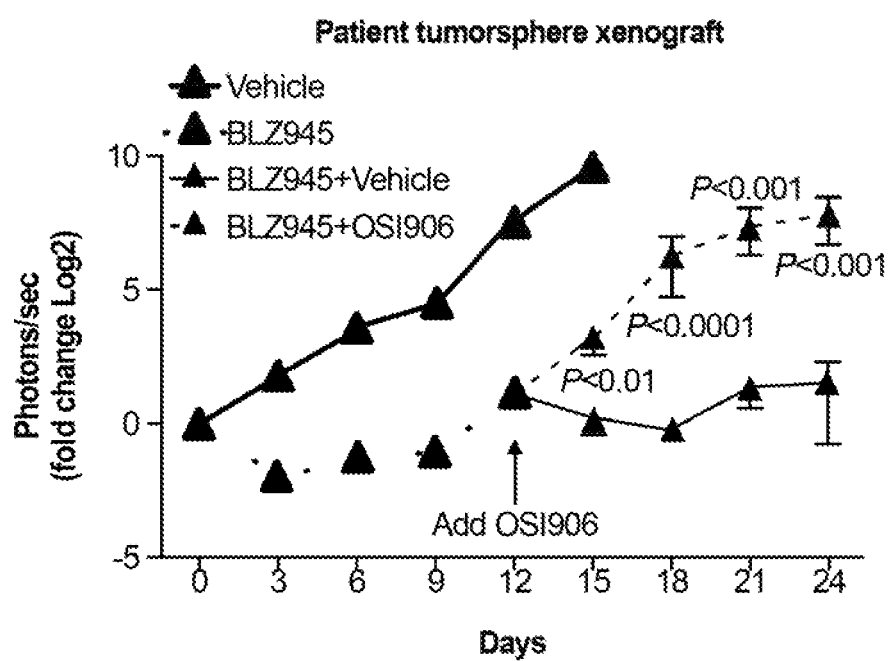
Figure 7F:
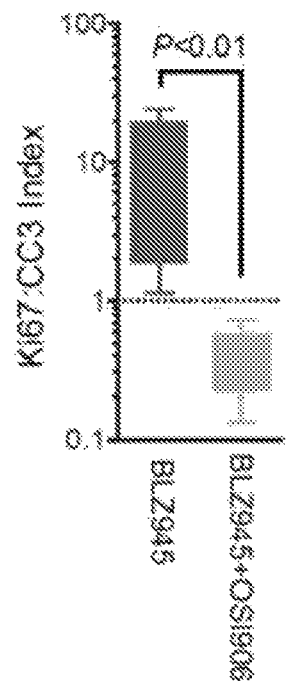
Figure 19A:
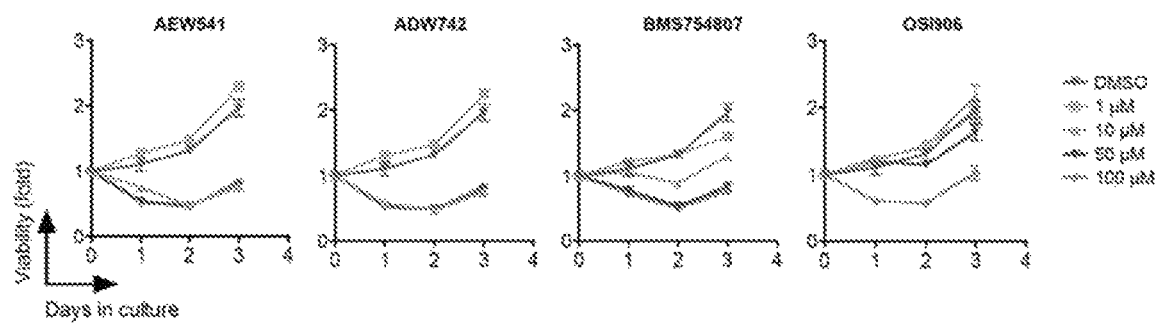
FIG. 19A-E. OSI906 blocks growth of BLZ945-resistant tumors after 2 weeks of treatment.
Figure 19B:
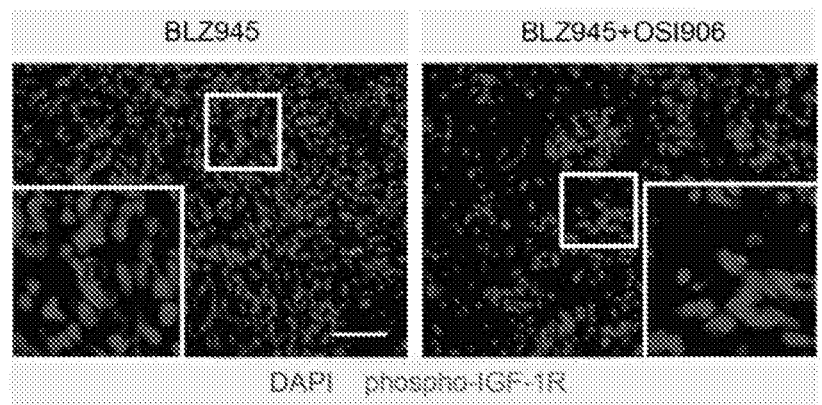
Figure 19C:
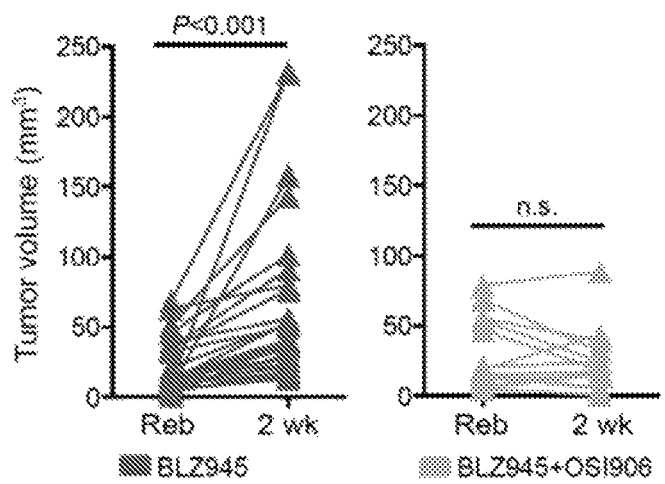
Figure 19D:
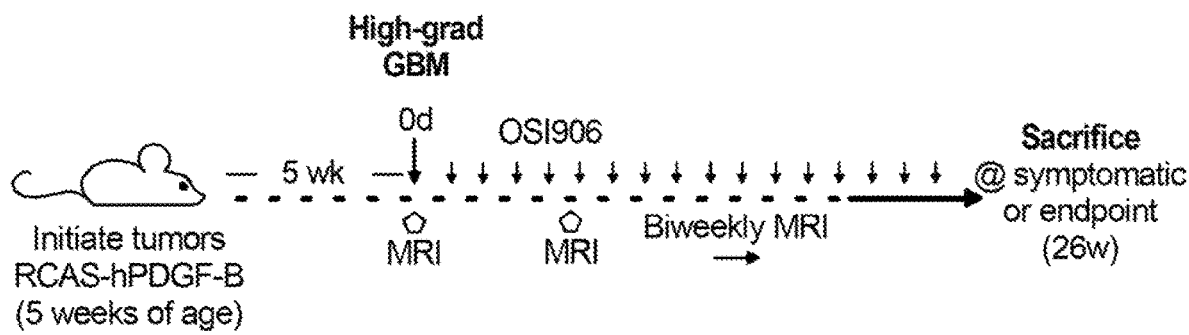
Figure 19E:
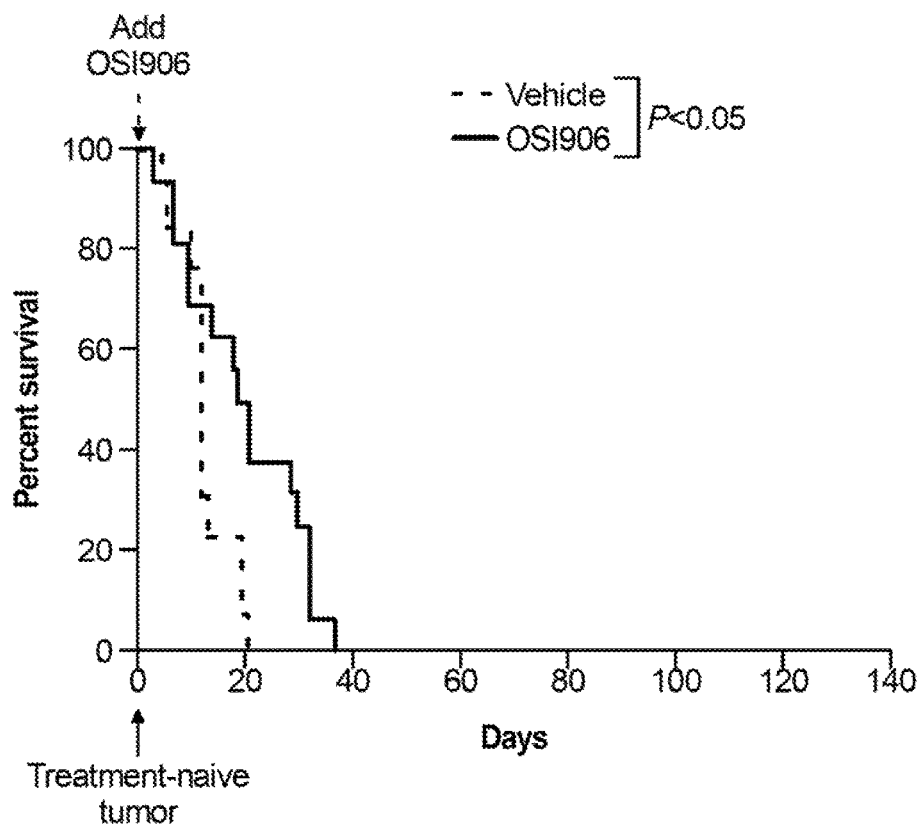
Figure 20A:
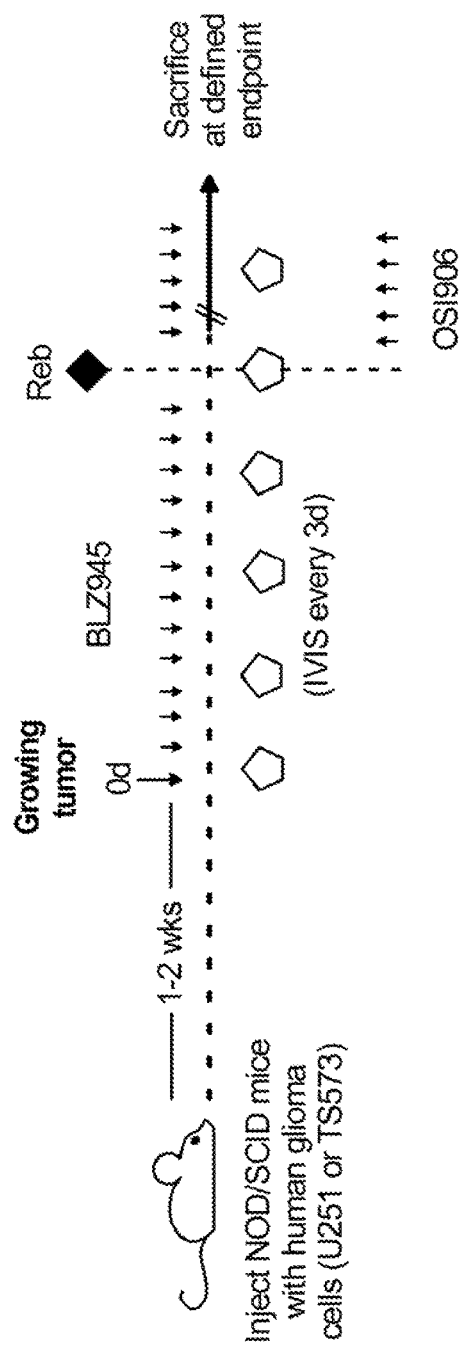
FIG. 20A-F. Blockade of IGF-1R signaling blunts growth of BLZ945-resistant orthotopic xenograft tumors.
Figure 20B:
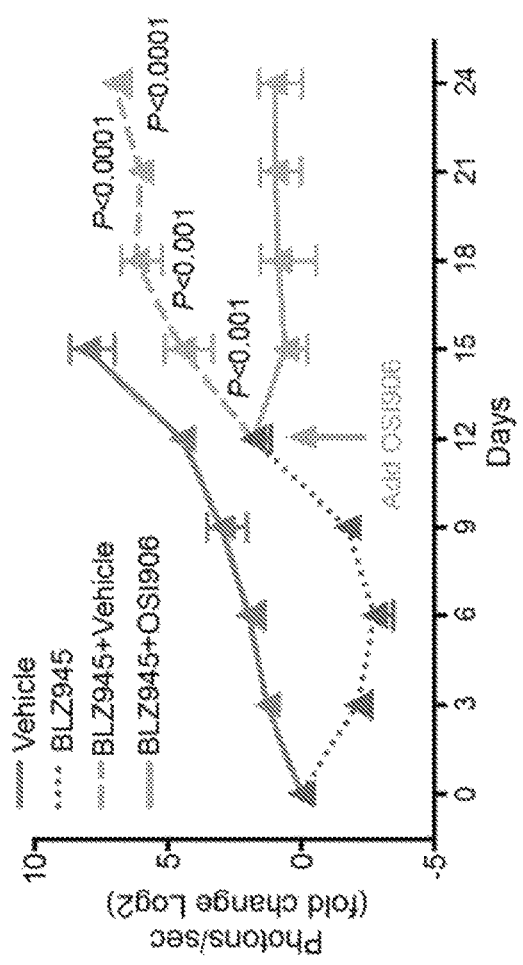
Figure 20C:
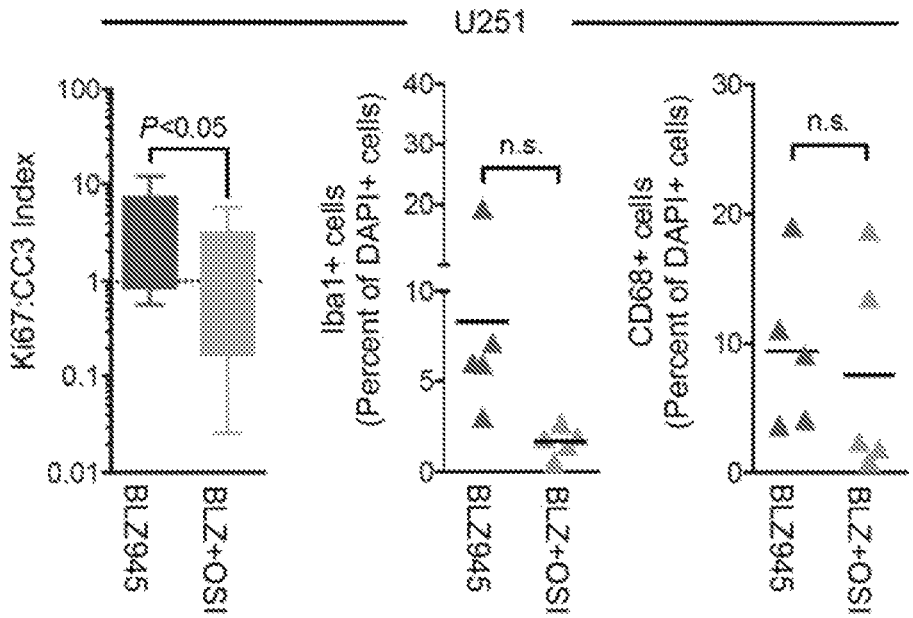
Figure 20D:
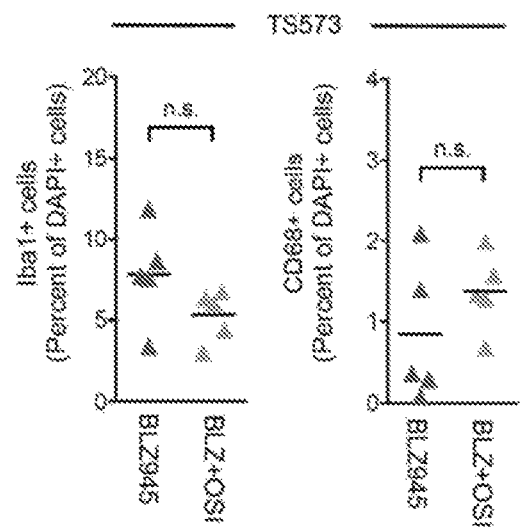
Figure 20E:
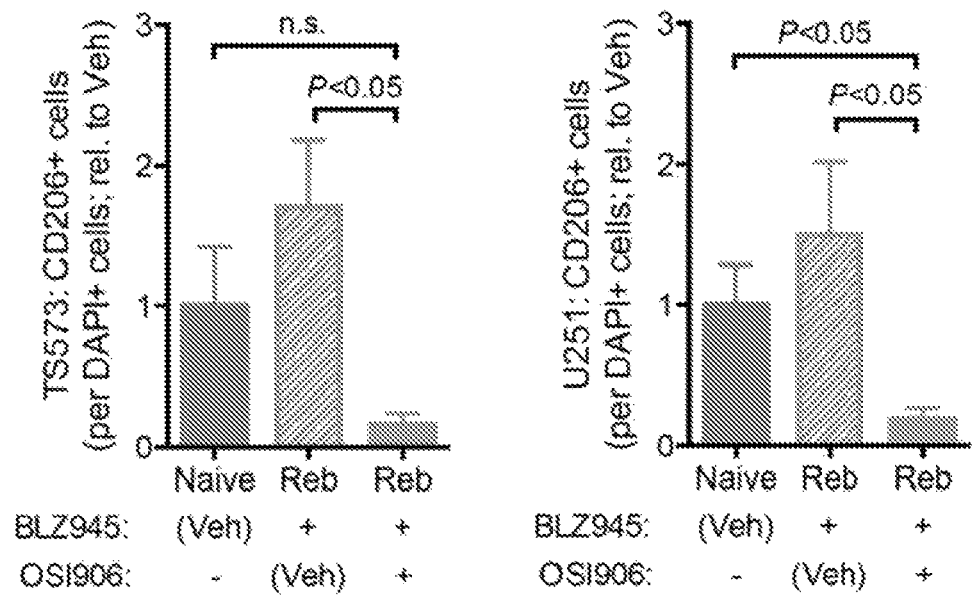
Figure 20E:
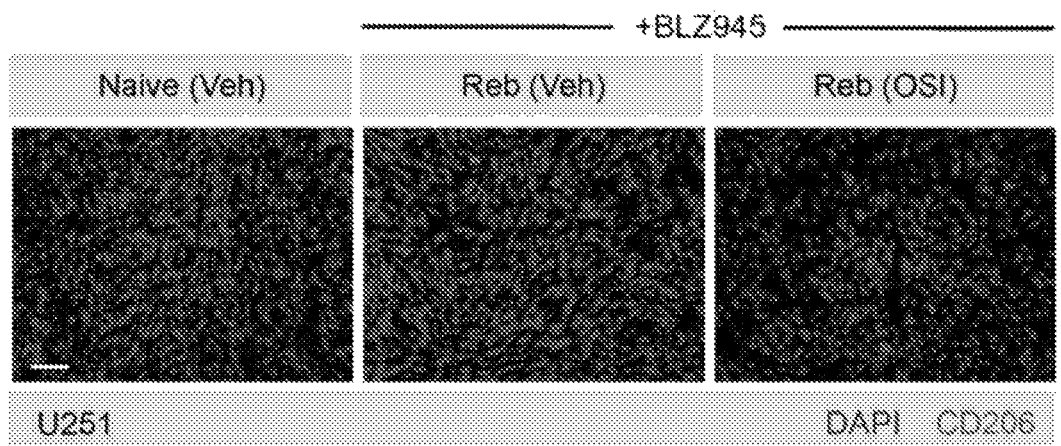
Figure 20F:
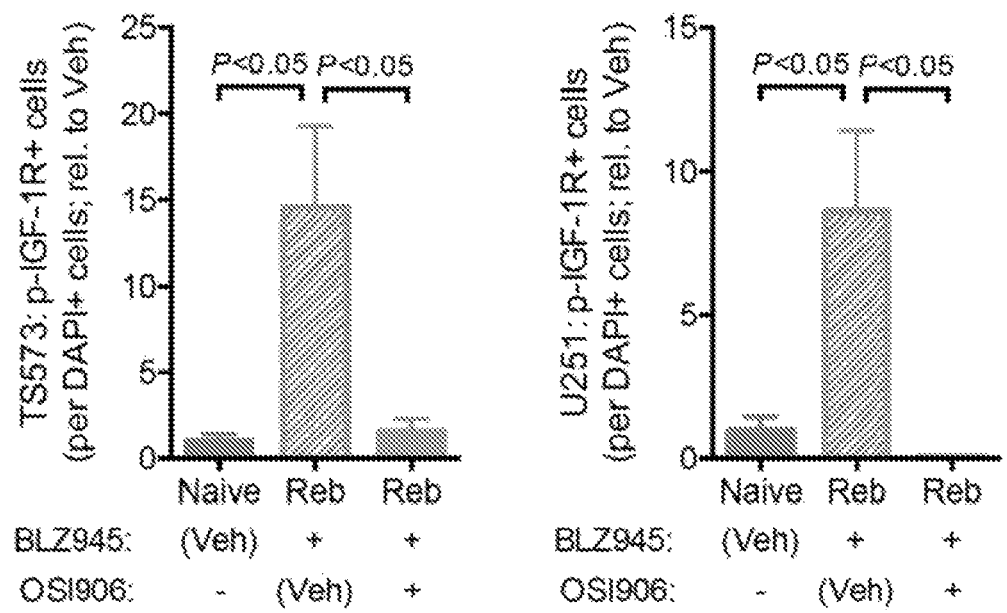
Figure 20F:
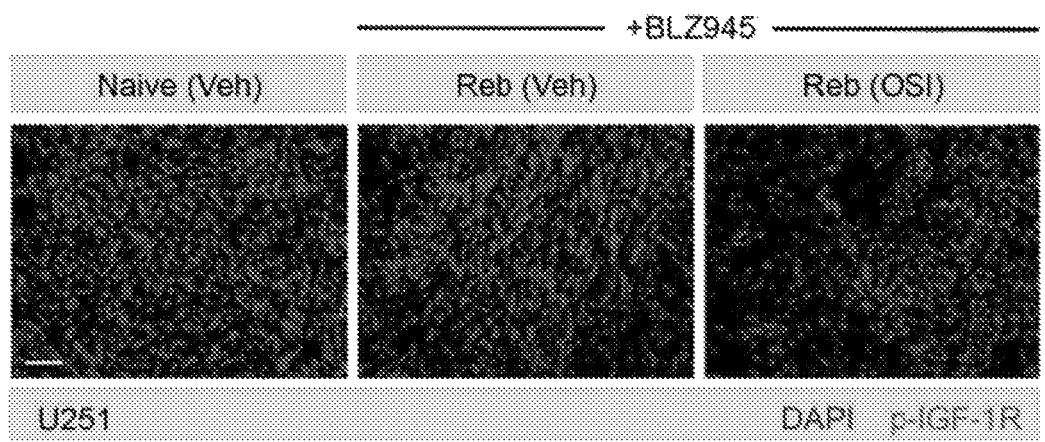

To formally test the hypothesis that the IGF-1/IGF-1R axis may underlie resistance to CSF-1R inhibition, IGF-1R was targeted in vivo using both pharmacological and genetic approaches. First, preclinical intervention trials were designed that were similar to those used for BKM120, except with an inhibitor of IGF-1R (OSI906/Linsitinib). PDG mice were treated with BLZ945 until they showed signs of rebound by MRI, at which point intervention with OSI906 was commenced (FIG. 7A, trial design 1). OSI906 was chosen because it is currently being clinically evaluated for multiple cancer types, its effect on BMDM viability in vitro was minimal compared to other IGF-1R inhibitors tested (FIG. 19A), and it was confirmed that it is brain-penetrant in rebound tumors by showing reduced p-IGF-1R immunostaining (FIG. 19B). In concordance with the BLZ945+BKM120 trial results, it was found that rebound tumors treated with OSI906 and continuous BLZ945 significantly extended median survival to 63d (versus 13d post-recurrence for continuous BLZ945 monotherapy; FIG. 7B), and markedly reduced tumor progression and proliferation: apoptosis ratios after 2 weeks of treatment (FIGS. 7, C and D, and FIG. 19C). By contrast, OSI906 monotherapy in rebound tumors (i.e. discontinued BLZ945) led to a median survival of just 12d (FIG. 7B), and was only modestly effective in treatment-naïve tumors (FIGS. 19, D and E). Together these results mirror those from the BKM120 trials, and suggest that continued CSF-1R inhibition is necessary to drive IGF1R/PI3K signaling dependency, rendering recurrent tumors sensitive to pathway inhibition. Similar combination treatment efficacy and mechanistic commonalities (including immunofluorescence quantification of Ki67: CC3 ratios, CD206, and p-IGF-1R) were observed in orthotopic xenograft trials performed with patient-derived proneural tumorspheres, and with established human glioma cell lines (FIGS. 7, E and F, and FIG. 20, A to F).

Figure 7G:
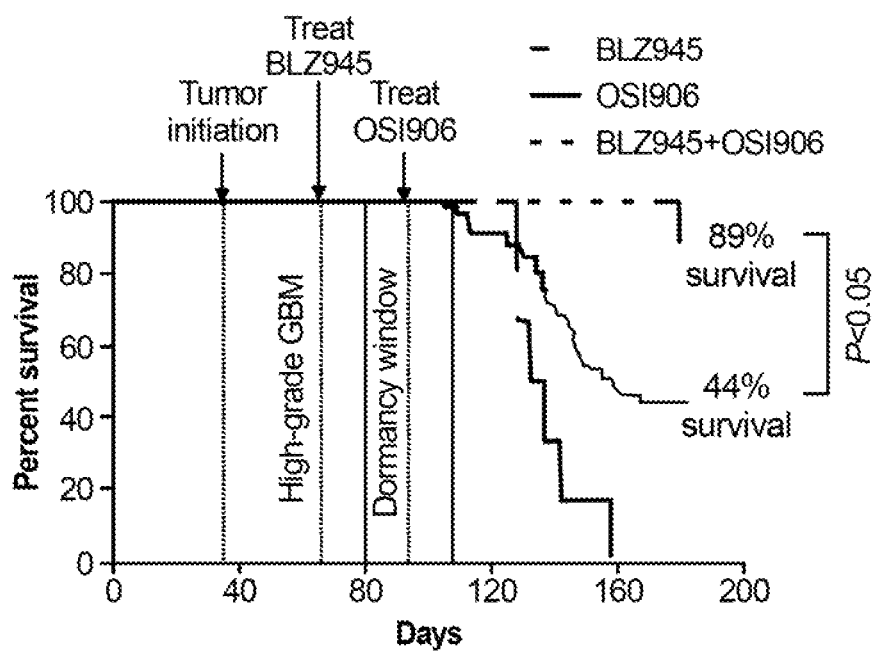

To determine if tumor outgrowth could be prevented by earlier IGF-1R inhibition, PDG mice with high-grade GBMs were treated continuously with BLZ945 alone until 28d, at which point OSI906 was added until the trial endpoint (FIG. 7A, trial design 2). With early combination treatment, overall survival was extended and the percentage of animals that survived to endpoint was increased (89% BLZ945+OSI906 versus 44% BLZ945 alone or 0% OSI906 alone; FIG. 7G). Together, these results demonstrate that targeting either IGF-1R or PI3K signaling in GBMs resistant to CSF-1R inhibition can interfere with disease progression and improve overall survival.

Figure 7H:
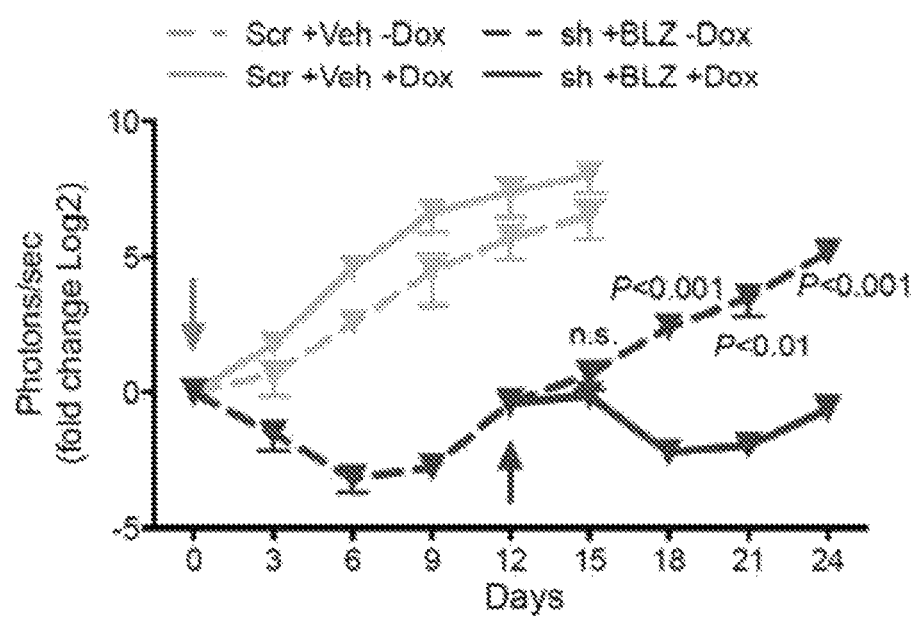
Figure 21A:
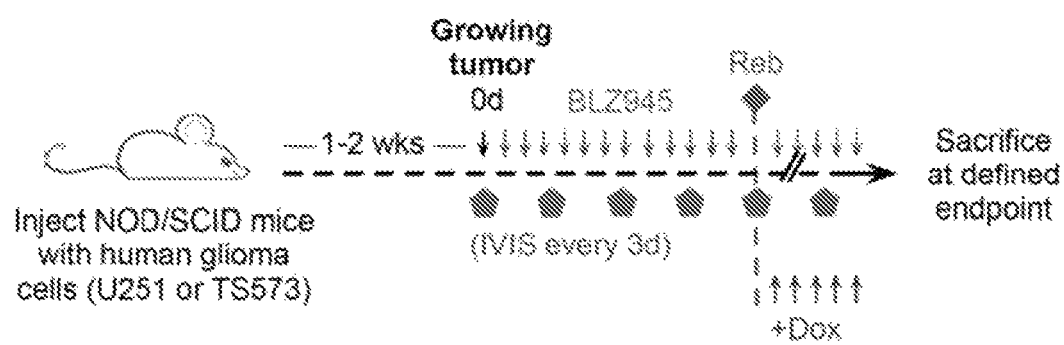
FIG. 21A-E. Inducible knockdown of IGF1R in tumor cells blunts BLZ945 resistance.
Figure 21B:
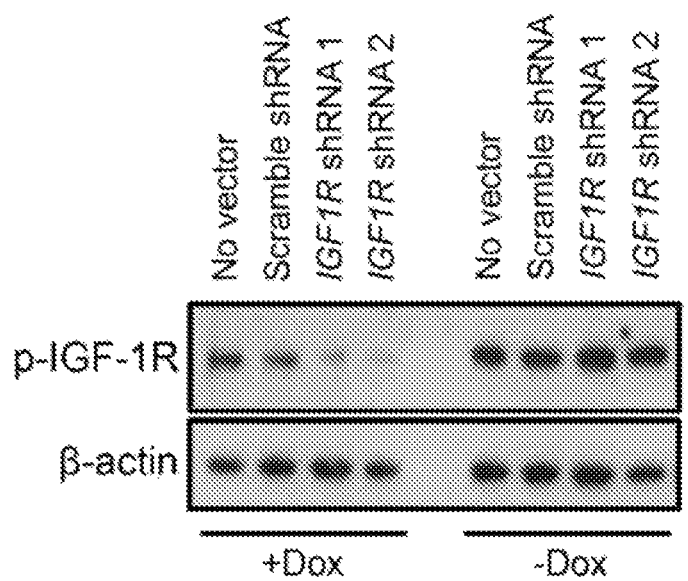
Figure 21C:
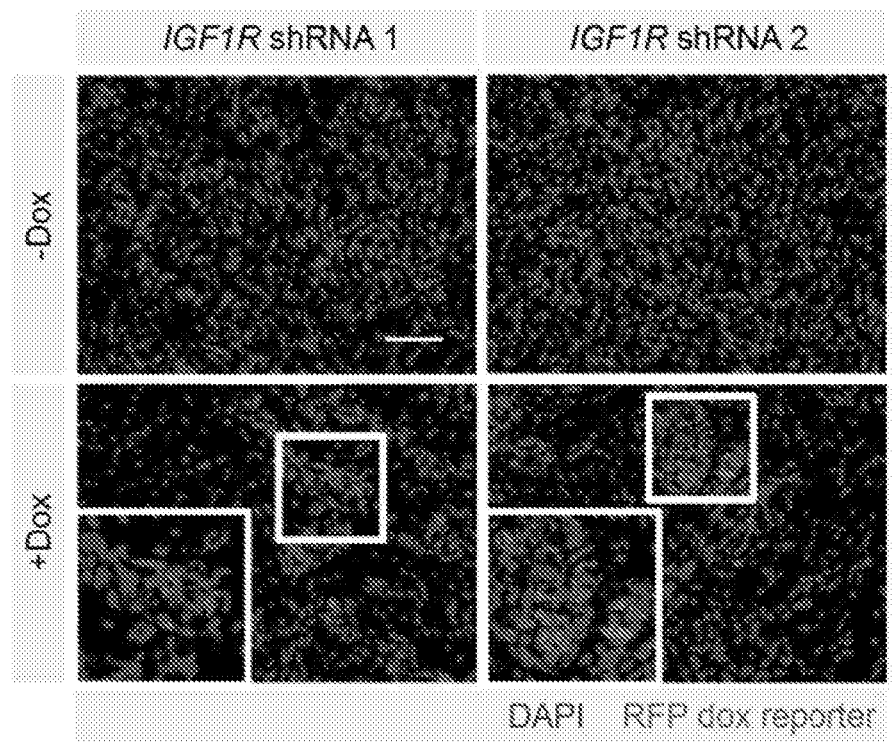
Figure 21D:
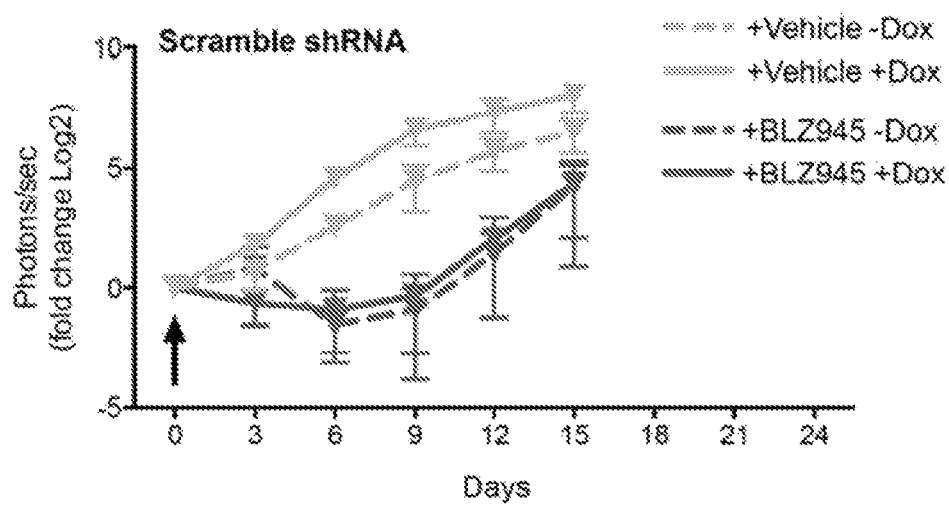
Figure 21E:
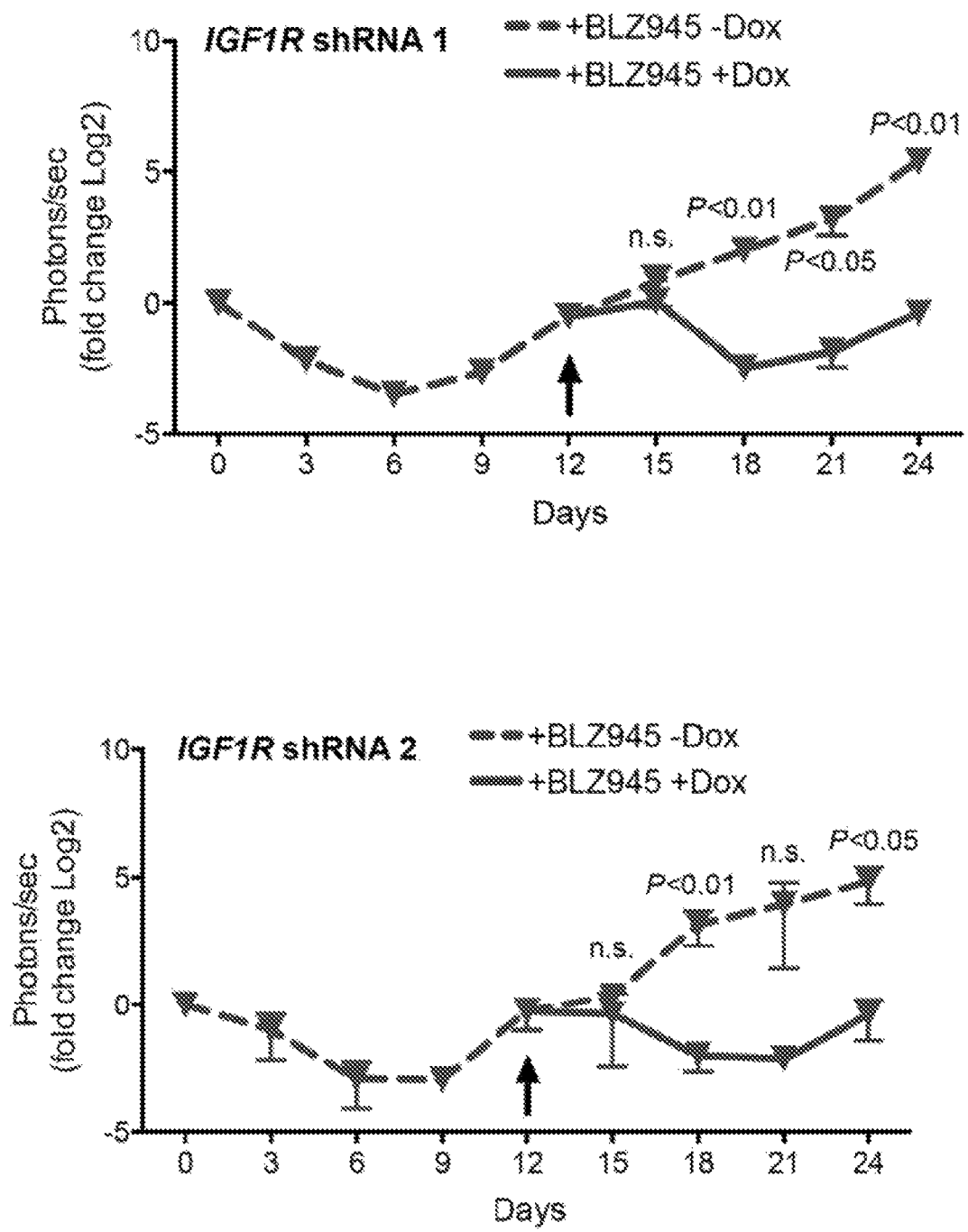

Given that pharmacological inhibition of IGF-1R using OSI906 cannot confirm whether tumor cell-specific blockade is sufficient to reduce recurrent disease, a genetic approach was utilized to target this receptor in glioma cells. U251 glioma cell lines were genetically engineered to express a doxycycline-inducible shRNA against IGF1R, and orthotopic xenograft experiments were performed (see FIG. 21A for trial design). Two independent shRNAs targeting IGF1R were used, and a scramble-sequence shRNA was used as a control (FIG. 21, B to D). It was found that, in both cases, dox-induction of the shRNAs during the rebound phase of the trial (d12) mitigated tumor progression compared to no-dox control animals (FIG. 7H, and FIG. 21E). These results support the hypothesis that tumor cell-specific IGF-1R contributes to BLZ945 resistance and disease recurrence.

Discussion

This Example demonstrates, and elucidates the mechanisms underlying, the development of acquired resistance to CSF-1R inhibition in mouse models of GBM. While initial therapeutic response to CSF-1R inhibition is robust, rapid, and completely penetrant, it has been shown herein that approximately half of the animals eventually develop resistance, with rapidly progressing rebound tumors. In light of recent results from ongoing patient studies with CSF-1R inhibitors in glioma (46) and other cancers, these findings suggest the need to prepare for the emergence of therapeutic resistance to CSF-1R inhibitors in GBM in the clinical setting, and determine if other brain malignancies besides GBM will respond similarly to CSF-1R inhibition. While classical mechanisms of tumor cell-intrinsic resistance to cytotoxic and targeted agents have been well-defined, including aberrant drug metabolism and transport, drug target mutation, and activation of alternative survival pathways (47), it still remains unclear whether resistance to TME-directed therapies will follow similar principles. Given that TME-targeted agents are increasingly being evaluated in the clinic (1, 2), it will be critical to mechanistically define how resistance evolves in response to these therapies in order to provide long-term disease management for patients.

Figure 8:
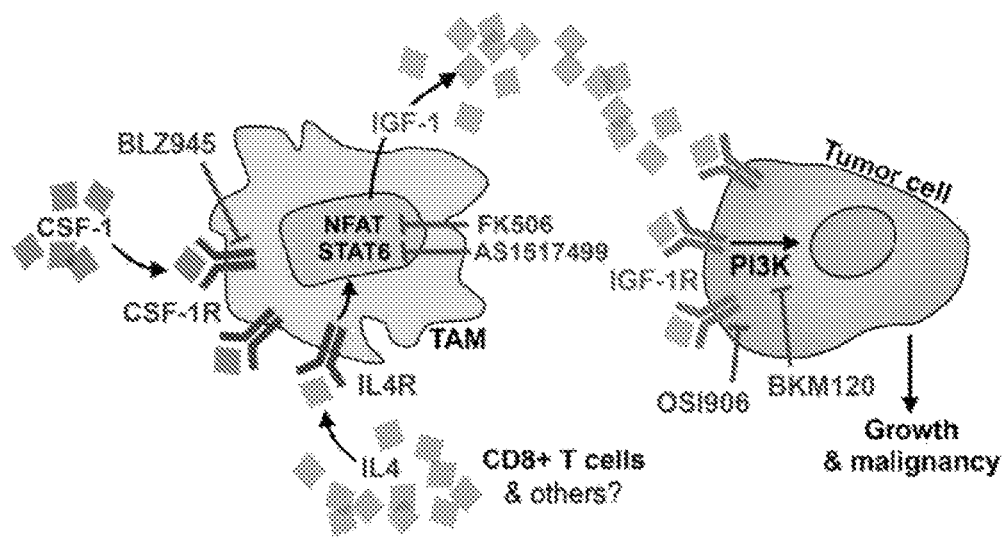
FIG. 8. Working model for mechanism of resistance to CSF-1R inhibition in glioma. IGF-1 is significantly upregulated in TAMs in response to long-term CSF-1R inhibition in GBM. IGF-1 secretion into the extracellular environment results in activation of IGF-1R on tumor cells, and downstream PI3K signaling to support tumor regrowth during continuous BLZ945 treatment. Upstream of IGF-1 in TAMs, NFAT and/or Stat6 transcriptional activity regulate its expression. This is thought to be initiated in response to IL4/IL4Ra pathway activation, feeding in from other cell types in the TME, including T cells (and possibly others). Multiple nodes in this signaling loop can be targeted therapeutically, including OSI906, BKM120, AS1517499, or FK506, resulting in a substantial improvement in survival in preclinical trials when combined with CSF-1R inhibition.

In light of this problem, the present Example identifies a mechanism of drug resistance that can circumvent therapeutic response to a TME-targeted therapy, and promote disease progression in the absence of tumor cell-intrinsic alterations. Specifically, the work presented herein demonstrated a heterotypic paracrine signaling interaction that is initiated by the TME, and that drives resistance to CSF-1R inhibition. In rebound tumors, it was found that IGF-1 is upregulated in TAMs in response to IL4 (possibly supplied by T cells or alternative cell types), in part via NFAT activation. IGF-1 secretion into the extracellular environment results in activation of IGF-1R and PI3K signaling in glioma cells, supporting tumor growth and malignancy (see model in FIG. 8). Multiple nodes in this signaling loop can be targeted therapeutically by agents that are currently used clinically, including OSI906, BKM120, or FK506, resulting in a substantial improvement in survival in the preclinical setting when combined with CSF-1R inhibition. Indeed, given that PI3K signaling is aberrantly activated in a substantial proportion of GBM patients (16), and recent clinical trial results showing limited efficacy in recurrent (albeit very advanced) GBM (46), it is possible that this pathway could similarly contribute to intrinsic resistance to CSF-1R inhibition, and consequently those patients may benefit from combinatorial inhibition of these pathways from the outset.

Importantly, the findings presented herein underscore the importance of bidirectional feedback between cancer cells and their microenvironment, and support the notion that while stromal cells are less susceptible to genetic mutation than cancer cells, a tumor can nonetheless persist by exploiting its extracellular environment to acquire a resistant phenotype. Thus, an integrated analysis of cancer cells with their microenvironment can be helpful in understanding both their parallel evolution during tumor progression, and their capacity for adaptation in the context of therapeutic intervention and the development of resistance.

Materials and Methods

Study Design.

The overall objective of these studies was to understand how resistance to CSF-1R inhibitors develops in high-grade glioma using various in vivo and in vitro models. Within the animal studies, mice were randomly assigned to different therapy groups, which included treatment with BLZ945 (a CSF-1R inhibitor) in combination with inhibitors of putative resistance pathways (e.g. IGF-1R or PI3K), versus single-agent or vehicle controls. Survival and disease progression were monitored using a combination of MiII, histology, flow cytometry, and gene expression analyses throughout all trials. To power these studies, sample size was predefined as at least n=3 independent experiments, replicates or samples for in vitro and in vivo experiments, and up to a maximum of n=90 mice for survival analyses. Replicate values are indicated for each experiment in the figure legend. All analyses were calculated in a blinded manner through numerical coding of samples. For all long-term survival trials, 26 weeks was selected as a predefined endpoint because mice in the Ink4a/Arf background develop spontaneous lymphomas and sarcomas beginning at ~30 weeks of age. For in vivo trials, mice were considered outliers if they developed (i) spontaneous lymphomas (given this disposition in the Ink4a/Arf$^{-/-}$ background), (ii) early symptoms of tumor burden >1 week prior to trial enrollment, or (iii) development of hydrocephalus prior to trial enrollment.

Biologicals and Pharmaceuticals (Active Agents).

BLZ945 (Novartis) (8) was used for both in vitro and in vivo studies. 6,700 nM of BLZ945 was used for all in vitro experiments in tumor cells, versus an equal percent DMSO as a vehicle control. This concentration represents 100× the IC50 for BLZ945 in macrophages (8). For in vivo experiments, BLZ945 was obtained pre-formulated at 12.5 mg/ml. BLZ945 was administered p.o. 1× daily at 200 mg/kg, and 20% Captisol was used as a vehicle control. BKM120 (Buparlisib; 1 µM unless indicated otherwise), AEW541, ADW742, BMS754807 and OSI906 (Linsitinib; 10 µM unless indicated otherwise) (all from Selleckchem) were used in vitro up to 100 µM for dose response assays versus an equal percent DMSO as a vehicle control. BKM120 and OSI906 (ChemieTek) were used in vivo. BKM120 was formulated by dissolving 52 mg into 500 ml NMP, boiling, and then adding 9.5 ml of PEG300. BKM120 was administered p.o. 1× daily at 20 mg/kg, and NMP:PEG300 (1:19) was used as a vehicle control. Animals were dosed at 20 mg/kg to avoid off-target effects, as BKM120 binds tubulin at concentrations above 50 mg/kg in subcutaneous tumor models, but not below 40 mg/kg (15). OSI906 was formulated daily at 4 mg/ml in 25 mM tartaric acid with shaking and sonication for ~15 min. OSI906 was administered p.o. 1× daily at 40 mg/kg, and 25 mM tartaric acid was used as a vehicle control. It was decided to treat at 40 mg/kg as the maximum tolerated dose for OSI906, 75 mg/kg (48), was found to be toxic within 4 days in these studies. For all combination trials, BLZ945 was administered in the morning, and BKM120 or OSI906 was administered in the evening. The NFAT inhibitor, INCA-6 (Tocris) was used at a concentration of 40 µM for in vitro use (49). For in vivo inhibition of NFAT signaling, FK506 was used to inhibit the activating interaction between calcineurin and NFAT, at a dose of 10 mg/kg (administered i.p. every 3 days) (50). The Stat6 inhibitor, AS1517499 (Axon Medchem) was used at a concentration of 50 nM for in vitro use, and dosed at 10 mg/kg for in vivo use (administered i.p. 2× weekly) (51). The vehicle control for FK506 and AS1517499 in vivo was 10% EtOH and 1% Tween-80 in PBS. For in vitro PCR assays, recombinant mouse IL4 (R&D Systems) was used at a concentration of 10 ng/ml, recombinant mouse TGFβ1 (R&D Systems) was used at a concentration of 50 ng/ml, and the TGFβ1 type 1 receptor inhibitor, SB431542 (Tocris), was used at a concentration of 10 µM. For ex vivo glioma microenvironment culture (GMEC) assays, a neutralization antibody against IGF-1 (R&D Systems) was used at a concentration of 0.5 µg/ml. For culture of macrophages in vitro, recombinant mouse CSF-1 was used at a concentration of 10 ng/ml. For in vitro assays using bone marrow-derived macrophages (BMDMs), CSF-1 supplementation was excluded from all experimental conditions.

Animals.

Crl:NU(NCr)-Foxn1$^{nu}$ immunodeficient mice (Charles River Laboratories) were used for orthotopic transplantation studies. NOD/CB17-Prkdc$^{scid}$ immunodeficient mice (The Jackson Laboratory) were used for orthotopic implantation of human cells. Three different transgenic mouse models expressing the avian tv-a receptor under the control of the nestin (N) promoter in either mixed strain or BL6 backgrounds were used (Ntv-a; Ink4a/Arf$^{-/-}$, Ntv-a, and Ntv-a; Pten$^{flox}$), all previously described (13, 52-57). Stat6$^{-/-}$, Il4ra$^{flox}$; LysM-cre, and wild-type (WT) C57BL/6 (BL6) mice were used for bone marrow isolations. All animal studies were performed after obtaining the necessary approvals.

PDG Mouse Model.

The initiation of PDGF-driven gliomas (PDG) with RCAS-hPDGF-B-HA in adult mice has been previously described (8, 13, 58). Briefly, Ntv-a; Ink4a/Arf$^{-/-}$ mice were fully anesthetized with ketamine/xylazine prior to surgery. Pain management included a 50 µl subcutaneous injection of bupivacaine (0.25%) at the surgical site prior to surgery, and an intraperitoneal injection of buprenorphine immediately following surgery. Mice were intracranially injected with DF-1:RCAS-hPDGF-B-HA cells (200,000 cells/1 µl) between 5-6 weeks of age using a fixed stereotactic apparatus (Stoelting). Injections were made into the right frontal cortex, approximately 1.5 mm lateral and 1 mm caudal from bregma, and at a depth of 2 mm into the subventricular zone (SVZ). In this model, injection into the SVZ induces tumors with low latency (4-5 weeks), 100% penetrance, and histological features characteristic of patient GBM including microvascular proliferation and pseudopalisading necrosis (13). The incision was sealed using Vetbond tissue adhesive (3M). Tumors were imaged by MRI after 5 weeks, and drug intervention was initiated for tumors ≥2 mm$^3$. A total of 90 animals were treated in long-term experiments with BLZ945 alone, which represented 5 independent cohorts. These data are compiled and presented in FIGS. 1D, 2E, and 7G.

p53 KD Mouse Model.

Injections were performed as described for the PDG mouse model above, except Ntv-a mice were used (i.e. WT Ink4a/Arf). Mice were intracranially injected with a 1:1 ratio of DF-1:RCAS-hPDGF-B-HA cells and DF-1:RCAS-shp53 cells (total of 300,000 cells/2 □l) between 5-6 weeks of age. Injection into the SVZ in the p53 knockdown (KD) model induces high-grade tumors with low latency (6-7 weeks), 100% penetrance, and histological features of human GBM (13, 54, 55). Tumors were detected by MIII after 6-7 weeks, at which point drug intervention with BLZ945 was initiated (see FIG. 2F).

Pten KO Mouse Model.

Injections were performed as described for the PDG mouse model above, except Ntv-a; Pten$^{flox}$ mice were used (i.e. WT Ink4a/Arf). Mice were intracranially injected with a 1:1 ratio of DF-1:RCAS-hPDGF-B-HA cells and DF-1:RCAS-Cre cells (total of 300,000 cells/2 µl) between 5-6 weeks of age. Injection into the SVZ in the Pten knockout (KO) model induces tumors with moderate latency (8-12 weeks) and penetrance (~20-30%). Tumors that form harbor key characteristics of human GBM including highly infiltrative histology (13, 54, 56, 57). Tumors were detected by MIII after 8-12 weeks, at which point drug intervention with BLZ945 was initiated (see FIGS. 2, F and G).

Derivation of Mouse Primary Glioma Cell Lines from PDG Tumors.

To derive rebound or dormant cell lines from BLZ945-treated PDG tumors, MRI was used to confirm whether a particular tumor was in rebound or dormancy phase. Macrodissected rebound or dormant lesions from the BLZ945-treated PDG mouse model were manually dissociated and filtered through a 40 µm mesh filter. The cell suspension was washed 2× with PBS, and cultured in Mouse Neural Stem Cell (mNSC) Basal Media (Stem Cell Technologies) containing mNSC proliferation supplement, 1 mg/ml Heparin (Stem Cell Technologies), 10 ng/ml recombinant epidermal growth factor (rEGF; Invitrogen), and 20 ng/ml recombinant basic-fibroblast growth factor (rbFGF; Sigma). To generate cell lines in monolayer, tumorsphere cultures were expanded and dissociated, and transferred to culture with DMEM+10% FBS (59). In total, 5 rebound cell lines were derived (89AReb, 89BReb, 74Reb, 48Reb, 52Reb), and 1 cell line was derived from the 28d dormant timepoint. The 28d dormant cells (FIG. 16G) took several weeks before starting to proliferate in culture, and upon transplantation into naïve animals, the cells did not give rise to growing tumors (BLI signal remained stable and was monitored up to 22d; data not shown). Derivation of the PDGC23 primary glioma cell line from an untreated/naïve mixed-background PDG mouse was described previously (8).

Human Cell Lines.

Human umbilical vein endothelial cells (HUVEC) were obtained from ATCC. Human brain microvascular endothelial cells (HBMEC) and human astrocytes were purchased from Sciencell. Astrocytes were cultured on poly-L-lysine-coated plates, and both HUVECs and HBMECs were cultured on gelatin-coated plates with endothelial cell media (ECM, Sciencell)+10% FBS+an endothelial cell growth factor supplement. The U251 (commercially available) and TS573 (patient-derived) cell lines were selected based on previously published work, which showed efficacy in response to BLZ945 in orthotopic xenograft trials (8). The patient-derived TS573 glioma tumorsphere line was derived from a consenting patient under Institutional Review Board (IRB)-approved protocols for the banking of excess tumor tissue during routine surgical resection, as previously described (8, 60). Tumorspheres were maintained in Human Neural Stem Cell (hNSC) Basal Media (Stem Cell Technologies) containing hNSC proliferation supplement, 1 mg/ml Heparin (Stem Cell Technologies), 10 ng/ml rEGF (Invitrogen), and 20 ng/ml rbFGF (Sigma). Tumorspheres were passaged by dissociation with Accutase cell detachment solution (Millipore). Characterization and molecular subtyping by Sequenom, Nanostring and aCGH were performed as previously described (8). Briefly, aCGH on primary spheroids showed a high level amplification of PDGFRA and CDK6 loci, and a regional chromosome 5 loss. Nanostring analysis confirmed PDGFRA overexpression, and sequenom analyses were negative for IDH1/2 mutations.

Isolation of Bone Marrow-Derived Macrophages (BMDMs).

To generate macrophages from bone marrow, femurs and tibiae from Stat6$^{-/-}$, Il4ra$^{flox}$; LysM-cre, or WT BL6 mice were flushed and cells harvested under sterile conditions. The isolate was filtered through a 40 µm mesh filter and cultured in 30 ml Teflon bags (PermaLife PL-30) for 5-7 days in DMEM+10% FBS+10 ng/ml recombinant mouse CSF-1 (R&D Systems). Media were changed every other day.

TGL Infections.

Cell lines were labeled with a triple-imaging vector (TK-GFP-Luc; TGL) (61) for use in orthotopic in vivo experiments. The TGL vector was developed to enable non-invasive in vivo imaging of tumor growth over time. A standard protocol for retroviral infection was used. Briefly, GP2-293T cells were transfected with the TGL construct and pCL-Ampho at a 1:1 ratio, using Fugene (Promega) and OptiMEM (Gibco). 12 h later, media was replaced with complete antibiotic-free DMEM, and collected for 3 consecutive days for infection of target cells.

Orthotopic Transplantation Experiments.

TGL-labeled cells were resuspended in antibiotic-free serum-free DMEM for all orthotopic injections. Mice were fully anesthetized with ketamine/xylazine prior to surgery. Pain management included a 50l subcutaneous injection of bupivacaine (0.25%) at the surgical site prior to surgery, and an intraperitoneal injection of buprenorphine immediately following surgery. Mice were intracranially injected with glioma cells between 5-6 weeks of age using a fixed stereotactic apparatus (Stoelting). The number of cells injected was as follows: mouse glioma lines 2.5-5×10$^4$ cells/2 µl, human U251 cells 2.5×10$^5$ cells/2 µl, and patient-derived TS573 cells 5×10$^4$ cells/2 Injections were made to the right frontal cortex, approximately 1.5 mm lateral and 1 mm caudal from bregma, and at a depth of 2 mm. Hydrogen peroxide was used to clean the hole made by the surgical drill, and bone wax was used to close the hole. The incision was sealed using Vetbond tissue adhesive (3M). One week following injections, mice were randomly assigned to Vehicle or BLZ945 treatment groups, and dosed 1× daily by oral gavage. Bioluminescence imaging (BLI; Xenogen IVIS-200 Optical In Vivo Imaging System) was performed every 3-5 days over the course of the experiment to monitor tumor progression and response to therapy. Once BLZ945-treated tumors reached 3× the volume of their lowest BLI measurement, tumors were considered 'resistant', and mice were randomly assigned to combination treatment with BLZ945+OSI906, or BLZ945+vehicle. For doxycycline (dox)-inducible IGF1R shRNA experiments with U251 cells, mice were additionally assigned to either +/− dox groups (doxycycline hyclate diet formulated at 2,500 mg/kg, Envigo).

Animal Euthanasia and Tissue Harvest.

Mice were euthanized at the defined 26 week endpoint, or when symptomatic (poor grooming, lethargy, weight loss, hunching, macrocephaly/hydrocephalus, seizures). 26 weeks was selected because mice in the Ink4a/Arf$^{-/-}$ background develop spontaneous lymphomas and sarcomas beginning at ~30 weeks of age (62). Euthanasia was performed by either carbon dioxide asphyxiation or anesthesia (avertin; 2,2,2-tribromoethanol; Sigma) followed by cervical dislocation. For snap freezing of whole tumor samples, mice were euthanized 1 h following the last treatment dose, and tissues were collected, frozen immediately in liquid nitrogen, and stored at −80° C. for subsequent applications (e.g. RNA isolation, protein extraction). For isolation of whole tissues for histology, mice were fully anesthetized with avertin, transcardially perfused with 10 ml of PBS, followed by 10 ml of paraformaldehyde (PFA; 4% in PBS). Tissues were incubated in PFA overnight at 4° C., rinsed in PBS, and then transferred to sucrose (30%) for 2-3 days at 4° C. For hypoxia analysis, mice were injected intraperitoneally with 60 mg/kg of pimonidazole (hypoxyprobe-1; HPI) ~20 min prior to sacrifice and tissue collection. All tissues were embedded and frozen in Optimal Cutting Temperature (OCT) compound (Tissue-Tek®), and 10 μm cryostat tissue sections were used for all subsequent staining and analyses.

Immunofluorescence (IF).

For IF staining, 10 μm frozen sections were thawed and dried at room temperature, and rinsed in PBS. Tissue sections were blocked in 0.5% Blocking Reagent (PerkinElmer; 1 h at room temperature or overnight at 4° C.), followed by incubation in primary antibody (2 h at room temperature or overnight at 4° C.). Sections were then washed in PBS and incubated with the appropriate fluorophore-conjugated secondary antibody (Molecular Probes) at a dilution of 1:500 in 0.5% PNB (1 h at room temperature). DAPI was used as a counterstain prior to mounting with fluorescent mounting media (Dako).

Immunohistochemistry (IHC) and Von Kossa Staining.

For manual IHC, tissue sections were first subjected to citrate buffer based antigen retrieval by submerging in antigen unmasking solution (0.94% v/v in distilled water; Vector Laboratories) and microwaving for 10 min, followed by cooling to room temperature for 30 min. Endogenous peroxidases were blocked for 10 min with Dual Endogenous Enzyme Block (Dako). Slides were incubated with serum-free protein block (Dako) for 1 h at room temperature, and then incubated with primary antibody in a humidity chamber overnight at 4° C. The following day, slides were washed and incubated with HRP-conjugated secondary antibodies (Jackson Immunoresearch) for 1 h at room temperature, and positive staining was detected using diaminobenzidine (DAB) substrate-chromogen. Haematoxylin was used as a counterstain and slides were mounted with VECTASHIELD® mounting media (Vector). As an alternative to manual staining, a Ventana autostainer was used for staining of mouse GFAP, human phospho (p)-AKT, and human MRC1, which included automated deparaffinization, citrate buffer-based antigen retrieval, non-specific protein and endogenous peroxidase block, antibody incubation, and DAB detection. For visualization of calcium deposition in tissue sections, a Von Kossa staining kit was used as per manufacturer's instructions (Abcam). Briefly, tissues are treated with a silver nitrate solution, which is deposited by replacing calcium reduced by UV light. Nuclear fast red was used as a counterstain (Vector).

Histology and Grading.

For analysis of tissue histology and grading of tumor malignancy, haematoxylin and eosin (H&E) staining was performed using a Tissue-Tek® automated slide stainer, and slides were mounted with VECTASHIELD® mounting media (Vector). Tissues were blindly graded by a neuropathologist, according to standard WHO criteria (63). For CNS tumors, this grading system is based on a malignancy scale, where tumors that are minimally proliferative and infiltrative are considered grade I, while the most histologically aggressive, infiltrative, and incurable tumors (glioblastomas) are grade IV (63). GFAP quantification was performed by the Allred scoring method, which is the sum of a proportion score (0-5) and an intensity score (0-3) for a given marker (64).

Image Analysis.

Stained tissue sections were visualized under a Carl Zeiss Axioimager Z1 microscope equipped with an ApoTome.2, or a Carl Zeiss Axioimager M1 epifluorescence and brightfield microscope. Staining analyses were performed using a TissueGnostics slide scanning platform, and TissueQuest analysis software. This automated analysis platform was used to quantify number of positive counts, area of positive staining, and/or microvascular density within stained tissue sections in an unbiased manner (8).

Patient GBM Tissue Samples.

Patient GBM tissue samples used for staining and analysis (FIG. 5I and FIG. 17B) were obtained from the Brain Tumor Center, MSKCC. 18 patient tissue samples were used in total. IHC staining for MRC1 and p-AKT was performed as described above (see "Immunohistochemistry and Von Kossa staining" section), and quantitation was performed using the Axioimager Z1 scanning microscope (see "Image analysis" section). Correlational analysis across patients was performed using GraphPad Prism 6.0 (see "Data presentation and statistical analysis" section).

Protein Isolation and Immunoblotting.

To evaluate phospho-protein status of IGF-1R and AKT in culture, cells were seeded at 70-80% confluence, serum-starved for ~12 h, and then treated with OSI906 for 30 min. To evaluate phosphorylation of IGF-1R or AKT in snap-frozen tumor samples, tissues were dissociated with a glass homogenizer on ice in the presence of lysis buffer. All protein lysates were prepared in RIPA lysis buffer supplemented with Halt™ protease inhibitor (1:100; Thermo Scientific) and Halt™ phosphatase inhibitor (1:100; Thermo Scientific), and protein was quantified using a BCA protein assay kit (Pierce). Equal amounts of protein (20 μg/lane for cell lines, and 100 μg/lane for tissue samples) were loaded onto SDS-PAGE precast gels (Invitrogen) and transferred to PVDF membranes for immunoblotting. Membranes were blocked in 5% milk, incubated with primary antibodies (Table S4) for 1 h at room temperature or overnight at 4° C., washed with 0.1% TBS-T, and incubated with HRP-conjugated secondary antibodies (Jackson Immunoresearch) for 1 h at room temperature. SuperSignal West Femto or Pico chemiluminescent substrate and CL-XPosure Film (Pierce) were used for signal detection.

RNA Isolation, Reverse Transcription, and Quantitative Real-Time PCR.

RNA was isolated with Trizol, DNase treated, and 1 μg of RNA was used for cDNA synthesis using a High Capacity cDNA Reverse Transcription kit (Applied Biosystems). Mouse taqman probes (Applied Biosystems) were used for quantifying expression of Igf1 (Mm00439560_m1), Chil3 (Mm00657889_mH), Ccl17 (Mm01244826_g1), Retnla (Mm00445109_m1), Il4 (Mm00445260_m1), Arg1 (Mm00475988_m1), Cd36 (Mm00432403_m1), Mrc1 (Mm01329362_m1), Ubc (Mm02525934_g1; housekeeping), and Hprt (Mm01545339_m1; housekeeping). Human taqman probes (Applied Biosystems) were used for quantifying expression of IL4 (Hs00174122_m1), IL13

(Hs00174379_m1), IGF1 (Hs01547656_m1) and HPRT1 (Hs02800695_m1; housekeeping).

MTT Assays.

Cell growth rate was determined using an MTT cell proliferation kit (Roche). Briefly, cells were plated in triplicate in 96-well plates. $1\times10^3$ cells/well were plated for mouse glioma cell lines, and $5\times10^3$ cells/well were plated for BMDMs. For BLZ945 time course experiments, cells were grown in the presence of 6,700 nM of BLZ945 versus an equal percent DMSO, media was changed every 48 h, and viability measurements were taken every 24 h. For dose response experiments, cells were grown in the presence of an IGF-1R inhibitor (AEW541, ADW742, BMS754807, or OSI906) versus an equal percent DMSO at the doses indicated (see "Biologicals and pharmaceuticals" section above), and viability measurements were taken after 24 h. Reduction of the MTT substrate was detected by colorimetric analysis using a plate reader as per the manufacturer's protocol. 10 μl of MTT labeling reagent was added to each well and then incubated for 4 h at 37° C., followed by the addition of 100 μl MTT solubilization reagent overnight. The mixture was gently resuspended and absorbance was measured at 595 nm and 750 nm on a spectraMax 340pc plate reader (Molecular Devices).

Ex Vivo GMEC Assays.

Figure 16I:
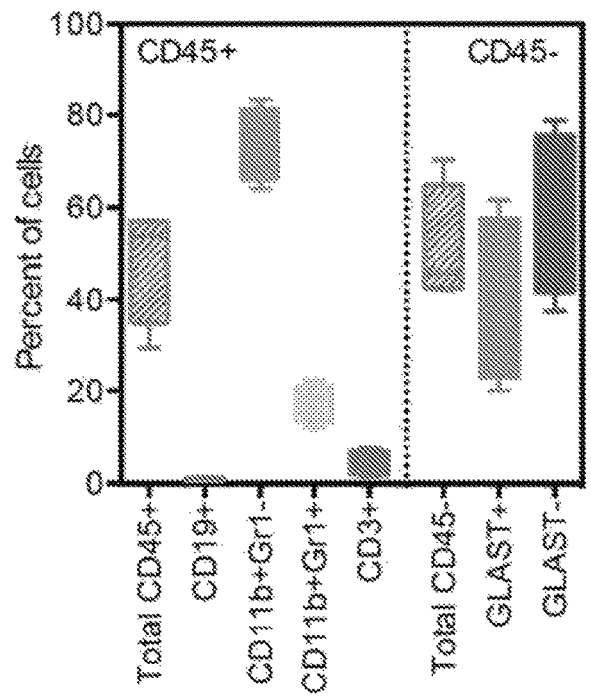
Figure 16J:
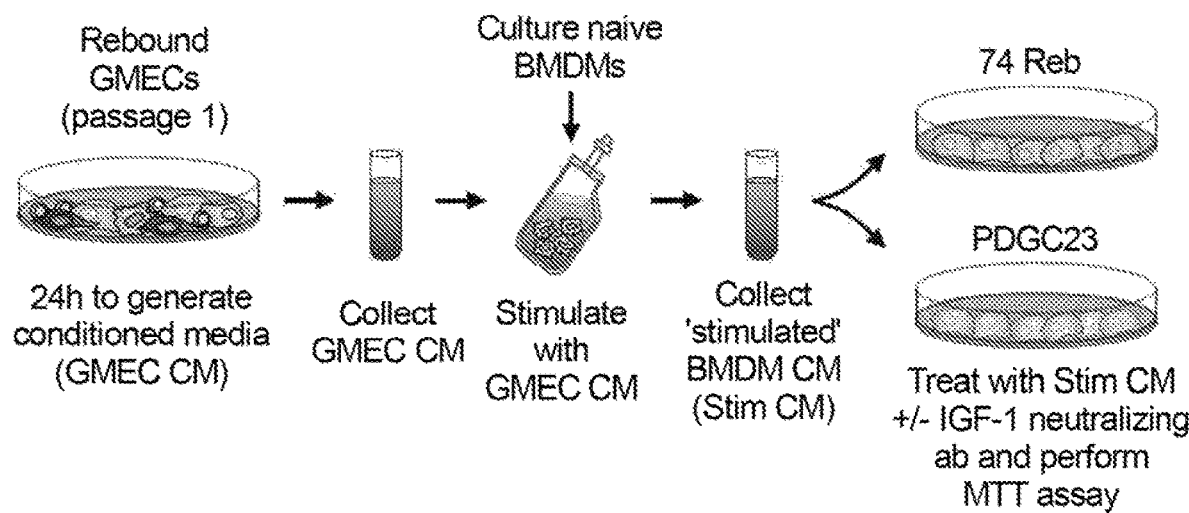

Glioma microenvironment cultures (GMECs) are early-passage heterotypic cell cultures harvested directly from PDG mouse primary tumors. Flow cytometry characterization of these cultures revealed that passage 1 GMECs contain a high abundance of tumor cells, astrocytes, and macrophages, as well as smaller proportions of myeloid progenitors, T cells and B cells (FIG. 16I). In ex vivo assays, conditioned media (CM) was derived from passage 1 rebound GMECs, and this CM was used to treat naïve BMDMs in vitro (see FIG. 16J for experimental design). CM was collected from these GMEC-stimulated BMDMs (Stim CM), and applied to either rebound glioma cell lines (highly sensitive to IGF-1R inhibition) or naïve glioma cell lines (less-sensitive to IGF-1R inhibition), +/− a neutralizing antibody for IGF-1. An MTT assay was used to assess changes in growth in response to each treatment condition, as described above.

Flow Cytometry and Fluorescence-Activated Cell Sorting (FACS) on Primary Mouse Tissues.

Mice were fully anesthetized with avertin and transcardially perfused with 20 ml of PBS. The brain was then isolated and the tumor was macrodissected from the surrounding normal tissue. Tissues were mechanically dissociated and filtered into a single cell suspension. For flow cytometry, cells were counted and incubated with Fc block for 1 h (BD Biosciences; $1:100/10^6$ cells), followed by a 30 min incubation with LIVE/DEAD® fixable dead cell kit (Invitrogen), and then a 1 h incubation with conjugated antibodies for extracellular markers. For FACS, cells were counted and incubated with Fc block for 1 h, followed by a 1 h incubation with conjugated antibodies, and then stained with DAPI for dead cell exclusion. OneComp eBeads (eBioscience), ArC™ Amine Reactive Compensation Beads (Invitrogen), and/or cell suspensions from spleen were used for compensation controls. A BD LSRFortessa™ was used for flow cytometry, and a BD FACSAria III™ was used for cell sorting.

Distinguishing Between Putative BMDMs and Microglia by Flow Cytometry.

Flow cytometry was used to evaluate the proportions of peripherally derived BMDMs versus resident microglia in PDG tumors across different treatment groups, according to published methods (22-24). Briefly, after gating on live cells, we used cell surface expression of CD45 and CD11b to distinguish between the two populations, where $CD45^{lo}$ CD11b+ defined putative microglia, while $CD45^{hi}$ CD11b+ defined putative BMDMs. In using this method, we acknowledge its limitations, and recognize that these two populations cannot be definitively distinguished without lineage tracing experiments that specifically label yolk sac-derived microglia or peripherally recruited BMDMs.

FACS Purification of Human Peripheral Immune Cell Types.

Human buffy coats from three consenting healthy donors were obtained from the New York Blood Center. For isolation of neutrophils and eosinophils, buffy coats were directly RBC lysed (BD PharmLyse) for 15 minutes at room temperature. All other cell types were isolated from the top layer of a Ficoll gradient separation (HistoPaque, Sigma). Cells were pelleted for 10 minutes at 300×G and washed twice with FACS buffer (PBS+2% fetal bovine serum) and Fc blocked (Biolegend TruStain FcX). Cells were incubated with the appropriate antibodies for 15 minutes (Table S4). Cells were FACS purified on an Aria III (BD). For human macrophage differentiation, PBMCs were isolated from buffy coats following a Ficoll gradient. Monocytes were further purified from the interphase of a 70%/30% Percoll gradient. Monocytes were then washed twice with PBS, and cultured in Teflon bags (Origin) for 7 days in DMEM+2% human serum+recombinant human CSF-1 (10 ng/ml; R&D Systems). CSF-1 and media were replaced every 48 h.

Array Comparative Genomic Hybridization (aCGH).

All sequencing and quality control was performed at the Integrated Genomics Operation, MSKCC. DNA was isolated from passage 1 PDG neurospheres from rebound tumors or corresponding liver tissue using TRIzol as per manufacturer instructions (Invitrogen). 3 ug of DNA was used with an Agilent standard cy5/cy3 labeling protocol. Briefly, Agilent Mouse CGH 180 k arrays were hybridized at 65° C. and 20 rpm for 40 h. Slides were then scanned using the Agilent scanner according to the manufacturer's instructions. The raw data were extracted with Feature Extraction using Agilent default analysis settings. Subsequent analyses were performed in R v3.1.0 using the "DNAcopy" package (65).

RNA-Sequencing.

Three RNA-seq experiments were performed in total: (i) FACS-purified tumor cells (CD45-PDGFRα+) and TAMs (CD45+CD11b+Gr1−) from Veh, EP and Reb tumors, (ii) FACS-purified astrocytes (CD45-GLAST+), B cells (CD45+CD19+), Tc cells (CD45+CD3+CD8+) and bulk T cells (CD45+CD3+CD8−) from Reb tumors, (iii) FACS-purified TAMs (CD45+CD11b+Gr1−) from 28d and Reb tumors. RNA-sequencing and quality control was performed at the Integrated Genomics Operation, MSKCC, or GENEWIZ, N.J. In all cases, RNA was isolated using TRIzol as per manufacturer instructions (Invitrogen), and RNA integrity was assessed by an Agilent Bioanalyzer 2100. RNA-sequencing libraries were prepared using the SMART-Seq library preparation kit and 2×50 or 2×100 base pair sequencing was performed on an Illumina HISeq 2000. Sequencing quality was assessed with FASTQC (http://www.bioinformatics.babraham.ac.uk/projects/fastqc/).

Reads were mapped to the mouse genome (mm10) using STAR 2.3.0e (66) with the default parameters, a minimum intron length of 70 base pairs and a maximum of 100,000 base pairs. BAM files were generated and sorted, duplicate reads were then removed using SAMTOOLS (67). Read counts were tabulated with HT-Seq using "union" mode and the iGenomes GFF file as a reference (Illumina) (68).

Gene Expression Analyses.

Raw count data from HT-Seq was imported into R (v3.1.0) and normalized using limma voom (69). Principal component analysis was completed using the princomp function on mean centered data. A log 2 fold change cutoff of 1 and a false discovery rate of 10% were applied for all differential gene expression analyses (Table S1). Significantly upregulated genes from these lists were used in gene ontology analyses using DAVID (70). Gene set variation analysis (GSVA) was performed on RNA-seq data from FACS-purified PDGFRα+ tumor cells, using the GSVA package (14) with gene sets from the C2 group from MSigDB (71). A log 2 fold change cutoff of 1 and a false discovery rate cutoff of 10% were used to determine differentially enriched gene sets (FIG. 11B). The spectrum model of macrophage activation was assessed with gene set enrichment analysis (GSEA), using the gsea function from the phenoTest package in R (http://rpackages.ianhowson.com/bioc/phenoTest/). A minimum P-value of $<1 \times 10^{16}$ was used to represent significance values that were reported as 0.0 and outside of the determined distribution. Gene sets were adapted from a previous study where murine macrophages were stimulated with IFN-gamma, IL-4, TNF-alpha, TGF-beta, IL-1beta, MALP2 or CPG (27). A literature-derived IL-4 responsive gene set was generated through the use of QIAGEN's Ingenuity iReport (www.qiagen.com/ingenuity).

Transcription Factor Activity Analysis.

Transcription factor (TF) activity analysis was performed as an adaptation of previously published methods: ISMARA (72) and Regulatorinference (73). Briefly, transcription start sites and Motevo predictions (74) of binding sites were downloaded from the Swiss Regulon (http://swissregulon.unibas.ch/fcgi/sr/downloads#). These were used to determine the number of predicted binding sites for 185 transcription factor families across all mouse promoters. Promoters were designated as 2 kilobases upstream and downstream of transcription start sites. This tabulated matrix was then used in a ridge regression to model log 2 gene expression values generated by voom. Ridge regression was performed with the glmnet function in R (75). The regularization parameter, lambda, was identified for each sample through 10-fold cross validation. The coefficients for each TF family were z-scored and used as relative TF activity scores in subsequent analyses. Differentially enriched TFs were identified by using the z-scored values in limma with a log 2 fold change cutoff of 1 and a false discovery rate of 10% (Table S3).

External Data Set Analysis.

RNA-seq expression data from the TCGA glioblastoma patient data set was downloaded using TCGA-assembler (76). For survival analyses, these data were filtered for patients with updated clinical information from the Broad Firehose. Correlations between IGF1 and macrophage markers (CD163, MRC1, CSF1R, CD68, AIF1) or astrocyte markers (GFAP and ALDH1L1) were assessed using a Spearman correlation coefficient. Normalized gene expression data for human bulk tumor versus tumor-associated macrophage fraction was downloaded from the GEO under accession number GSE16119 (44). Subtype calls for patients were obtained from GlioVis (http://gliovis.bioinfo.cnio.es). PI3K signature scores were tabulated with a single sample gene set enrichment, as used for macrophage activity analysis. The gene set was from the Hallmark collection from MsigDB, systematic name M5923 (43).

Data Availability.

All RNA-seq data has been deposited to the GEO under the accession number GSE69104, and aCGH data under GSE80399. All code used in this project can be found at https://bitbucket.org/bowmanr/joycelab-brain-tme.

Data Presentation and Statistical Analysis.

GraphPad Prism 6.0 or R Studio was used for all data analysis. Parametric data are presented as mean±standard error (s.e.m.) and were analyzed by an unpaired two-tailed Student's t-test. For multiple comparisons, a one-way ANOVA with Tukey's or Dennett's correction was used as noted in the figure legend. Non-parametric data were analyzed by a Mann-Whitney test on ranks. For survival curves, P-values were obtained using the Log Rank (Mantel-Cox) test. Fisher's exact test was used for histological tumor grading. A pairwise Spearman correlation test was used for correlational analyses. $P<0.05$ was considered as statistically significant in all cases. Principal component analyses, correlation plots, Volcano plots, heatmaps, and network plots were plotted in R Studio using base graphics (http://www.R-project.org/), rg1 (http://CRAN.R-project.org/package=rg1), gplots (http://CRAN.R-project.org/package=gplots), ggplot2 (77) and qgraph packages (78).

REFERENCES

1. D. F. Quail, J. A. Joyce, Microenvironmental regulation of tumor progression and metastasis. *Nat. Med.* 19, 1423-1437 (2013).
2. M. R. Junttila, F. J. de Sauvage, Influence of tumour microenvironment heterogeneity on therapeutic response. *Nature.* 501, 346-354 (2013).
3. R. Stupp, W. P. Mason, M. J. van den Bent, M. Weller, B. Fisher, M. J. Taphoorn, K. Belanger, A. A. Brandes, C. Marosi, U. Bogdahn, J. Curschmann, R. C. Janzer, S. K. Ludwin, T. Gorlia, A. Allgeier, D. Lacombe, J. G. Cairncross, E. Eisenhauer, R. O. Mirimanoff, R. European Organisation for, T. Treatment of Cancer Brain, G. Radiotherapy, G. National Cancer Institute of Canada Clinical Trials, Radiotherapy plus concomitant and adjuvant temozolomide for glioblastoma. *N. Engl. J. Med.* 352, 987-996 (2005).
4. Y. Komohara, K. Ohnishi, J. Kuratsu, M. Takeya, Possible involvement of the M2 anti-inflammatory macrophage phenotype in growth of human gliomas. *J. Pathol.* 216, 15-24 (2008).
5. L. Bingle, N. J. Brown, C. E. Lewis, The role of tumour-associated macrophages in tumour progression: implications for new anticancer therapies. *J. Pathol.* 196, 254-265 (2002).
6. S. F. Hussain, D. Yang, D. Suki, K. Aldape, E. Grimm, A. B. Heimberger, The role of human glioma-infiltrating microglia/macrophages in mediating antitumor immune responses. *Neoro. Oncol.* 8, 261-279 (2006).
7. B. Ruffell, L. M. Coussens, Macrophages and Therapeutic Resistance in Cancer. *Cancer Cell.* 27, 462-472 (2015).
8. S. M. Pyonteck, L. Akkari, A. J. Schuhmacher, R. L. Bowman, L. Sevenich, D. F. Quail, O. C. Olson, M. L. Quick, J. T. Huse, V. Teijeiro, M. Setty, C. S. Leslie, Y. Oei, A. Pedraza, J. Zhang, C. W. Brennan, J. C. Sutton, E. C. Holland, D. Daniel, J. A. Joyce, CSF-1R inhibition alters macrophage polarization and blocks glioma progression. *Nat. Med.* 19, 1264-1272 (2013).
9. S. J. Coniglio, E. Eugenin, K. Dobrenis, E. R. Stanley, B. L. West, M. H. Symons, J. E. Segall, Microglial stimulation of glioblastoma invasion involves epidermal growth factor receptor (EGFR) and colony stimulating factor 1 receptor (CSF-1R) signaling. *Mol. Med.* 18, 519-527 (2012).
10. S. Patel, M. R. Player, Colony-stimulating factor-1 receptor inhibitors for the treatment of cancer and inflammatory disease. *Curr. Top. Med. Chem.* 9, 599-610 (2009).
11. C. H. Ries, M. A. Cannarile, S. Hoves, J. Benz, K. Wartha, V. Runza, F. Rey-Giraud, L. P. Pradel, F. Feuerhake, I. Klaman, T. Jones, U. Jucknischke, S. Scheiblich, K. Kaluza, I. H. Gorr, A. Walz, K. Abiraj, P. A. Cassier, A. Sica, C. Gomez-Roca, K. E. de Visser, A. Italiano, C. Le Tourneau, J. P. Delord, H. Levitsky, J. Y. Blay, D. Ruttinger, Targeting tumor-associated macrophages with anti-CSF-1R antibody reveals a strategy for cancer therapy. *Cancer Cell.* 25, 846-859 (2014).
12. W. D. Tap, Z. A. Wainberg, S. P. Anthony, P. N. Ibrahim, C. Zhang, J. H. Healey, B. Chmielowski, A. P. Staddon, A. L. Cohn, G. I. Shapiro, V. L. Keedy, A. S. Singh, I. Puzanov, E. L. Kwak, A. J. Wagner, D. D. Von Hoff, G. J. Weiss, R. K. Ramanathan, J. Zhang, G. Habets, Y. Zhang, E. A. Burton, G. Visor, L. Sanftner, P. Severson, H. Nguyen, M. J. Kim, A. Marimuthu, G. Tsang, R. Shellooe, C. Gee, B. L. West, P. Hirth, K. Nolop, M. van de Rijn, H. H. Hsu, C. Peterfy, P. S. Lin, S. Tong-Starksen, G. Bollag, Structure-Guided Blockade of CSF1R Kinase in Tenosynovial Giant-Cell Tumor. *N. Engl. J. Med.* 373, 428-437 (2015).
13. D. Hambardzumyan, N. M. Amankulor, K. Y. Helmy, O. J. Becher, E. C. Holland, Modeling Adult Gliomas Using RCAS/t-va Technology. *Transl. Oncol.* 2, 89-95 (2009).
14. S. Hanzelmann, R. Castelo, J. Guinney, GSVA: gene set variation analysis for microarray and RNA-seq data. *BMC Bioinformatics.* 14, 7 (2013).
15. S. M. Brachmann, J. Kleylein-Sohn, S. Gaulis, A. Kauffmann, M. J. Blommers, M. Kazic-Legueux, L. Laborde, M. Hattenberger, F. Stauffer, J. Vaxelaire, V. Romanet, C. Henry, M. Murakami, D. A. Guthy, D. Sterker, S. Bergling, C. Wilson, T. Brummendorf, C. Fritsch, C. Garcia-Echeverria, W. R. Sellers, F. Hofmann, S. M. Maira, Characterization of the mechanism of action of the pan class I PI3K inhibitor NVP-BKM120 across a broad range of concentrations. *Mol. Cancer Ther.* 11, 1747-1757 (2012).
16. C. W. Brennan, R. G. Verhaak, A. McKenna, B. Campos, H. Noushmehr, S. R. Salama, S. Zheng, D. Chakravarty, J. Z. Sanborn, S. H. Berman, R. Beroukhim, B. Bernard, C. J. Wu, G. Genovese, I. Shmulevich, J. Barnholtz-Sloan, L. Zou, R. Vegesna, S. A. Shukla, G. Ciriello, W. K. Yung, W. Zhang, C. Sougnez, T. Mikkelsen, K. Aldape, D. D. Bigner, E. G. Van Meir, M. Prados, A. Sloan, K. L. Black, J. Eschbacher, G. Finocchiaro, W. Friedman, D. W. Andrews, A. Guha, M. Iacocca, B. P. O'Neill, G. Foltz, J. Myers, D. J. Weisenberger, R. Penny, R. Kucherlapati, C. M. Perou, D. N. Hayes, R. Gibbs, M. Marra, G. B. Mills, E. Lander, P. Spellman, R. Wilson, C. Sander, J. Weinstein, M. Meyerson, S. Gabriel, P. W. Laird, D. Haussler, G. Getz, L. Chin, T. R. Network, The somatic genomic landscape of glioblastoma. *Cell.* 155, 462-477 (2013).
17. P. Therasse, S. G. Arbuck, E. A. Eisenhauer, J. Wanders, R. S. Kaplan, L. Rubinstein, J. Verweij, M. Van Glabbeke, A. T. van Oosterom, M. C. Christian, S. G. Gwyther, New guidelines to evaluate the response to treatment in solid tumors. European Organization for Research and Treatment of Cancer, National Cancer Institute of the United States, National Cancer Institute of Canada. *J. Natl. Cancer Inst.* 92, 205-216 (2000).
18. J. E. Burda, M. V. Sofroniew, Reactive gliosis and the multicellular response to CNS damage and disease. *Neuron.* 81, 229-248 (2014).
19. E. N. Arwert, E. Hoste, F. M. Watt, Epithelial stem cells, wound healing and cancer. *Nat. Rev. Cancer.* 12, 170-180 (2012).
20. F. Ginhoux, J. L. Schultze, P. J. Murray, J. Ochando, S. K. Biswas, New insights into the multidimensional concept of macrophage ontogeny, activation and function. *Nat. Immunol.* 17, 34-40 (2015).
21. R. L. Bowman, J. A. Joyce, Therapeutic targeting of tumor-associated macrophages and microglia in glioblastoma. *Immunotherapy.* 6, 663-666 (2014).
22. G. Locatelli, S. Wortge, T. Buch, B. Ingold, F. Frommer, B. Sobottka, M. Kruger, K. Karram, C. Buhlmann, I. Bechmann, F. L. Heppner, A. Waisman, B. Becher, Primary oligodendrocyte death does not elicit anti-CNS immunity. *Nat. Neurosci.* 15, 543-550 (2012).
23. K. Gabrusiewicz, A. Ellert-Miklaszewska, M. Lipko, M. Sielska, M. Frankowska, B. Kaminska, Characteristics of the alternative phenotype of microglia/macrophages and its modulation in experimental gliomas. *PloS One.* 6, e23902 (2011).
24. J. D. Sedgwick, S. Schwender, H. Imrich, R. Dorries, G. W. Butcher, V. ter Meulen, Isolation and direct characterization of resident microglial cells from the normal and inflamed central nervous system. *Proc. Natl. Acad. Sci. U.S.A* 88, 7438-7442 (1991).
25. F. Kratochvill, G. Neale, J. M. Haverkamp, L. A. Van de Velde, A. M. Smith, D. Kawauchi, J. McEvoy, M. F. Roussel, M. A. Dyer, J. E. Qualls, P. J. Murray, TNF Counterbalances the Emergence of M2 Tumor Macrophages. *Cell Reports.* 12, 1902-1914 (2015).
26. S. K. Biswas, A. Mantovani, Macrophage plasticity and interaction with lymphocyte subsets: cancer as a paradigm. *Nat. Immunol.* 11, 889-896 (2010).
27. R. Ostuni, V. Piccolo, I. Barozzi, S. Polletti, A. Termanini, S. Bonifacio, A. Curina, E. Prosperini, S. Ghisletti, G. Natoli, Latent enhancers activated by stimulation in differentiated cells. *Cell.* 152, 157-171 (2013).
28. D. M. Mosser, J. P. Edwards, Exploring the full spectrum of macrophage activation. *Nat. Rev. Immunol.* 8, 958-969 (2008).
29. A. Mantovani, S. K. Biswas, M. R. Galdiero, A. Sica, M. Locati, Macrophage plasticity and polarization in tissue repair and remodelling. *J. Pathol.* 229, 176-185 (2013).
30. B. J. Faler, R. A. Macsata, D. Plummer, L. Mishra, A. N. Sidawy, Transforming growth factor-beta and wound healing. *Perspect. Vasc. Surg. Endovasc. Ther.* 18, 55-62 (2006).
31. J. Silver, J. H. Miller, Regeneration beyond the glial scar. *Nat. Rev. Neurosci.* 5, 146-156 (2004).
32. F. E. Lund, B. A. Garvy, T. D. Randall, D. P. Harris, Regulatory roles for cytokine-producing B cells in infection and autoimmune disease. *Curr. Dir. Autoimmun.* 8, 25-54 (2005).
33. D. P. Harris, L. Haynes, P. C. Sayles, D. K. Duso, S. M. Eaton, N. M. Lepak, L. L. Johnson, S. L. Swain, F. E. Lund, Reciprocal regulation of polarized cytokine production by effector B and T cells. *Nat. Immunol.* 1, 475-482 (2000).
34. B. Johansson-Lindbom, C. A. Borrebaeck, Germinal center B cells constitute a predominant physiological source of IL-4: implication for Th2 development in vivo. *J. Immunol.* 168, 3165-3172 (2002).
35. O. Butovsky, A. E. Talpalar, K. Ben-Yaakov, M. Schwartz, Activation of microglia by aggregated betaamyloid or lipopolysaccharide impairs MHC-II expression and renders them cytotoxic whereas IFN-gamma and IL-4 render them protective. *Mol. Cell. Neurosci.* 29, 381-393 (2005).

36. S. J. Forbes, N. Rosenthal, Preparing the ground for tissue regeneration: from mechanism to therapy. *Nat. Med.* 20, 857-869 (2014).

37. M. W. Wynes, D. W. Riches, Induction of macrophage insulin-like growth factor-I expression by the Th2 cytokines IL-4 and IL-13. *J. Immunol.* 171, 3550-3559 (2003).

38. B. K. Kaspar, J. Llado, N. Sherkat, J. D. Rothstein, F. H. Gage, Retrograde viral delivery of IGF-1 prolongs survival in a mouse ALS model. *Science.* 301, 839-842 (2003).

39. W. H. Zheng, S. Kar, S. Dore, R. Quirion, Insulin-like growth factor-1 (IGF-1): a neuroprotective trophic factor acting via the Akt kinase pathway. *J. Neural Transm. Suppl.* 261-272 (2000).

40. S. Dupraz, D. Grassi, D. Karnas, A. F. Nieto Guil, D. Hicks, S. Quiroga, The insulin-like growth factor 1 receptor is essential for axonal regeneration in adult central nervous system neurons. *PloS One.* 8, e54462 (2013).

41. A. M. Fernandez, I. Torres-Aleman, The many faces of insulin-like peptide signalling in the brain. *Nat. Rev. Neurosci.* 13, 225-239 (2012).

42. M. Pollak, Insulin and insulin-like growth factor signalling in neoplasia. *Nat. Rev. Cancer.* 8, 915-928 (2008).

43. A. Liberzon, C. Birger, H. Thorvaldsdottir, M. Ghandi, J. P. Mesirov, P. Tamayo, The Molecular Signatures Database (MSigDB) hallmark gene set collection. *Cell Syst.* 1, 417-425 (2015).

44. A. Murat, E. Migliavacca, S. F. Hussain, A. B. Heimberger, I. Desbaillets, M. F. Hamou, C. Ruegg, R. Stupp, M. Delorenzi, M. E. Hegi, Modulation of angiogenic and inflammatory response in glioblastoma by hypoxia. *PloS One.* 4, e5947 (2009).

45. N. Hermann-Kleiter, G. Baier, NFAT pulls the strings during CD4+T helper cell effector functions. *Blood.* 115, 2989-2997 (2010).

46. N. Butowski, H. Colman, J. F. De Groot, A. M. Omuro, L. Nayak, P. Y. Wen, T. F. Cloughesy, A. Marimuthu, S. Haidar, A. Perry, J. Huse, J. Phillips, B. L. West, K. B. Nolop, H. H. Hsu, K. L. Ligon, A. M. Molinaro, M. Prados, Orally administered colony stimulating factor 1 receptor inhibitor PLX3397 in recurrent glioblastoma: an Ivy Foundation Early Phase Clinical Trials Consortium phase II study. *Neuro. Oncol.* (2015).

47. C. Holohan, S. Van Schaeybroeck, D. B. Longley, P. G. Johnston, Cancer drug resistance: an evolving paradigm. *Nat. Rev. Cancer.* 13, 714-726 (2013).

48. M. J. Mulvihill, A. Cooke, M. Rosenfeld-Franklin, E. Buck, K. Foreman, D. Landfair, M. O'Connor, C. Pirritt, Y. Sun, Y. Yao, L. D. Arnold, N. W. Gibson, Q. S. Ji, Discovery of OSI-906: a selective and orally efficacious dual inhibitor of the IGF-1 receptor and insulin receptor. *Future Med. Chem.* 1, 1153-1171 (2009).

49. M. H. Roehrl, S. Kang, J. Aramburu, G. Wagner, A. Rao, P. G. Hogan, Selective inhibition of calcineurin-NFAT signaling by blocking protein-protein interaction with small organic molecules. *Proc. Natl. Acad. Sci. U.S.A* 101, 7554-7559 (2004).

50. K. Loser, S. Balkow, T. Higuchi, J. Apelt, A. Kuhn, T. A. Luger, S. Beissert, FK506 controls CD40L-induced systemic autoimmunity in mice. *J. Invest. Dermatol.* 126, 1307-1315 (2006).

51. Y. Chiba, M. Todoroki, Y. Nishida, M. Tanabe, M. Misawa, A novel STATE inhibitor AS1517499 ameliorates antigen-induced bronchial hypercontractility in mice. *Am. J. Respir. Cell. Mol. Biol.* 41, 516-524 (2009).

52. C. Dai, J. C. Celestino, Y. Okada, D. N. Louis, G. N. Fuller, E. C. Holland, PDGF autocrine stimulation dedifferentiates cultured astrocytes and induces oligodendrogliomas and oligoastrocytomas from neural progenitors and astrocytes in vivo. *Genes Dev.* 15, 1913-1925 (2001).

53. E. Tchougounova, M. Kastemar, D. Brasater, E. C. Holland, B. Westermark, L. Uhrbom, Loss of Arf causes tumor progression of PDGFB-induced oligodendroglioma. *Oncogene.* 26, 6289-6296 (2007).

54. T. Ozawa, M. Riester, Y. K. Cheng, J. T. Huse, M. Squatrito, K. Helmy, N. Charles, F. Michor, E. C. Holland, Most human non-GCIMP glioblastoma subtypes evolve from a common proneural-like precursor glioma. *Cancer Cell.* 26, 288-300 (2014).

55. M. Squatrito, C. W. Brennan, K. Helmy, J. T. Huse, J. H. Petrini, E. C. Holland, Loss of ATM/Chk2/p53 pathway components accelerates tumor development and contributes to radiation resistance in gliomas. *Cancer Cell.* 18, 619-629 (2010).

56. X. Hu, P. P. Pandolfi, Y. Li, J. A. Koutcher, M. Rosenblum, E. C. Holland, mTOR promotes survival and astrocytic characteristics induced by Pten/AKT signaling in glioblastoma. *Neoplasia.* 7, 356-368 (2005).

57. J. T. Huse, C. Brennan, D. Hambardzumyan, B. Wee, J. Pena, S. H. Rouhanifard, C. Sohn-Lee, C. le Sage, R. Agami, T. Tuschl, E. C. Holland, The PTEN-regulating microRNA miR-26a is amplified in high-grade glioma and facilitates gliomagenesis in vivo. *Genes Dev.* 23, 1327-1337 (2009).

58. A. H. Shih, C. Dai, X. Hu, M. K. Rosenblum, J. A. Koutcher, E. C. Holland, Dose-dependent effects of platelet-derived growth factor-B on glial tumorigenesis. *Cancer Res.* 64, 4783-4789 (2004).

59. J. B. Jensen, M. Parmar, Strengths and limitations of the neurosphere culture system. *Mol. Neurobiol.* 34, 153-161 (2006).

60. N. J. Szerlip, A. Pedraza, D. Chakravarty, M. Azim, J. McGuire, Y. Fang, T. Ozawa, E. C. Holland, J. T. Huse, S. Jhanwar, M. A. Leversha, T. Mikkelsen, C. W. Brennan, Intratumoral heterogeneity of receptor tyrosine kinases EGFR and PDGFRA amplification in glioblastoma defines subpopulations with distinct growth factor response. *Proc. Natl. Acad. Sci. U.S.A* 109, 3041-3046 (2012).

61. V. Ponomarev, M. Doubrovin, I. Serganova, J. Vider, A. Shavrin, T. Beresten, A. Ivanova, L. Ageyeva, V. Tourkova, J. Balatoni, W. Bornmann, R. Blasberg, J. Gelovani Tjuvajev, A novel triple-modality reporter gene for whole-body fluorescent, bioluminescent, and nuclear noninvasive imaging. *Eur. J. Nucl. Med. Mol. Imaging.* 31, 740-751 (2004).

62. M. Serrano, H. Lee, L. Chin, C. Cordon-Cardo, D. Beach, R. A. DePinho, Role of the INK4a locus in tumor suppression and cell mortality. *Cell.* 85, 27-37 (1996).

63. D. N. Louis, H. Ohgaki, O. D. Wiestler, W. K. Cavenee, P. C. Burger, A. Jouvet, B. W. Scheithauer, P. Kleihues, The 2007 WHO classification of tumours of the central nervous system. *Acta Neuropathol.* 114, 97-109 (2007).

64. D. C. Allred, J. M. Harvey, M. Berardo, G. M. Clark, Prognostic and predictive factors in breast cancer by immunohistochemical analysis. *Mod. Pathol.* 11, 155-168 (1998).

65. V. E. Seshan, A. Olshen, DNAcopy: DNA copy number data analysis. *R package version* 1.44.0.

66. A. Dobin, C. A. Davis, F. Schlesinger, J. Drenkow, C. Zaleski, S. Jha, P. Batut, M. Chaisson, T. R. Gingeras, STAR: ultrafast universal RNA-seq aligner. *Bioinformatics.* 29, 15-21 (2013).
67. H. Li, B. Handsaker, A. Wysoker, T. Fennell, J. Ruan, N. Homer, G. Marth, G. Abecasis, R. Durbin, S. Genome Project Data Processing, The Sequence Alignment/Map format and SAMtools. *Bioinformatics.* 25, 2078-2079 (2009).
68. S. Anders, P. T. Pyl, W. Huber, HTSeq—a Python framework to work with high-throughput sequencing data. *Bioinformatics.* 31, 166-169 (2015).
69. C. W. Law, Y. Chen, W. Shi, G. K. Smyth, voom: Precision weights unlock linear model analysis tools for RNA-seq read counts. *Genome Biol.* 15, R29 (2014).
70. G. Dennis, Jr., B. T. Sherman, D. A. Hosack, J. Yang, W. Gao, H. C. Lane, R. A. Lempicki, DAVID: Database for Annotation, Visualization, and Integrated Discovery. *Genome Biol.* 4, P3 (2003).
71. A. Subramanian, P. Tamayo, V. K. Mootha, S. Mukherjee, B. L. Ebert, M. A. Gillette, A. Paulovich, S. L. Pomeroy, T. R. Golub, E. S. Lander, J. P. Mesirov, Gene set enrichment analysis: a knowledge-based approach for interpreting genome-wide expression profiles. *Proc. Natl. Acad. Sci. U.S.A* 102, 15545-15550 (2005).
72. P. J. Balwierz, M. Pachkov, P. Arnold, A. J. Gruber, M. Zavolan, E. van Nimwegen, ISMARA: automated modeling of genomic signals as a democracy of regulatory motifs. *Genome Res.* 24, 869-884 (2014).
73. M. Setty, K. Helmy, A. A. Khan, J. Silber, A. Arvey, F. Neezen, P. Agius, J. T. Huse, E. C. Holland, C. S. Leslie, Inferring transcriptional and microRNA-mediated regulatory programs in glioblastoma. *Mol. Syst. Biol.* 8, 605 (2012).
74. M. Pachkov, I. Erb, N. Molina, E. van Nimwegen, SwissRegulon: a database of genome-wide annotations of regulatory sites. *Nucleic Acids Res.* 35, D127-131 (2007).
75. J. Friedman, T. Hastie, R. Tibshirani, Regularization Paths for Generalized Linear Models via Coordinate Descent. *J. Stat. Softw.* 33, 1-22 (2010).
76. Y. Zhu, P. Qiu, Y. Ji, TCGA-assembler: open-source software for retrieving and processing TCGA data. *Nat. Methods.* 11, 599-600 (2014).
77. H. Wickham, *ggplot2: Elegant graphics for data analysis* (Springer, New York, 2009).
78. S. Epskamp, A. O. J. Cramer, L. J. Waldorp, V. D. Schmittmann, D. Borsboom, qgraph: Network visualizations of relationships in psychometric data. *J. Stat. Softw.* 48, 1-18 (2012).

The invention claimed is:

1. A method of treating CSF-1R inhibitor resistant glioma, the method comprising administering to a mammalian subject with a CSF-1R inhibitor resistant glioma an effective amount of: (a) a CSF-1R inhibitor, and (b) an IGF-1R inhibitor or a PI3K inhibitor, thereby treating the CSF-1R inhibitor resistant glioma.

2. The method of claim 1, comprising administering to the subject an effective amount of: (a) a CSF-1R inhibitor, (b) an IGF-1R inhibitor, and (c) a PI3K inhibitor.

3. The method of claim 1, wherein the CSF-1R inhibitor is selected from the group consisting of BLZ945, GW2580, ABT-869 (linifanib), OSI-930, CEP-32496, AC708, PLX3397, AZD6495, CYC10268, IMC-CS4, RG7115, pyridyl bisamides, thiazolyl bisamides, 6-O-substituted benzoxazoles, and 6-O-substituted benzothiazoles.

4. The method of claim 1, wherein the IGF-1R inhibitor is selected from the group consisting of OSI906 (linsitinib), NVP-AEW541, GSK1904529A, NVP-ADW742, BMS-536924, picropodophyllin (PPP), GSK1838705A, AG-1024, PQ401, and BMS-754807.

5. The method of claim 1, wherein the PI3K inhibitor is selected from the group consisting of BKM120, idelalisib, SAR245409, SAR245408, BYL-719, GDC-0980, GDC-0941, wortmannin, Ly294002, demethoxyviridin, perifosine, delalisib, PX-866, IPI-145, BAY 80-6946, BEZ235, RP6530, TGR 1202, RP5264, SF1126, INK1117, Palomid 529, GSK1059615, ZSTK474, PWT33597, IC87114, TG100-115, CAL263, RP6503, PI-103, GNE-477, CUDC-907, and AEZS-136.

6. The method of claim 1, wherein if either the CSF-1R inhibitor, the IGF-1R inhibitor, or the PI3K inhibitor is able to cross the blood brain barrier it is administered to the subject systemically, and if either the CSF-1R inhibitor, the IGF-1R inhibitor, or the PI3K inhibitor is not able to cross the blood brain barrier it is administered to the subject intracranially.

7. The method of claim 1, wherein administration of the IGF-1R inhibitor and/or the PI3K inhibitor is commenced either (a) at approximately the same time as administration of the CSF-1R inhibitor is commenced, (b) after administration of the CSF-1R inhibitor is commenced, or (c) after the subject has developed resistance to CSF-1R inhibitor treatment.

8. The method of claim 1, wherein the subject was previously treated with a CSF-1R inhibitor.

9. The method of claim 1, wherein the glioma is a glioblastoma.

10. The method of claim 9, wherein the glioblastoma is selected from the group consisting of proneural glioblastoma, Glioblastoma Multiforme (GBM), astrocytoma and oligodendroglioma.

11. The method of claim 1, wherein the mammalian subject is selected from the group consisting of a rodent, a mouse, a non-human primate, and a human.

12. The method of claim 1, wherein the mammalian subject is a human.

13. The method of claim 1, wherein the subject is also treated by surgery, radiation therapy, chemotherapy, or anti-angiogenic therapy.

14. The method of claim 1, wherein the CSF-1R inhibitor is BLZ945.

15. The method of claim 1, wherein the IGF-1R inhibitor is OSI906.

16. The method of claim 1, wherein the PI3K inhibitor is BKM120.

17. The method of claim 1, comprising administering to the subject an effective amount of: (a) the CSF-1R inhibitor BLZ945, and (b) the IGF-1R inhibitor OSI906 or the PI3K inhibitor BKM120, thereby treating the CSF-1R inhibitor resistant glioma.

18. The method of claim 1, comprising administering to the subject an effective amount of: (a) the CSF-1R inhibitor BLZ945, and (b) the IGF-1R inhibitor OSI906, thereby treating the CSF-1R inhibitor resistant glioma.

19. The method of claim 1, comprising administering to the subject an effective amount of: (a) the CSF-1R inhibitor BLZ945, and (b) the PI3K inhibitor BKM120, thereby treating the CSF-1R inhibitor resistant glioma.

* * * * *